US009855323B2

(12) United States Patent
Talaat

(10) Patent No.: US 9,855,323 B2
(45) Date of Patent: *Jan. 2, 2018

(54) VACCINE CANDIDATES AGAINST JOHNE'S DISEASE

(71) Applicant: Wisconsin Alumni Research Foundation, Madison, WI (US)

(72) Inventor: Adel Mohammed Talaat, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/233,539

(22) Filed: Aug. 10, 2016

(65) Prior Publication Data

US 2017/0049873 A1 Feb. 23, 2017

Related U.S. Application Data

(63) Continuation of application No. 14/268,793, filed on May 2, 2014, now Pat. No. 9,446,110, which is a continuation of application No. 11/636,025, filed on Dec. 8, 2006, now Pat. No. 8,758,773.

(60) Provisional application No. 60/749,128, filed on Dec. 9, 2005.

(51) Int. Cl.

| | |
|---|---|
| ***A61K 39/04*** | (2006.01) |
| ***C07H 21/02*** | (2006.01) |
| ***A61K 39/02*** | (2006.01) |
| *A61K 39/00* | (2006.01) |

(52) U.S. Cl.

CPC .............. *A61K 39/04* (2013.01); *A61K 39/00* (2013.01); *A61K 2039/53* (2013.01); *A61K 2039/552* (2013.01)

(58) Field of Classification Search

CPC ....... A81K 39/00; A81K 39/04; A81K 38/164

USPC ......... 424/184.1, 185.1, 234.1, 248.1, 282.1; 536/23.1, 23.7

See application file for complete search history.

(56) References Cited

U.S. PATENT DOCUMENTS

| | | | | |
|---|---|---|---|---|
| 8,758,773 B2 * | 6/2014 | Talaat | A61K 39/04 | 424/184.1 |
| 9,446,110 B2 * | 9/2016 | Talaat | A61K 39/04 | |

* cited by examiner

*Primary Examiner* — Rodney P Swartz

(74) *Attorney, Agent, or Firm* — Quarles & Brady LLP

(57) ABSTRACT

A composition and method for immunizing a mammal infected with *Mycobacterium* are disclosed. The genes gcpE, pstA, kdpC, papA2, impA, umaA1, fabG2_2, aceAB, mbtH2, IpqP, map0834c, cspB, lipN, and map1634 of *M. paratuberculosis* and the products that they encode are vaccine targets for Johne's and Crohn's disease. Eighteen *M. paratuberculosis*-specific genomic islands (MAPs) were identified. Three inverted large genomic fragments in *M. paratuberculosis* (INV) were also identified. These genomic identifiers represent novel virulence determinants that can be used as targets for vaccines and for developments of drugs against Johne's disease. The methods can be used to deliver an immunizing compound to a mammal, to provide an immune response against Johne's or Crohn's disease in the mammal.

12 Claims, 7 Drawing Sheets

SEQUENCE LISTING

```
<160> NUMBER OF SEQ ID NOS: 38

<210> SEQ ID NO 1
<211> LENGTH: 23
<212> TYPE: DNA
<213> ORGANISM: Artificial Sequence
<220> FEATURE:
<223> OTHER INFORMATION: AMT31 transposon-specific primer

<400> SEQUENCE: 1

tgcagcaacg ccaggtccac act                                              23


<210> SEQ ID NO 2
<211> LENGTH: 30
<212> TYPE: DNA
<213> ORGANISM: Artificial Sequence
<220> FEATURE:
<223> OTHER INFORMATION: AMT38 degenerate primer
<220> FEATURE:
<221> NAME/KEY: misc_feature
<222> LOCATION: (23)..(26)
<223> OTHER INFORMATION: n is a, c, g, or t

<400> SEQUENCE: 2

gtaatacgac tcactatagg gcnnnncatg                                       30


<210> SEQ ID NO 3
<211> LENGTH: 24
<212> TYPE: DNA
<213> ORGANISM: Artificial Sequence
<220> FEATURE:
<223> OTHER INFORMATION: AMT32 nested primer

<400> SEQUENCE: 3

ctcttgctct tccgcttctt ctcc                                             24


<210> SEQ ID NO 4
<211> LENGTH: 20
<212> TYPE: DNA
<213> ORGANISM: Artificial Sequence
<220> FEATURE:
<223> OTHER INFORMATION: AMT39 T7 primer

<400> SEQUENCE: 4

taatacgact cactataggg                                                  20


<210> SEQ ID NO 5
<211> LENGTH: 19
<212> TYPE: DNA
<213> ORGANISM: Artificial Sequence
<220> FEATURE:
<223> OTHER INFORMATION: AMT 152 primer

<400> SEQUENCE: 5

ttgctcttcc gcttcttct                                                   19


<210> SEQ ID NO 6
<211> LENGTH: 19
<212> TYPE: DNA
<213> ORGANISM: Artificial Sequence
<220> FEATURE:
<223> OTHER INFORMATION: SP-6 primer
```

<400> SEQUENCE: 6
tatttaggtg acactatag 19

<210> SEQ ID NO 7
<211> LENGTH: 1167
<212> TYPE: DNA
<213> ORGANISM: Mycobacterium avium

<400> SEQUENCE: 7
tcagcttacg gtgacaaccg gtgaaccgct ggatgttgcc tccggcccgc cctcactgtt 60
catctgcgcg gcgatgcgca tcgcctcttc gatcagcgtc tccacgatct gggattcggg 120
caccgtcttg atcacctcgc cgcgaacgaa gatctgcccc ttgccatttc ccgacgcgac 180
gcccaggtcg gcctcgcggg cctcccccgg cccgttgacc acgcagccca tcaccgcgac 240
ccgcagcggc acgtccaggc cgtccaggcc ggcgctgacc tcgttggcca gcgtgtagac 300
gtcgacctgc gcgcgcccgc acgacgggca ggacacgatc tcgagcgaac gcggccgcag 360
gttcagcgac tccaggatct ggatgccgac cttgacctcc tcgaccggcg gcgccgacag 420
cgacacccgg atggtgtcgc cgataccgcg cgacagcagc gcaccgaacg cgaccgcgga 480
cttgatggtg ccctgaaacg cggcccggc ctcggtgacg cccaggtgca gcgggtagtc 540
gcactgctcg gcgagttgct cgtaggcggc gaccatcacc acggggtcgt tgtgcttgac 600
gctgatcttg atgtcggaaa agccgtgctc ctcgaacagc gaggcctccc acagcgcgga 660
ctcgaccagc gcctcggggg tggccttgcc gtacttggcc atgaaccgct tgtccagcga 720
gcccgcgttg acgccgatgc ggatcggaat gcccgctgcc gcagcggctt tggcgacctc 780
gcccacccgg ccgtcgaatt ccttgatgtt gccggggttc acccgcaccg cggcgcagcc 840
ggcgtcgatg gccgcgaaga tgtacttggg ctggaagtgg atgtcggcga tcaccgggat 900
ctggctgtgc cgggcgatct cggccagcgc gtcggcgtcc tcctggcgcg ggcaggccac 960
ccggacgatg tcgcagccgg ccgcggtcag ctcggcgatc tgctgcagcg tcgagttcac 1020
gtcgtgggtc ttggtggtgc acatcgactg caccgagatc ggatagtcgc tgccgacccc 1080
gacgtcgcgc accatcagtt ggcgcgtgcg gcgccggggc gcaagcgtgg gcgccggggt 1140
ctgcggcatg cccaggcctg tcgtcac 1167

<210> SEQ ID NO 8
<211> LENGTH: 12084
<212> TYPE: DNA
<213> ORGANISM: Mycobacterium avium

<400> SEQUENCE: 8
gtgggtggag acttggggga gtcgatggcg agggatgatc gggcgtttcc gctgacgcga 60
gggcagcttg atatctggtt atcccaggaa gccggtttcg ccggcaccca gtggcagctc 120
ggtctgctgg tcaagatcga cggcaaggtc catcgcgacg cgctcgagca ggccatcacc 180
caggccgtcg ccgaagccga acccggccgg gtctcgttct tcgagctcga cggccaggtg 240
gtgcagaagc cgatcgacta cccgcacgtc gagctggctt ttcacgacct gaccgaccac 300
gccgacccgg tggccgaggc gcgggagatg tcttcggcca ttcagcgcac gccgatgccg 360
ttgaacggcc aaatgttcaa attcgtgctt ttccaaacag ggcacgacga attctatttg 420
tttggttgct gccaccacat agctatcgac ggtctgggca tggctcttgt ttgccgacgg 480
gtggccacca tttattcggc aatggtggcc ggtaagccga ttccggacgc ttacttcggc 540
acggtgcagg acctgatcga cctggagtcg ggctacgagg cctccccgga ctatgccgag 600
gacaaggcgt actggagcga gcacctcccg ccggagagcg ggccggtcga ccggctgccc 660
gacgccgaag gggagcgcga ccactactcg ccgtccgcgt cggtgcagct ggacccgtcc 720
gtcgccaacc ggatcaagga gctgtccaaa aagcttgcca tccgccgctt ttcggtcacc 780
accgccgcgt gcgcgctgtt ggtgcgcggc tggtcgggta gcggatcgga ggtggcgctg 840
gacttcccgg tcagccgacg ggtgcgtccg gagtccaaaa cgctgcccgc gatgctggcc 900
ggcgtggtgc cgctggtgct cagcaccgcg cccgagtcga cggtggccga cttctgcaag 960
cacgtcgaca agcgcatccg cgagctgctg gcgcaccagc gcttcccggt gcacaccctc 1020
gaaggcgacg ggttgcggca ggcgcccaac cgggtcggga tcaacttcat cccgtcccgg 1080
ctgacgctgg acctggccgg ttccccggcg acggcgtcgt acaccaacca cggcccggtg 1140
gggcacttcg ggctgttctt cctgggcgcc ggcgaccagc tgttcctcag caccgcgggc 1200
ccgggccaac cgttcgccag cttcggcgtc gcggacctgg ccggtcggct gcagcagatc 1260
ctggccgcga tgaccgagga cccggaccgc ccgctgtcct cgatcgaact gctgaccggc 1320
gacgagcccg cgctgatcga ccggtggagc aaccgtccgg cgctgaccga gcccgcaccc 1380
gccccggtgt cgatccccca ggccttcgcc gaacacgtgc agcgcacccc cgacgcggtg 1440
gcggtgacgt tcggggcgac ctcgctgacc tacgcccagc tcgacgaggc gtccaaccgg 1500
ctgggccatc tgctcgccga ccacggcgtg ggcccgggcg actgcgtggc ggtgatgttc 1560
ccccgctgcg ccgacgccat cgtctcgatg ctggcggtgc tcaagaccgg ggcggcctac 1620
gtgccgatcg acccggcgca cgcgtcgtcg cggatggact tcgtgctcgc cgacgccgcc 1680
cccagcgcgg tgatcaccac ctccgacctg cgctcgcggc tggacgatca cgacctcctc 1740
gtcgtcgacg tgcacgaccc ggccgtcgaa gcccagcccg gcaccgcgct gccgtggccg 1800
gcgccggagg acaccgccta catcatctac acctcgggaa ccaccgggac cccccaaaggt 1860 gttgccattc ctcatctcaa cgtcacctgg ctgatcgagt cgctggacgc cggcctgccg 1920
cccggaaacg tgtggacgca gtgccactcg tcggcgttcg acttctcggt gtgggagatc 1980
ttcggcgccc tgctgcgcgg ccggcgactg ctggtggtgc ccgagtcggt ggcgtcgtcg 2040
ccggaggact tccacgccct gctggtcgcg gagcaggtca gcgtgctcac ccagacgccg 2100
tcggcggtgg cgatgctctc acccgagggc ctggagtcca ccgcgctagt ggtggccggc 2160
gaggcctgcc cgaccgacgt ggtcgaccgg tgggcggcgc ccggtcgggt gatgctggac 2220
gcctacggcc cgaccgagac cacggtgtgc gcgtccatca gcacaccgct gacggccggc 2280
gacccggtgg tgccgatcgg ctcgccgatc gccggggcgg cgatgttcgt gctcgacaag 2340
tggctgcagc cggtgcccgc cggcgtggtg ggcgagctgt acctggccgg ccgcggcgtg 2400
gggcacggct acgtgcgccg gcccggcctg accgcctcgc ggttcgtgcc caacccgttc 2460
ggcgcccccg gctcgcggat gtaccgcacc ggcgacctgg tgtgctgggg ccccgacggg 2520
cagctgcagt acctgggccg cgccgacgag caggtcaaga tccgcggctt ccgcatcgag 2580
ctcggcgaaa cccagtcggt gctggccggt ttggacgggg tggagcaggc ggcggtggtc 2640
gcccgcgagg accggcccgg cgacaagcgc ctggtcggct acatcaccgg caccgccgac 2700
ccggccgagc tgcgcgcgca gctggccgac cggctgccgc cctacatggt cccgaccgcg 2760
gtgatggtgc tggacgcgct gccgctgacc ggcaacggca agctggacaa gcgcgcgctg 2820
ccctcgccgg aatacgccgc cggcgaatac cgggcgcccg gcgacgcgat cgaggagatc 2880
ctggccgaca tctacgccca ggtgctgggc gtggagcggg tcggggtgga cgactcgttc 2940
ttcgacctgg gcggcgacag catcctgtcc atgcaggtgg tggcccgcgc ccgcgcggcg 3000
ggggtgatct gtcggccgcg cgacgtgttc gtcgagcaga cggtggcccg gctggcgcgg 3060
gtgtcccaag tggctgtcga cggcgagctg ggcgccgccg acgaggggat cgggccggtg 3120
cagcccaccc cgatcatgcg ctggctgcag gacatcgacg gcccgatcga cgagttcaac 3180
cagaccatgg tgctggccgc gcccgccggg gtcggtgtcg acgacgtcgc ggtggtgctg 3240
caggcactgc tggaccggca cgcgatgctg cggctgtgcc tcgacgacga cggcgccggc 3300
ggctgggacc tgcacgtgcc gcccccccggt tcggttgacg cccgcgccat cctgcgcacg 3360
gtcgacgtgc tctccgaggc cgcgctggcg cgggcgcggt cccggctgaa ccccggcgcc 3420
ggcctgatgc tgtccgcggt atgggcaagc gccaccaacg aattggccct ggtcgttcac 3480
cacctggcgg ttgacggggt gtcgtggcgg acgttgatcg aggacatcaa catcgcctgg 3540
gcgcagcatc acagcggtca ggagatcgcg ttgccggtgc cgggcacgtc gtttgcgcgg 3600
tggtcgtcga ttctggccga gtacgccaag agcccggcag tggtggctgc ggcggcggcg 3660
tggcagcagg tggtggccac gccggcggtg ctgccggcgg tggggcccga tgacacctat 3720
gcctcggagg ggcagttgtc ggcgtcgctg gatgtgcaga ccacccggtt gttgttgggg 3780
gaggtgccgg cggcgtttca cgctggggtg caagacattt tgctgattgc gttcgggttg 3840
gcctgcacgg agttcgtggg tggtggcgcg ccgatcggta tcgacgtgga gggtcacggg 3900
cggcacgagg agatcgcctc gggggtggat ctgtctcgca cggtgggctg gttcaccacg 3960
aaatatcctg tggcactgac gatcagtcag cgtctggatt gggcgcgggt ggtggcgggg 4020
gaggccgcgc tgggcgcggt gatcaaggat gccaaggagc agttgcgggc gctgcccgac 4080
ggcctgagct acgggttgct gcgctacctg aaccccgaga tcgaggtgca ggggccggat 4140
ccggtgatcg gattcaacta cctgggccgg ctcggcggcg cggccgccga cctgtccgac 4200
gagcactggc gcctcagccc cgacagtccg tcggtgagcg ccgcggccgc ggcgatccca 4260
ctgccgttgg gacataccgt cgaactcaac gccggcacca tggacaccga cgccggcccg 4320
cagttgcacg ccaactggac ctgggcgcgc tccgtgctca ccgacgagca gctaaaccgg 4380
ttgagccggt tgtggttcga ggcgctgacc ggcatctgcg cgcacgtgca ggccggcggc 4440
ggcgggctga cgccgtccga catcgcgccc accctcctcg accaaggccg gatcgagcag 4500
ctggaacggc actacgacgt cgccgacatc ctgccgctga ccccgctgca gcaggggctg 4560
ctgttccacg cgaccggaag ccatgccgag ggcgacgtct acgcggtgca gctgagcgtc 4620
acgctgcgcg gcgccctcga cccgcaccgg ctacaccgcg ccctgcacac cgtcgtcacc 4680
cgccacccga acctggccgc ccgcttctgc cccgagctcg gcgagccggt gcagatcatc 4740
ccggccgaac ccgaaatggc ttggcgctac ctcgaactcg acggcggcga catcgacgaa 4800
cagctcgagc agctgtccgc ggacgaacgc gccgcggtgc gagagctcgg cgaccgcccg 4860
ccgtttggcg ccgcgctgat ccgcaccgcg gacacggaac accggttcgt gctcaccgtc 4920
caccacctgg tgatggacgg ctggtcgctg ccggtgctgc tgcaggaaat cttcgcctgc 4980
tactacggtg cccggctgcc ggcgccggcg ccgtaccgcg gcttcgtcac ctggctggcg 5040
gcccgcgacg tgccggccgc ccgcgccgca tggcgcgcgg tgctcgacgg tttcgacacc 5100
cccaccctgg tggccccgcg gggtgccgac gcgcccgggc ggcgcggggt cgcctcgttc 5160
cgggtggccg ccgaaaccac cagcgcggta agcgaactcg cacgccgccg ccgcaccacc 5220
gtcaacaccg tgttgcaggc cgcctgggcg cagctgctga tgatgctgac cggccagcac 5280

-continued gacgtcgcgt tcggcaccgc cgtctctggc cggccggccg agctgcccgg cgccgagtcg 5340
atggtcgggc tgttgatcaa caccgtcccg gtgcgcgccc acgccaccgc ggcgaccacc 5400
atcgcggacc tcgtcgacca gctgcaacgc gcccacaacc acaccgtgga gcatcagcac 5460
ctggcgctca acgaaatcca ccgcatcacc ggacaggacc aactcttcga caccctgctg 5520
gtctacgaga actatccgat cgacaccgcc gccctgtcgg ccgccgacga cctcaccgcc 5580
accgaattca gctgccacga ctacaaccac tacccgctgt cgctgcaagt ggtgcccggc 5640
gacgaactgg gccttcgcct cgaattcgac accgacgtgt tcgacccggc ggccatcgac 5700
accctggccg accggttgcg gaagctgctg gccgccatgc ccgccgaccc ggaccgcccg 5760
ttgcgatcac tggacctgct cgacgccacc gagcacaccc ggctgcaacg gtggggcaac 5820
cggccggcgc tgagccggcc ggcaaccggg ccgtcgctgc cggagttgtt cgccgcacag 5880
gtcgccaacg ctccgcacgc cgtcgcgctg cgctacgccg gccggtcgat gacctaccgc 5940
gaactcgacg aggcgtcgac ccggctggcc cacctgctgg ccggccacgg cgccaccccg 6000
ggttgctttg tggcactgct gttttcccgg tcggccgagg cgatcgtcgc gatgctggcg 6060
gtgctgaaaa ccggcgcggc ctacctgccg atcgacccgg cgctgccggc gacccgcatc 6120
gagttcatgc tcggcgacgc cgcacccgtc gtcgcggtca gcaccgccga cctgcgcgcc 6180
cggctggagg ccttcggcct gccggtcgtc gacgtcgccg ccaccggcgc ccagcccggc 6240
ggcccgttgc cggcgcccgc gcccgacaac atcgcctatc tgctctacac gtccgggacc 6300
accggcgtcc ccaagggcgt tgcggtcacc caccgcaacg tcgcccagct gctcgagtcc 6360
ctgcacgcgt cgctgcccgg caccggggtg tggtcgcagt gccactccta cggcttcgac 6420
gtctcggtcc aggagatctg gggcgccctg gccggcggcg gccggctggt ggtggtgccc 6480
gagtcggtga ccagctcacc cgacgagctg cacgcgctgc tgatcgccga gaacgtcacc 6540
gtgctcagcc agacaccgtc ggcgctggcg gcgctgtcac cacgaaacct gcacgcggcg 6600
ttggtgatcg gcggcgagcc ctgcccggcc gcgctcgccg accggtgggc gcccggccgg 6660
gtgatgatca acgcctacgg ccccacggaa accaccgtcg acgcggtgct cagcacaccg 6720
ctggccgccg gcgccggagc acccccactc ggctccccgg tagcgggtgc gacgctgttc 6780
gtgctggacg cgtggctgcg gcaggtgcct gccggtgtga ccggcgagct ctatatcgcc 6840
ggcgccgggg tggccgccgg ctatctgggc cggcccggtc tgacggcggc gcggttcgtg 6900
gcctgcccgt tcggcgacgc cggtgcgcgg atgtaccgca ccggcgatct ggtgcgctgg 6960
gatcgcgacg gccgactgca ctacgtcgcc cgggccgatc agcaggtcaa gattcgcggc 7020
caccgcatcg agctgggcga aatccattct gcgctggccg aattggacgg cgtcggggaa 7080
gtagcggtga tcgcccgcga ggaccgcccc ggcgagaaac ggatcgtcgg ctacctcacc 7140
ggcaccgccg acccggcggc gatccgcgcc cggctggccg agcggttgcc ggcctacatg 7200
gttcccgccg cggtgctggc gatcgaggcg ctgccgttga ctcccaacgg gaaactggac 7260
gcccgggccc tgccggcgcc ggaatacgcg ggcggggcat accgggcgcc gtccactccc 7320
accgaggaga tcatcgccgg catctacacc caggtgctcg gcctgcacag ggttggtgtc 7380
gacgactcgt tcttcgacct gggcggtgat tcgctgtcgg cgatgcgggt gatcgccgcc 7440
gtcaacgccg gcctcgacgc ccggctgtcg gtgcgagtgt tgttcgaagc gcccaccatt 7500
gcgcaactgg cggcgcgcct cggcgaaggc gggcaccggt tcgccgcggt ggtggccgcc 7560
gagcggccgg cggtggtgcc gttgtcgttc gcgcagtcgc ggctgtggtt catcggccag 7620
ctgcacgggc cgtccccggt gtacaacatg gtggccgcgc tgcggctgca cgggccggtg 7680

```
gacatcggcg cgctgggcgc cgcactgcat gatgtcgtga cccggcacga gagcctgcgc   7740
acggtgttcg ccgcgaccga cgggacgccc gcccaagtgg tgctgccgcc cgaccgtgcc   7800
gacatcggct ggcaggtcat cgacgccagt ggctggtcgc cggcccgagt ggatgacgcc   7860
atccgcgaca ccgcccggca tacctttgac ctggctgctg aaattccgtt gcgtgcagtg   7920
cttttgcggt gtggcgcgga ggagcatttg ttggtggcgg tggtgcatca tattgccgcg   7980
gacgggtggt cgttgacgcc gttggtgcgt gacttggcgc gggcgtatgc gagtcggtcg   8040
gcggggcggg tcccggattg ggtgccgttg ccggtgcagt atgtcgatta cacgttgtgg   8100
cagcgcgccc agttcggtga cctcgacgac ccgcacagcc tgatcgccgg tcagctgcgc   8160
tactgggagc acaccctggc gggcatgccc gagcggttgg aattgcccac cgatcggccg   8220
tatccggtgg tggccgattt ccgcggcgcc agtgtcgcgg tggagtggcc ggcgcagttg   8280
cagcagcaaa tatcgcggtt ggcgcgggcg cataatgcca ccagtttcat ggtggtgcag   8340
gccgcgttgg cggtgctgct ggccaaggtg agcgcgagtt cggatgtggc ggtgggcttt   8400
ccgatcgccg ggcggcgcga cccggcgctg gatgacgtgg tgggtttttt cgtcaacacc   8460
ctggtgctgc gggtggacgt ctccggtgat cccacggtgg gcgagctgct ggcgcgggtg   8520
cggcaacgca gcctggctgc ctatgagcat caggatgtgc cgttcgaggt gctggtggag   8580
cggctcaacc cggcccgcag tctggcgcac catccgctgg tgcaggtgat gttggcctgg   8640
cagaacatcg agcccaccga gctgagcctg gggcaggtgc gggtgactcc gctgccggtg   8700
gatacccgca ccgcccggat ggatctggct tggtcgctgg ccgaacgctg ggcacccgat   8760
ggctcacccg ccggtatcgg gggagcggtc gaattccgca ccgacgtgtt cgataccgcc   8820
acggtggagg cgttgaccca gcggttgcgg cgggtgctgg cggccatgac cgccgacccc   8880
ggccgccggt tgtcctcgat cgacctgctc gaccccgacg agcacgcccg cctcgacgcc   8940
ctcggcaacc gcgcagcact gacccgacca caaaacccgc ccacctccat ccccgcgatg   9000
ttcgccgccc agatggcgcg caccccgcac gccgtggcgc tgaccgccaa cggtcgctcg   9060
gtcacctatc gccggctcga ggaacacgca aaccaattag cgcaccaact tattcgttac   9120
ggcgcagggc cgggcgattg cgtggcgctg ctgctggagc gttccgccga ggccgtcgcg   9180
gccatcctgg gggtgctcaa ggccggggcc gcctacctgc ccatcgaccc cagcctgccc   9240
agtgcccgga tcgagttcat gctcaccgac gccgcacccg cggccgtgct caccagcacc   9300
gaattccatt gccgtctaca ggattaccac cagaccgtca tcgacgtcga cgacccgtcg   9360
atccgggaac aacccgtcac cgcaccaccg gcgcccgccc cggacaatat cgcctacctc   9420
atctacacct cgggcaccac cggcgtcccc aaaggcgtcg cggtcaccca ccgcaacgcc   9480
acccagctgt tcgcgtcgct gggagccgcc ggcctgcccg ccgcacccgg aaaggtgtgg   9540
ggccagtgcc attcgctggc cttcgacttc tcagtgtggg agatcttcgg cgcgctcctg   9600
aacggcgggc gcgtgctggt ggtgcccgac gacgtggtgc gctccccgga agacctgtgc   9660
gccttgctga tcgaggaacg ggtcgacgtg ctcagccaaa cgccgtcggc attcgatgcg   9720
ctgcagcgcg ccgactccgc ccggcggctc aacccgcaga cggtgatctt cgggggcgaa   9780
gcgctgatcc cgcaccggct gggcggctgg ctggacgggc atcccgcacg cccgcggctg   9840
atcaacatgt acggcatcac cgagacgacg gtgcacgcct ccttccggga gatcgtcgac   9900
ggcgacatcg acggcaacgt cagcccgatc ggaatgccct tggcgcactt gggattcttc   9960
gtgctggatg gatggctgcg gcctgtgcct gccggtgtga ccggcgagct gtacatcgcc  10020
```

-continued

```
ggcgccgggg tggccgccgg ctatctgggc cggcccggtc tgacggcgtc gcggttcgtg  10080
gcctgcccgt tcggcggcgc cggcgagcgg atgtaccgca ccggggacct ggcccggtgg  10140
ggcgccgacg ggcagctgca atacctgggc cgcgccgacg aacaggtcaa gattcgcggc  10200
taccgcatcg aactcggcga aatccagtcc gccctggccg aattggacag cgtcgagcag  10260
gcggcggtga tcgcccgcga ggaccgtccc ggcgacgagc ggctggtcgc atacgtcacc  10320
gggaccgccg acccggcgca gctccgcacc gcgctgaccg aacggctgcc cgcctacctg  10380
gtccccgccg cggtgctggt gctggacgcg ctgccgttga cacccagcgg caaactcgac  10440
accggcgccc tgcccgcccc cgactaccag ggccccgagg actacctggc cccggccggc  10500
gcggtggagg agatcctggc ctggctctac gcccaggtgc tggggctgcc gcggcgggtc  10560
ggggtgcagg aatccttctt cgacctgggc ggcgactcgc tgtcggccat gcggctggtc  10620
gcggccatct acaacgcgct ggacatccac ctgccggtgc gggccgtctt cgaggcgccc  10680
tcggtgcgca gcctgagcca gcggctgaac gccgatcccg ctgtggcgca aggccttcgg  10740
gccgacttcg catcggtgca cggccgcgac gccaccgagg tgtacgccag cgacctgacc  10800
ctggacaagt tcatcgacgc cgcgacgctg tccgccgcac ccgcgctgcc cggccccggc  10860
gccgaggtgc gcaccgtgct gctgaccggc gccaccggct ttctgggccg ctacctggtg  10920
ctgcaatggc tggaacgcct ggaactggcc gacgggaaac tcatctgtct ggtgcgggcc  10980
gcctcggacg acgacgcgcg gcgccgcctc gagcgcactt tcgacagcgg cgatcccgcc  11040
ctgctgcggt acttccacga actggccgcc gaccacctcg aagtcatcgc cggcgacaag  11100
ggccgcgcca acctcggcct ggacgatcgg acctggcagc ggctggccga caccgtcgac  11160
ctgatcgtcg acgcggcggc cgtggtcaac ggcgtgctgc cctaccagga actgttcggc  11220
cccaacgtcg ccggcaccgc cgagctgatc cggctggcgc tgtccaccag actcaagccg  11280
tacagctacg tgtcgaccgc caacgtcggc gaccagatcg agccgtcggc gttcaccgag  11340
gacgccgaca tccgggtcgc cgggccgatc cgcaccatcg acggcggcta cggcaacggc  11400
tacggcaaca gcaagtgggc cggcgaggtg ttgctgcgcg aggcgcacga cctgtgcggg  11460
ctgccggtct cggtgttccg ttgcgacatg atcctggccg acaccagcta cgcgggccag  11520
ctcaacctgt cggacatgtt cacccggctg ctgttcagcg tggtggccag cggcgtggcg  11580
ccgcgctcgt tctaccggct cgacgcgcac ggcaaccggc agcgcgcgca cttcgacgcg  11640
ctgccggtcg agttcgtcgc cgaggcgatc gccacgctgg gcgcccaggt gggccgggac  11700
gccggcatcg ggttcgcgac ctaccacgtg atgaacccgc acgacgacgg catcgggctc  11760
gacgagtacg tcgactggct gatcgaggcg ggctacctga tcgagcgggt cgacgacttc  11820
gaccagtggc tgcaccggat ggagaccgcg ctgcacgccc tgccggaacg gcagcgccac  11880
cagtcggtgc tgcagctgct ggcgttgcgc aaagcccggc acgtgccgcc ggccgacccg  11940
gcccgcggct gcctggggcc caccgagcgg ttccgcgctg cggtgcaaga agccaaaatc  12000
ggcgccgaca acgacatccc gcacatcacc gccccggtca tcgtcaaata cgtgaccgac  12060
ctgcagttgc tgggcttgct ctga                                          12084
```

<210> SEQ ID NO 9
<211> LENGTH: 876
<212> TYPE: DNA
<213> ORGANISM: Mycobacterium avium

<400> SEQUENCE: 9

```
ctagctggtg accggatagc ggtggtcgag ttgcagattt agctgcagca cgttgacgca     60
```

-continued cggttcaccg aaaaagccca gcgcgcgccc gctgctgttc tgcgccacca gctcccggat 120
ctgctccggg cggacgtggc gcaccttggc cacccgcgcc acctggatgt cggcgtaggc 180
cggcgagatg ttcgggtcca ggccgctgcc gccggcggtg accgcgtcgg cgggcacggc 240
cggggccgcc ggtgccgctc cgcggatggg cacgatctgg ccgagcgaat agtcctcccc 300
ggtcttggcg cattcgacgc gcaccccctc gtagaggctc acgaacggtg tcggggtcga 360
ttcgcacggt tcgttgacgc tgaccacccg ggccgggtgg gtgacgttgc cgcgctcgtc 420
gcgcggcccg atcaccgaca gcaccgcccc cacaccgccg ccggtgcaga acggccgcga 480
cccgtcgacg ccctccagtt tggcgacggc ggcgctgcgc gagcacaccg tggtcagcag 540
gccgggtttg ccgggtgcgt cgacgatgct ctccggcccc aggttgctgc cgccgctgga 600
ggtcgggtcg tagccggtgc cggccgccga ggggcgactc tgaaagtact gcggcagcgg 660
gttgccgtcc ttgtcggtga acagctggcc gatcagtctg ctgcccaccg gcttgccgtt 720
ggcggtcagg atcgacccct cggcgtggtc gcgtaatccg gggaactgcg ccaccaccca 780
gacgagcagc ggataggcca ggccggtgat cacggtcagc accagcagcg cccgcaacgc 840
cgcccagtgc aggcgaatga agttcgacag tgtcat 876

<210> SEQ ID NO 10
<211> LENGTH: 1518
<212> TYPE: DNA
<213> ORGANISM: Mycobacterium avium

<400> SEQUENCE: 10
gtggtcacat tcgggacggt gcataactgg gatccgggaa ccggttcggt catttcctgg 60
cacgcgactc cggcggcgcg ggaaaaagcc cggcaggcgc cgattagcga cgtgccggcc 120
agttatcagc agttgcatca tcttcgccgg ttcagcgaac acgccgcccg gggcctggac 180
atggcgcggc tgaacatcgg ggtctgggat atctccggcg tgtgcgacgt ggcggccatg 240
accgaagcga tcaatgccca tctgcgccgg cacgacacct accacagttg gttcgagcat 300
cggaccgacg gccgtatcgt ccggcacacc ttcgccgatc ccgccgacat cgagttcgct 360
gcgctgcagc gcggcgagat gacgccgacc gagctgcgcg cccacatcct ggccaccccg 420
aatccgctgc gctgggactg cttcaccttc ggtctcgtcc agcacccgga tcacttcacc 480
ttctatatga gtgcggacca tctggtcatc gacgggatgt cggtcggcgt gatcttcctc 540
gaaatccatc tgacgtatgc cgctttggtg agcggcgggc gcccgctgcc gctgcccgag 600
ccggccagct accacgacta ctgccgccgg cagcaccagc acaccgaggc gctgaccctg 660
cagtcccccc aggtgcgcgc atggattcga ttcgcgcagg acaacggcgg aaccctcccg 720
agtttcccgc tgccacttgg cgatccgtcg gtgccgtgcg gaagcggtgt ggtggtcgca 780
ccgctcatgg acgagagtca gaccgagcgg ttcgacgcca cctgcacgaa ggcgggggct 840
cgcttcagcg gtggcgtggt cgcctgcgcg gccttcgccg agtacgagct gaccggggcg 900
gagacgtatt gcgcgatcac gccgtatgac caccgcagca cgccggccga attcgtgact 960
ccgggctggt tcgccagctt catcccggtc accgtcccgg tcgccggggc ctcgttcggt 1020
gacgcggtga tcgccgcgca ggcgtccttt gattccgcta tcggtctggc cgacgtcccc 1080
ttcgaccgcg ttttggagct gtcgtctttc ggcgggcgaa tcagcaaacc gacgggcgac 1140
gtccacatgc tctcgttcgc cgacgcgcgg gggatcccgt tcagcgggca atgggacggc 1200
ctgaacgccg ggatttacgg cgacggccgg tcgtccgatc aggtgcttat gtgggtcaac 1260
cgattcgaca ccgagaccac cttgacggtg gcgttcccac agaatccggt cgcccgcgat 1320
tcggtcgagc gctacatccg ggcggtcagg gcgatgtgtc tgcgggtggt ggagcacggt 1380
gccgccgcgg tgccgaaccg ccggcgcgtc gttgccgcgg tcaacgcgtc ggccgcccga 1440
tcgaccgcca acgccgccga ccgcaccgac cgtcgcctgc aaggcgcggg cttcggcgcc 1500
aacccggtcc ttcggtga 1518

<210> SEQ ID NO 11
<211> LENGTH: 801
<212> TYPE: DNA
<213> ORGANISM: Mycobacterium avium

<400> SEQUENCE: 11
atggacctgg acgcgttggt ggcgcgggcg tcggcgatcc tcgacgacgc ctcgaagccc 60
ttcctcgccg gtcaccgcgc cgactccgcg gtccgcaaga agggcaacga ctttgccacg 120
gacgtcgacc tcgccatcga gcggcaggtg gtcgccgcgc tggtggaggc caccgggatc 180
ggcgtgcacg gcgaggagtt cggcggttcg gccgtcgact cggaatgggt gtgggtgctc 240
gacccggtgg acggcacgtt caactacgcg gccgggtccc cgatggccgg gatcctgctg 300
gccctgctgc accacggcga cccggtggcc gggctgacct ggttgccgtt cctcgaccag 360
cgctacaccg cggtgaccgg cggcccgctg cgcaagaacg aaatcccgcg gccgccactg 420
acttccatcg acctggccga cgccctggtc ggggccggat cgttcagcgc ggacgcccgc 480
ggccggttcc cggggcgcta ccggatggcg gtgctggaaa acctcagccg ggtctcgtcc 540
cggttgcgca tgcacggctc caccggcctg gatctggcct atgtcgccga cgggatattg 600
ggcgcggcgg tcagtttcgg cgggcacgtg tgggaccacg ccgccggggt ggcgctggtg 660
cgggccgccg gcggcgtggt gaccgacctg gccgggcggc cgtggacccc ggcctcggat 720
tcggcgctgg ccgccggacc cggcgcgcac gccgagatcc tggacatcct gcgcaatatc 780
ggccgaccgg aggactactg a 801

<210> SEQ ID NO 12
<211> LENGTH: 861
<212> TYPE: DNA
<213> ORGANISM: Mycobacterium avium

<400> SEQUENCE: 12
atgacgggct tggaaccgta ttacgaggaa tcgcagtcca tctacgacgt ctccgacgaa 60
ttctttgcgt tatttctcga tccgaccatg gcctacacgt gcgccttctt cgaacgcgac 120
gacatgacgc tcgaagaagc gcaaaccgcg aagttcgacc tggcgctggg caagctgaac 180
ctcgagcccg ggatgacgct gctggacatc gggtgcggct ggggcggcgc actgaagcgg 240
gccctggaga agtatgactt caacgtcatc ggaatcacgt tgagccgcaa ccaattcgaa 300
tacagcaaga agctgctggc cggatttccg acggaccgca acatcgaggt gcggctgcag 360
ggctgggaag agttcgacga caaggtcgac cggatcgtca ccatcggcgc cttcgaggcg 420
ttcaaaatgg agcgctattc cgcatttttc gaccgcgcct acgacatcct gcccgacgac 480
ggccggatgc ttttgcacac catcttgacc tacacccaga agcagcagca cgagcgcggc 540
gtttcgatca cgatgagcga tttacggttc atgcggttca tcggccagga aatttcccg 600 ggcggccagt tgccggcgca ggaggacatt ttcaaattcg gtgaggcggc gggcttttcg 660
gtggagcggg tgcagctgct gcgcgagcac tacgcgcgga ccctcaacat ctgggcggcg 720
aacctggagg ccaacaagga caaggccatc gccatccagt cgcaagcggt ctacgaccgc 780
tacatgcact acctgaccgg gtgcgagaac ttcttccgca agggcatcag caatgtgggg 840
caattcacgc tggtcaagta g 861

<210> SEQ ID NO 13
<211> LENGTH: 750
<212> TYPE: DNA
<213> ORGANISM: Mycobacterium avium

<400> SEQUENCE: 13
tcacaggtgc cggccgcccg tgatctccat gacggtgccg gtcatgtacg acgacatgtc 60
ggaggccaaa aacagcgcca cgctggcgac ctcgctgggc tcgccggccc ggcccatcga 120
cacctcggcc accttggagt cccaaatgcg ttgcggcatg gcctctgtca tcgccgagcg 180
gatcaaaccg gggcgatcg cgttcacccg cacacccagg taggccagct ccttggcggc 240
cgccttggtc atgcccacga tgccggcctt ggccgccgag tagttggtct ggccgaccat 300
gccgaccttg cccgacaccg acgacatgtt gatgatggcg ccgcgcttgt tttcccgcat 360
gatcgccgcc gccaatcggg tgccgttcca ggtgcccttc aagtgcacgg cgatgacctg 420
atcgaactgc tcctcggtca tcttgcgcat ggtggcgtcc cgggtgatcc cggcgttgtt 480
gaccatgatg tccaggccgc cgaaccgctc gacggcggtc tggatcagcg tttcgacctc 540
ggacgacttg gtgacgtcgc agcgcacggc cagcgccacc tggtcaccgc ccagctgttt 600
ggccgcggtt tgcgtcgcct ccagattgac gtcgccgagg acgacccgcg cccccttcggc 660 gacgaaccgt tcggcgatcg cgaaccccaa accttgtgcg ccacctgtga tgaccgcggt 720
ctgaccactg agcaaggaca cctgtaccac 750

<210> SEQ ID NO 14
<211> LENGTH: 2289
<212> TYPE: DNA
<213> ORGANISM: Mycobacterium avium

<400> SEQUENCE: 14
atggcgatca tcgacaaaga gacgcaagtc cggccatcgt tcgacgacga ggtagccgcc 60
acgcagcgct acttcgacga cccccgcttc gcccgcatca cgcgcctcta caccgctcgg 120
caggtggccg agcagcgcgg caccatccgc accgactaca ccgtggcacg cgacgcggcg 180
gccgcgttct acgaacggct gcgcgagctg ttcgcccaga agaagagcat caccaccttc 240
ggcccgtact cgcccggcca ggcggtcacc atgaagcgga tgggcatcga gggcatctac 300
ctcggcgggt gggccacctc ggccaagggc tccaccaccg aggacccggg gcccgacctc 360
gccagctacc cgctgagcca ggtgcccgac gacgccgcgg tgttggtgcg cgcgctgctc 420
accgccgacc gcaaccagca gtacctgcgg ctgcagatga gcgaacagca gcgcgccgcc 480
accaaggagt acgactaccg gccgttcatc atcgccgacg ccgacaccgg ccacgggga 540 gacccgcacg tgcggaacct gatccgccgt ttcgtcgagg tcggggtgcc cggctaccac 600
atcgaggacc agcggcccgg caccaagaag tgtggccacc agggcggcaa ggtcttggtg 660
ccctccgacg agcagatcaa gcggctcaac gccgcgcgct tccagctcga catcatgcgg 720
gtgcccggga tcatcgtcgc ccgcaccgac gccgaggccg ccaacctgct ggacagccgc 780
gccgacgagc gcgaccagcc gttcctgctg ggtgccacca acctcgacat cccgtcgtac 840
aaggcgtgct tcctggcgat ggtgcgccgc ttctacgagc tgggtgtcaa ggacctcaac 900
ggccacctgc tctacgcgct gccggaggcg gagtacgccg aggccaccgc ctggctcgag 960

-continued cgtcagggca tccagggcgt catctccgac gccgtcaacg cctggcgcga gaacgggcaa 1020
cagtccatcg acgacctgtt cgaccaggtg gagtcgcggt tcgtggcggc ctgggaggac 1080
gacgccgggc tgatgaccta cggcgaggcc gtcgccgagg tgctggagtt cgccgcgagc 1140
gagggcgagc cggctgacat gagcgccgac gagtggcggg ccttcgcggc gcgcgcctcg 1200
ctctactccg ccaaggccaa ggcgaaggag ctgggcttcg acccgggctg ggactgcgag 1260
ctggccaaga cccccgaggg ctactaccag atccggggcg gcatcccgta cgccatcgcc 1320
aagtcgctgg ccgccgcgcc gttcgccgac atcctgtgga tggagaccaa gaccgccgac 1380
ctggccgacg ccaagcagtt cgccgacgct atccacgccg agttccccga ccagatgctg 1440
gcctacaacc tgtcgccgtc gttcaactgg gacaccaccg gcatgaccga cgagcagatg 1500
aagcagttcc ccgaggaact cggcaagatg ggcttcgtct tcaacttcat cacctacggc 1560
ggacaccaga tcgacggcgt ggccgccgag gagttcgcca cctcgctgca acaggacggc 1620
atgctggcgc tggcccgctt gcagcgcaag atgcgtctgg tcgaatcccc ttaccgcaca 1680
ccgcaaacgc tcgtcggtgg gccccgcagc gatgccgcac tggccgcctc gtcgggccgc 1740
accgcgacca ccaaggcgat gggcgagggc tcgacccagc atcagcatct ggtgcagacc 1800
gaggtgccca agaagctgct cgaggagtgg ctggcgatgt ggagcgagaa ctaccacctc 1860
ggcgagaagc tccgcgtgca gttgcggccc cgccgggcgg gttcggacgt gctggaactc 1920
ggcatctacg gcgacggcga cgagcaactg gccaatgtcg tcgtcgaccc gatcaaggac 1980
cggcacggcc gcagcatcct tcaggtgcgc gaccagaaca ccttcgccga aaagctccgg 2040
cagaagcggc tgatgacgtt gatccacctg tggctggtgc accgcttcaa ggccgacgcg 2100
gtgatctacg tgacgccgac cgaggacaac ctgtaccaga cctcgaagat gaagtcgcac 2160
ggcatcttca gcgaggtgta ccaggaggtc ggcgagatca tcgtcgccga ggtgaaccgg 2220
ccccgcatcg ccgaactgct gcagcccgac cgggtggcgc tgcgcaagct gatcaccaaa 2280
gagggttag 2289

<210> SEQ ID NO 15
<211> LENGTH: 234
<212> TYPE: DNA
<213> ORGANISM: Mycobacterium avium

<400> SEQUENCE: 15
ttacttgcca gcaccgcggc gctgcgccgc cagcctgtcc cgtaaagtct tcgggcggat 60
atcgggccag ttctgttcga tgtagtccag gcacgcagcg cgatccgctt cgccgtaaac 120
catctgccag ccggccggaa tgtcggcgaa cgccggccac aggctgtgtt gttcttcgtc 180
gttgaccagg acgaaaaagc tgccattgtc gtcgtcgaac ggattggtac tcac 234

<210> SEQ ID NO 16
<211> LENGTH: 972
<212> TYPE: DNA
<213> ORGANISM: Mycobacterium avium

<400> SEQUENCE: 16
atgcccgccg gctgccacca tggccctatg cgattcggat gtgcccgggc ggtcaacctc 60
ggcctgctgc cggttctggt cgtcgtgctc gccggctgcc tcgccggcgg gcatgcgctg 120
ggaacgcctg actcccaatc gattccggtc gggccatcca cccacaccct gcagtcgggc 180
ggcacgcccc gcagctatca cctgtaccgg ccgcaggggc tgagcgaggc ggcccccctg 240
gtggtgatgc tgcacggcgg ctttggcaac ggcgagcagg ccgagcgcgc ctaccactgg 300

-continued gacgccgagg ccgacgccgg gcatttcctg gtcgcctacc ccgacggcct gggccgcgcc 360
tggaacgccg gaacctgttg cggtgagccg gcacacgccg gcaccgacga cgtcggattc 420
gtcaacgccg tggtcggcgc catcgcggcg cagatcccgg tggatcgtgc ccgcgtctac 480
gtcaccggca tgtcgaacgg cgccatgatg gcgctgcggc tgggctgcca gagcgacacc 540
ctcgccgcga tcgccccggt ggccggcacg ctgctcaccg attgctccgc ggcccggccg 600
gcctcggtgc tgcagatcca cggcaccgcc gacgaccgcg tgccctatgc gggcggaccc 660
ggaaaggcgt tcgcgctcaa cggctccccg cgggtcgacg ggccgtcggt ggaatccgtc 720
aacgccacct ggcgcgccat cgacgcctgc gggccgccca gctcgaccac cgccggcgat 780
gtcaccaccc agaccgccgg ctgcgcggac ggccgcacgg tggagttgat ctcggtggcc 840
gggtgcggcc accaatggcc cggcggggcg cccagccccc tggcggaaaa ggtggccgga 900
attccggcgc cgtcgacggc gctggacgcc accgacacga tctggcaatt cttcgcccgt 960
aatcaccgtt ag 972

<210> SEQ ID NO 17
<211> LENGTH: 702
<212> TYPE: DNA
<213> ORGANISM: Mycobacterium avium

<400> SEQUENCE: 17
ttactgcatg cgcagcacga atcccactcc gcggacggtg tgcagcagcc ggggcccgcc 60
gttggcctcg agcttgcggc gcaggtatcc gatgaacacg tcgacgacgt tggtgtcggc 120
ggcgaagtca tagccccaca ccagctccag cagttgtgcg cgggacagca cggcggtctt 180
gtgctcggcc aggaccgcca gcaggtcgaa ctcccgcttg gtcaaatcga cgtccacgcc 240
gttgacccgg gcgcggcggc cggggatgtc gacctccagc gggcccaccg tgatcgtttc 300
cgacgaggag gtggcggtgg cgccgcggcg gcgcagcagc gccttgaccc gcgcgaccag 360
ctcggccagc acgaacggct tgaccaggta gtcgtcggcc ccggcctcca ggcccgccac 420
ccggtcgtcg accgagctgc gggccgacag cacgcagacg gggacgtcgt tgtccatggc 480
gcgcagcgcg gtgacgacgc tgacgccgtc cagcaccggc atgttgatgt cgagcacgat 540
cgcgtccggg cgtgtctcgg tggcgctgcg cagcgcctcg gcgccgtcga ccgcggtgga 600
cacctcgaat ccggacagtc gcaggccacg ttccagcgac gcgagcacat cggagtcgtc 660
gtcgacgacc aagacccgcg gtgagctagc tgctgtgtcc at 702

<210> SEQ ID NO 18
<211> LENGTH: 417
<212> TYPE: DNA
<213> ORGANISM: Mycobacterium avium

<400> SEQUENCE: 18
gtgagaccag tgccgaccgg caaggttaag tggtacgacg ctgacaaggg cttcggcttc 60
ctgtcccagg aggacggcga agacgtgtac gtccgctcgt cggcgttgcc cgctggcgtc 120
gaggggctca aagcgggcca gcgcgtggaa ttcggcatcg cctccggccg ccgcggaccg 180
caagcgttga gcctcaagct gattgagccg ccgccgagcc tgaccaaggc gcggcgcgag 240
gggcctgccg aacacaagca cagccccgac gagctgcacg gcatggtcga ggacatgatc 300
acgctgctgg aaagcaccgt ccaacccgag ctgcgcaagg gccgctaccc cgaccgcaag 360
accgcgcgcc gggtctccga ggtggtcagg gcggtggccc gcgagctgga cgcctga 417

<210> SEQ ID NO 19
<211> LENGTH: 1122
<212> TYPE: DNA
<213> ORGANISM: Mycobacterium avium

<400> SEQUENCE: 19
tcagacccgg ctcaggtgcg cgcgcagcgc cgagatcaac tcgctggtgg ccaccatgct 60
gtcgccgccg agctggaaca ggttggcgaa gccgtgcgtc agcgaaccca ggtaccgcag 120
gtccaccggg gtgccggcgg cgcgcagcgc ctcggcgtag ctctggccct cgtcgcgtag 180
cgggtcgaag ccggccaccg cgatcagcgc cggggccagg ccggccagcg attcggccag 240
cgccggcgat acccgcgggt ccgtccggtc cagccgcgag ttccgcaggt actgcgattc 300
gaaccagtcg atgtcgcgct tggtcagcag gaagccgcgg gagaacaggc tcagcgaccg 360
ggtccgggcg gtgaagtcgg tgcgcgggta gatcagccac tgcagcaccg gtgccgggcc 420
gcccgcgtcg cgggccagct ggctgacgac ggcggccagg ttgccgccgg cgctgtcgcc 480
gccgaccgcc acccgcccgg ggatcgcgcc cagctcgccg gcatgctcat gcgcccaggt 540
gaaggcggcg tacgcgtcgt cgatggcggc cggcgcggga tgctcgggcg ccagccggta 600
gtcgatcgac agcacgtgga tgccggcgtc gcggcaggtc agccggcaca gcgagtcgtg 660
ggtgtccagg tcgccgatcg accagccgcc gccgtggtag aagaccagca gcggggcctg 720
ggtctcgccg ccggcgggcc gatagtgccg cgccgggatg tcgccggccg ggccgggcag 780
cgccagttcg gcgacgtcga cgtggatctg cgggccgggg aaccccaccg tggactcgtg 840
catctgggcg cgggacagct cggggtcgtc gtcgaccacc aggccgtcga tgccgacggc 900
gcgcagaccg gacagcatca gctgcagggt cgggtcgagc gtgttgccgt cgatgatgac 960
cgagcggccg cgcaccaggc cgcggcgcac ggcggtcggg atccacggga tgaccttgac 1020
cccgacgctg gtgacggcgc cctggatgcg gttggtcagc ggcatcgacc cgcgctgcgc 1080
gccggggtcg acgggtgcgg tgtcggtcag cggcttggtc at 1122

<210> SEQ ID NO 20
<211> LENGTH: 918
<212> TYPE: DNA
<213> ORGANISM: Mycobacterium avium

<400> SEQUENCE: 20
atggatcttc atcagctgga gtgctttatc gcggtcgccg aggaaggcac cttcaccgcc 60
gcggcacagc ggatacatct ggcgcaatct ggtgttagtg cacacattaa ggcgctcgaa 120
cgcgaaatcg ggcagcagct attcgaacgg cggccacgca cggtacggct taccgcggct 180
ggaaacgcgc ttctgccata cgcccgcgca gcactcgatg cgctggccgc aggtcgcgcc 240
tcgatcgacg gactcaccgg tctactacat ggtcgccttg ccatcggcac catcacctcg 300
atctcaccgc gcagcatcga cctccccgag cttctagcag cgtttcacca tgagcacccg 360
ggggtagacc tgtcgctggt tgaggacact gcagcgatgc tcaatcgcca catatccaat 420
ggcgctttag acgtagcttt caccagcctg acggatgagg cagtagccgg cgtgcggatg 480
cgcgagttgc atcgggagcc ggtgatcgcg atctttctac cgtccgatcc gttatctcct 540
tgccggaagc tcacattggc cgacgtggcg gatagaccgc tcatcacgct cccggaggga 600
tcaggcttgc gctggcaact caaccgcgcg ctgcggcggg ccggcgttca agcccacatc 660
gccttcgaag ccggcgatcc cgacgtactc gttgcgctcg ttgcgaaggg gctgggcgtg 720
ggtctcgttc ctcaatcagc cctcgcgcaa agcgatcacg taataggatt gccagtcagc 780
gatcatccgc ccgggcgcct aggcatcatc tggccagaag ggcaagccgc cagcccagcg 840
gctcgtgcct tcgttgaaca cgccaccacg gcgacaacta aacttcggcg accggccgag 900
ctacgccagg atcgctga 918

<210> SEQ ID NO 21
<211> LENGTH: 1530
<212> TYPE: DNA
<213> ORGANISM: Mycobacterium avium

<400> SEQUENCE: 21
ttggccgatg accccggttc aagcttcacc acggtgtgga atgcggtcgt ttcggagctc 60
aacggcgagc ccgtcgccga cggcggagcc gccaaccgca cgactctggt cactcccctc 120
acccctcagc aaagagcgtg gctcaatctg gtccgcccgc tgaccatcgt cgaggggttt 180
gctctgctgt cggtgccgag cagtttcgtg cagaacgaga tcgaacggca cctgcgcgcc 240
ccgatcaccg acgcgctcag ccgccgcctg ggtcagcaga tccagctggg agtccgcatc 300
gctcccccac ccgacgacgt cgaggacgcg cccatcccgc cggccgagcc gttccccgac 360
accgacgccg ccctgtccgc cgacgacggc gccgacggcg agccggtgga gaacggggag 420
ccggtcaccg acacccagcc cggctggccc aactacttca ccgagcggcc gcacgccatc 480
gatcccgccg tcgccgccgg aacgagcctc aaccgccgct acaccttcga cacgttcgtg 540
atcggggcgt ccaaccggtt cgcgcacgcc gccgccctgg ccatcgccga agcaccggcc 600
cgcgcctaca acccgttgtt catctggggc gagtccggtc tgggcaagac gcacctgctg 660
cacgccgccg gcaattacgc gcaacggctc ttccccggca tgcgggtcaa gtacgtctcc 720
accgaggaat tcacgaacga cttcatcaac tcgctgcgcg acgaccgcaa ggtcgccttc 780
aagcgcagct atcgcgacgt cgacgtgctc ctggtcgatg acatccaatt catcgagggc 840
aaggaaggca tccaggagga gttcttccac accttcaaca cgctgcacaa cgccaacaag 900
cagatcgtca tctcctccga ccggccgccc aaacagctgg ccaccctgga agaccggctg 960
cgaacccggt tcgagtgggg cctgatcacc gacgtgcagc cccccgaact cgaaacccgc 1020
atcgcgatcc tgcgcaagaa ggcgcagatg gagcgcctgg cggtgcccga cgacgtgctg 1080
gaactcatcg ccagcagcat cgagcgcaac atccgcgaac tcgagggcgc cctgatccgg 1140
gtcaccgcgt tcgcctcgct gaacaagacc ccgatcgaca agtcgctggc cgagatcgtg 1200
ctgcgcgatt tgattgccga cgccagcacc atgcagatca gcgcggccac catcatggcc 1260
gccaccgccg aatacttcga caccaccgtc gaggaactgc gcgggccggg caagacccgg 1320
gcgctggccc agtcccgcca aatcgcgatg tacctgtgcc gcgagctcac ggatctgtcg 1380
ctgcccaaga tcgggcaggc cttcggccgc gaccacacca cggtgatgta cgcccagcgc 1440
aagatcctgt ccgagatggc cgagcgacgc gaggtgttcg atcacgtcaa ggagctcacc 1500
actcgcattc gtcagcgctc caagcgctga 1530

<210> SEQ ID NO 22
<211> LENGTH: 1200
<212> TYPE: DNA
<213> ORGANISM: Mycobacterium avium

<400> SEQUENCE: 22
atggacgcgg cgacgacaac ggctggcctc agcgacttga agtttcgttt agtgcgggag 60
tctttcgccg acgcggtgtc gtgggtggcc aagagcttgc cgtcgcgacc cgcggtgccg 120

-continued gtgctctccg gggtgctgct gtccggcacc gacgaggggc tcaccatttc cggattcgac 180
tacgaggttt ccgccgaagc acaggtggcg gccgaaatcg cgtctccggg aagtgttttg 240
gtatccgggc ggttgctgtc tgacatcgtt cgggcgctgc ccaacaagcc gatcgacttc 300
tacgtcgacg gcaatcgggt ggcgttgaac tgcggaagcg cccggttctc gctgccgacg 360
atggccgtcg aggattaccc gacgctgccc acgctgcccg aggagaccgg gacgctgccg 420
gccgatctgt tcgccgaggc gatcgggcag gtcgcgatcg cggccggccg cgacgacacc 480
ttgcccatgt tgaccggaat ccgggtcgag atttccgggg acacggtggt tttggccgcc 540
accgaccggt tccggctggc ggttcgcgag ctgacctggt cggcggcctc ccccgacatc 600
gaagcggcgg tcctggtgcc ggccaagacg ctggccgagg cggcgcggac cggcatcgac 660
ggttccgacg tgcggctgtc gctgggggcg ggcgcgggtg tcggcaagga tggcctgctg 720
ggtatcagcg gcaacggcaa gcgcagcacc acccgcctgc tggacgcgga attcccgaag 780
ttccgccagc tgttgccggc tgagcacacg gcggtggcca ccatcaacgt cgccgagctg 840
accgaggcca tcaagctggt ggcgctggtg gccgaccggg gcgcgcaggt gcggatggaa 900
ttcagcgagg ggtcgctgcg gctgtccgcc ggcgccgacg atgtcggccg ggccgaggag 960
gatctggccg tggatttcgc cggcgaaccg ctgacgatcg cgttcaaccc cacgtatctg 1020
accgacggac tgggatcggt gcgctccgaa cgggtgtcgt tcggcttcac caccccgggc 1080
aagcccgcac tgctgcgccc ggcgtccgac gacgacagcc cgccgagcgg cagcgggccg 1140
ttcagcgcgc tgcccaccga ttacgtctac ctgctgatgc ccgtgcggtt gccaggctag 1200

<210> SEQ ID NO 23
<211> LENGTH: 1158
<212> TYPE: DNA
<213> ORGANISM: Mycobacterium avium

<400> SEQUENCE: 23
gtgtacgtcc ggcatttagg actgcgcgac ttccggtcct gggcacacgc cgacctcgaa 60
ctgcagccgg gtcggacggt cttcatcggg tccaacggct tcgggaagac gaatctgctt 120
gaggcgctgt ggtattcgag cacgctgggg tcacaccggg tgggcacgga cgcgccgttg 180
atccgcgccg gcgccgaccg ggcggtggtg tcgaccatcg tggtcaacga cggccgggaa 240
tgtgcggtcg atctggagat cgccgccggc cgggcgaaca aggcgcggct gaaccggtca 300
cccgtgcgca gcacccgcga ggtgctcggc gtgctgcgcg cggtgctgtt cgccccccgag 360 gacctggccc tggtgcgcgg ggatccctcc gagcggcgcc gttacctcga cgacctggcg 420
acgctgcggc gcccggcgat cgccgcggtg cgcgccgact acgacaaggt gttgcggcag 480
cgcaccgcgt tgctcaaatc gctgtccggt gcccgccacc ggggcgaccg cggcgctctg 540
gacaccctcg acgtgtggga cagccggctg gccgaatacg gggcccaatt gatggctgcc 600
cgaatcgatt tggtgaacca gttggcgccg gaggtggaga aggcctatca gctgctggcc 660
ccgggatcgc gggcggcgtc gatcggctac cgatccagcc tgggcgcggc ggcctcggcc 720
gaggtgaacg ccggcgaccg cgactatctg gaggccgcgc tgctggccgg gttggcggcc 780
caccgggacg ccgaactgga acggggcatg tgcctggtcg gcccgcaccg cgacgacctg 840
gagctgtggc tcggtgagca ggtggcgaaa ggctttgcca gccatgggga atcgtggtcg 900
ctggcgctgt ccctgcggct ggccgccttc gagttgctgc gggccgacga aagcgatccg 960
gtgttgctgc tcgacgacgt gttcgccgag ctcgacgccg cccgccgccg ggcactggcc 1020
gcggtggccg aatccgccga acaggtgttg gtcaccgcgg cggtgctcga agacatcccg 1080
acgggctggc aggctcggcg gctcttcgtc gagttgcgcg acaccgacgc gggccgggta 1140
tcggagctgc gcccatga 1158

<210> SEQ ID NO 24
<211> LENGTH: 501
<212> TYPE: DNA
<213> ORGANISM: Mycobacterium avium

<400> SEQUENCE: 24
atggacctgg tgcggcggac cctcgaggag gcccgggccg cggcccgggc acagggaaaa 60
gacgccggcc gcgggcgcgc cgcagcaccc acgccgcgcc gggtggcggg tcagcggcgc 120
agctggtcgg gaccgggacc cgacgctcgc gacccgcaac cgctgggccg gctggcgcgg 180
gacctggcca ggaagcgggg atggtcggcc caggtcgccg agggcaccgt gttggggaac 240
tggacggcgg tggtcggtca ccagatcgcc gaccacgcgg tccccaccgg tctgcgcgac 300
ggtgtgctga gcgtgtccgc cgagtcgaca gcctgggcca cccagttgcg gatgatgcag 360
gcgcaactgt tggccaagat cgccgccgcg gtcggcaacg ggtggtgac ctcgctgaag 420 atcaccggcc cggccgcgcc gtcctggcgc aaaggcccgc ggcacatcgc cgggcgcggg 480
ccgcgcgaca cctatgggta g 501

<210> SEQ ID NO 25
<211> LENGTH: 2034
<212> TYPE: DNA
<213> ORGANISM: Mycobacterium avium

<400> SEQUENCE: 25
gtggctgccc agaagaagaa ggcgcaagac gaatacggtg cttcagcgat caccgtcctg 60
gaaggactgg aggcggtccg caaacgcccc ggcatgtaca tcggctctac cggcgagcga 120
ggtctgcacc acctcatctg ggaggtggtc gacaactcgg tcgacgaagc gatggccggc 180
tacgccgacc gggtcgacgt gcggatcctg gacgacggca gcgttgaggt cgccgacaac 240
ggccgcggca tccccgtcgc gatgcacgcg accggcgccc ccaccgtcga cgtggtgatg 300
acgcagctgc acgccggcgg caagttcggc ggcgaaaaca gcggctacaa cgtcagcggc 360
ggtctgcacg gcgtcggcgt ctcggtggtc aacgcactgt ccacccggct cgaggtcaac 420
atcgcccgcg acggctacga gtggtcgcag tactacgacc acgccgtgcc cggcaccctc 480
aaacagggcg aggccaccaa gcgcaccggc accaccatcc ggttctgggc cgaccccgac 540
atcttcgaga ccaccgagta cgacttcgaa acggtggccc gacggctgca ggaaatggcg 600
ttcctcaaca agggcctgac catcaacctc accgacgagc gggtgaccaa cgaagaggtc 660
gtcgacgagg tggtcagcga caccgccgac gcacccaagt cggcgcagga gaaggcggcg 720
gaatcggctg cgccgcataa ggtcaagcac cgcaccttcc actaccccgg cggcctggtc 780
gacttcgtca aacacatcaa tcgcaccaaa aaccccatcc accagagcat catcgatttc 840
ggtgggaagg gccccggcca cgaggtcgag atcgcgatgc agtggaacgg cggctattcc 900
gaatcggtgc acacgttcgc caacaccatc aacacgcacg agggcggcac ccacgaggag 960
ggcttccgca gcgcgttgac ctccgtggtc aacaagtacg ccaaggacaa gaagctgctc 1020
aaggacaagg accccaacct caccggcgac gacatccgcg agggtttggc cgcggtgatc 1080
tcggtcaagg tgagcgaacc gcagttcgag ggccagacca agaccaaact gggcaacacc 1140
gaggtgaagt cgttcgtgca gaaggtgtgc aacgaacagc tcacccactg gttcgaagcc 1200

-continued

```
aaccccgcag acgccaaagt cattgtcaac aaggcggttt cgtcagcgca ggcgcgcatt   1260

gccgcgcgca aggcgcgaga gttggtgcgc cgcaagagcg caaccgacct gggcgggctg   1320

cccggcaagc tcgccgactg ccggtcgacc gatccgcgca agtcggaatt gtatgtggtc   1380

gagggtgact cggccggcgg ctcggcgaaa agcggccggg actcgatgtt ccaggccatc   1440

cttccgctgc gcggcaagat catcaacgtc gaaaaggccc gcatcgaccg ggttttgaag   1500

aacaccgaag tgcaggcgat catcaccgcg ctgggcaccg ggattcacga cgagttcgac   1560

atcaccaagc tgcgctacca caagatcgtg ttgatggccg acgccgacgt ggacggccag   1620

cacatctcga cgctgttgtt gacgctgctg ttccggttca tgcggccgct gatcgaacac   1680

gggcacgtgt tcttggccca gccaccgctg tacaagctga aatggcagcg cagcgatcca   1740

gagttcgcct actccgaccg cgagcgggac gggctgctcg aggccggcct gaaggccggc   1800

aagaagatca acaaggacga cggtatccag cgctacaagg gtctgggcga gatggacgcc   1860

aaggaattgt gggaaaccac aatggatccc accgtgcggg tgctgcgcca ggtcacgctg   1920

gacgacgccg cggccgccga cgagctgttc tccatcctga tgggcgagga cgtcgacgcg   1980

cgccgcagct tcatcacccg caatgccaaa gacgttcgct tcctagacgt ttaa         2034
```

<210> SEQ ID NO 26
<211> LENGTH: 2520
<212> TYPE: DNA
<213> ORGANISM: Mycobacterium avium

<400> SEQUENCE: 26

```
atgactgaca ccacgctgcc acccggcggt gacgccgccg accgcgtcga accggtcgac     60

atccagcagg agatgcagcg cagctacatc gattacgcga tgagcgtaat cgtcggccgc    120

gcgctgcccg aggtgcgcga cggcctcaag ccggtgcacc gccgggtact ttacgccatg    180

tacgactcgg gtttccgccc ggaccgcagc cacgccaagt cggcgcggtc ggtcgccgag    240

acgatgggca actaccaccc gcacggcgac gcctcgatct acgacaccct ggtgcggatg    300

gcccagccgt ggtcgctgcg ctacccgttg gtcgacgggc agggcaactt tggttcgccg    360

ggcaacgacc cgccggccgc gatgcggtac accgaggcgc ggctgacccc gctggccatg    420

gagatgctgc gcgaaatcga cgaggagaca gtcgatttca ttcccaacta cgacggccgg    480

gtgcaagagc cgacggtgct gcccagccgg ttccccaacc tgctggccaa cgggtcgggg    540

ggcatcgcgg tcggcatggc cacgaacatc ccgccgcaca acctcggcga gctcgccgag    600

gcggtgttct gggcgctgga caattacgag gccgacgaag aggccaccct ggccgccgtg    660

atggaacggg tgaaaggacc cgacttcccg acctccggcc tgatcgtcgg cacgcagggc    720

atcgccgacg cctacaagac cggccgcggt tccatccgga tgcgcggagt cgttgaggtg    780

gaagaggatt cgcgcggccg cacctcgctg gtcatcaccg agttgccgta tcaggtcaac    840

cacgacaact tcatcacctc gatcgccgag caggtgcgcg acggcaagct ggccggcatc    900

tccaatatcg aggaccaatc cagcgaccgg gtcgggctgc gcatcgtcat cgagctcaag    960

cgcgacgccg tcgccaaggt ggtgctgaac aacctctaca agcacaccca gctgcagacc   1020

agcttcggcg ccaacatgct ggccatcgtc gacggggtgc cgcgcaccct gcggctcgac   1080

cagctgatcc gccactacgt cgaccaccaa ctcgacgtca tcgtccggcg caccacctac   1140

cggttgcgca aggccaacga gcgggcccac atcctgcgcg gtctggtcaa ggcgctcgat   1200

gcgctcgacg aggtcatcgc cctgatccgg gcgtcggaaa ccgtcgacat cgcgcggcag   1260

ggcttgatcg agctgctcga catcgacgag atccaggcgc aggcgatcct ggacatgcag   1320
```

-continued ctgcgccggc tggccgcgct ggagcggcag cgcatcatcg acgacctggc caagatcgag 1380
gccgagatcg ccgacctgga ggacatcctg gccaagccgg aacggcagcg cggcatcgtg 1440
cgcgacgagc tcgccgagat cgtcgaaaag cacggcgacg cgcggcgcac ccggatcgtg 1500
gccgccgacg gcgacgttag cgacgaggat ctgatcgctc gcgaggacgt cgtcgtcacc 1560
atcaccgaga ccggctacgc caagcgcacc aagaccgacc tgtaccgcag ccagaagcgc 1620
ggcggcaagg gcgtgcaggg cgccggcctc aaccaggacg acatcgtgcg gcacttcttc 1680
gtgtgctcga cgcacgactg gatcctgttc ttcaccaccc agggccgggt ctaccgcgcc 1740
aaggcctacg aactgcccga ggcgtcccgc accgcccgcg gtcagcacgt ggccaacctg 1800
ctggcgttcc agcccgagga gcggatcgct caggtgatcc agatccggag ctatgaggac 1860
gctccctacc tggtgctggc cacccgcaac ggcctggtga agaagaccaa gctgaccgac 1920
ttcgactcga accgctcggg cggcatcgtg gcgatcaacc tgcgcgacaa cgacgaactc 1980
gtgggcgcgg tgttgtgctc ggccgaggac gatctgctgc tggtgtcggc caacggccag 2040
tccatccggt tctcggcgac cgacgaggcg ctgcgcccga tgggccgcgc cacctccggt 2100
gtgcagggca tgcgcttcaa cgccgacgac tacctgctgt cgctcaacgt ggtccgcgag 2160
ggcacctacc tgctggtggc gacgtccggc gggtacgcca agcgcaccgc gatcgaggag 2220
tatccggtgc agggccgcgg cggcaagggc gtgctgaccg tgatgtatga ccgccgccgt 2280
ggcaggctgg tgggtgcgct gattgtggac gaggacagcg agctgtacgc gatcacctcc 2340
ggcggcggtg tcatccgcac cgcggcgggc caggtccgta aggcgggacg gcagaccaag 2400
ggcgtccggc tgatgaatct gggtgagggc gacacgctgc tggccatcgc tcgcaacgcc 2460
gaggaagccg cggacgaggc cgtcgacgag agcgacggtg ccgcggggtc ggacggctag 2520

<210> SEQ ID NO 27
<211> LENGTH: 852
<212> TYPE: DNA
<213> ORGANISM: Mycobacterium avium

<400> SEQUENCE: 27
gtgagttcac cgaacgagcc gggcgcaccc aagaaggggg agacccccaa cggggacggt 60
tcggcagagc gggccggggt gcggcgggcg acaccgccgg cgccgggtgg ccgcgccccc 120
gaggccggcg acggaccgcc gtggcagcgc ggcagcaccc ggccccagca gcccccgccg 180
cgccagaacg agccgcccac cgagaagcgg gccgacggcg gcggggccga ggcccggctg 240
aaccgcttca tctcgggcac cgcgtcgcac gccaaggagc cggagcgcgg tgaggggccc 300
cccgccgagg cctacgccag cgaactgccc gacctgtcgg ggccggtgcc gcgcggccca 360
caccgcaagc cggccgccga gcgcggtgcc gagacgaccg gcgggcaagg cggtggccgt 420
ccggtgagcg gcgagagccg cgagggccgg gacaaccggg accgggtgca ggtgtcgcgg 480
cgcacccgcg ggccggttcg cgccagcatg cagatccgcc ggatcgaccc gtggagcacc 540
ctgaaggtgt cgctgctgct ctcggtggcg ctattcttcg tctggatgat cgccgtcgcg 600
ttcctctacc tggtgctcgg tggcatgggc gtgtggtcga agttgaacag caacgtcggg 660
gacctgctga acaacaccag cggcagcagc ggcgaattgg tgtccagcgg caccattttc 720
ggcggcgccg tgctgatcgg cctggtcaac atcgtgctgt tgaccgcgat ggcgaccatc 780
gcggcgttca tctacaacct ggccaccgat ctgatcggcg gcatcgaggt caccctggcc 840
gatcgcgact ag 852

<210> SEQ ID NO 28
<211> LENGTH: 579
<212> TYPE: DNA
<213> ORGANISM: Mycobacterium avium

<400> SEQUENCE: 28

```
ctaggctcca caaatcgaat ccctctcccc gcccgggcgg tacgacgcgc cgaggaagcg     60
gtgcaccagg gcgcgctcgg cggccgggtc cttgagcggc cagcccccata acgccaggaa   120
gacgcggatc agccactgcg ccgccagcgg gtcgtcgtgg ccgggcccga gcatctcggc    180
ggccagggcc gtcaccgtgg gcgagttgat cacccagtcg ctgaccgggg ccgcgtggat    240
cgaccgcatc agctgagcca gcggatcgga gcgcaaccgt tccagcgcca tgatcgtggc    300
ggtcaccacc cgctcggggc cgcgcaggtc tttgatggcc tcccgcgtgg tgtcgacgat    360
gcgggcggcc tggataccga cgacggcatc gcggatcgtc gccttgccgc cggcgtgccg    420
gtagatggtc gccggtgaac agtgcacccg ggccgccagc gcctcgatcg tgaacccgtc    480
gtagccgcgg cgcgcgatga ggtcggcggc cgcggcgtag atccgctcgg cggccgcgct    540
gcgccgatcc cggcccacca accagtcgtc ccgcgccat                           579
```

<210> SEQ ID NO 29
<211> LENGTH: 1326
<212> TYPE: DNA
<213> ORGANISM: Mycobacterium avium

<400> SEQUENCE: 29

```
ctgctcgcga cgggtcaccc gcacccgcag gcgccgtccc cggccgtcgt cgctcctcaa     60
cttcgccgcg gcccgttgac gccgcgagac ggcgcgtcga gcctgaaacg catggcggtg    120
ttggacagcg cgacccggtt cttcggcagc gaggcgatac aggatcccta cccgctgtat    180
gagcgcatgc acgccgaggc gccgatgcac cggatcggcg actccgtctt ctacgccgtg    240
tgcgggtggg acgcggtgca cgaggccatc gagcgggtcg aggacttctc gtccaacctc    300
accgcgacga tggtcttcca cgaggacggc accgtcaccc cgttcgacat gggcgcgccg    360
ggcgccccga tgcacgcgct ggccaccgcc gacgaccccg tgcacgcggt gcaccgcaag    420
atcctgctgc cgcacctttc ggcgaagcga atccggatca tcgaggagtt cgccacccag    480
accgccgacc ggctgtggga cgagaacctg tccgacggcc ggatcgagtg gatgagcgcc    540
atcgccaacc ggttgcccat gatggtggtc tgccggctgc tgggtctgcc cgatgacgat    600
gtcgacaaac tcatccggct cggctacgcc accaccacac tgctggacgg gatcgtcgcc    660
cccgaacagc tcgagcaggc cggcatggcc gccatcgaac tgtccggcta cgtgctggag    720
catttcgaaa aggcaagcga gaagccggaa tccagcctga tggccgatct tgcggcgcgc    780
tgcgccgccg gcgaactcga gcagctgccg gcgctgggaa tcatgctcac gctgttcagc    840
gcggccggcg aatcgaccgc gtcgctgctg ggcagcgcgg cctggatcct ggccgaccgg    900
ccggcgatcc aacggcagct tcgcgaaaac ccggagttgc taagcacttt catcgaagag    960
acgctgcgct tcgaggcgcc gtttcggggt cactaccgcc acgtgtggcg cgacaccacg   1020
ctgggcggga tcgagctgcc cgagggcgca cacctgctgc tgatgtgggg agcggccaac   1080
cgcgacccga cacatttcaa ggatcccaac gagtttcggc tcgaccgcgc ggccgccaag   1140
agccacctga gcttcggcaa gggcgtccac ttctgcgtcg gtgccgcgct ggcccggctg   1200
gaagcccaca tcgtgttgcg ccggctgctc gagcgcacca gctggatcga cgcgaccgac   1260
gtcggggatt ggctgcccag catcctggtc cggcgccggg aacggctggg gttggccgtg   1320
```

cgctga 1326

<210> SEQ ID NO 30
<211> LENGTH: 435
<212> TYPE: DNA
<213> ORGANISM: Mycobacterium avium

<400> SEQUENCE: 30
ctacggccgc ggttgcacgt cgacgctcgg cggccgcgac tgcggctcct gcggcttctc 60
gcgcaccgag cgccgcacga tgctgaacgc ggcggcgccc ccggcgagaa cggcgacggc 120
gacaccggcg atgacccacg ggcgcttgcc ccgtcgctgc gcgcgccgcg cgtcctgcag 180
cgcctggggc aggccggtga ccacctcctg agcggcggcc agttcctggg cgagggtctc 240
ctgggccgcg gcgaggtctc gggccaggcg cccctcccgg taccggcgcc gcagctgctc 300
ggccgtcgac cgcgcggact gcacgctcag gccggcgact ccccgggtga ggtccagcgg 360
tcccagtgtc gagtaggtca ggccgcgggc cagtcgctct cgcggggtca gccggtcttc 420
cgccttagcg cgcat 435

<210> SEQ ID NO 31
<211> LENGTH: 549
<212> TYPE: DNA
<213> ORGANISM: Mycobacterium avium

<400> SEQUENCE: 31
gtggcagact ctgatgccgt gactaacagc ccctttcaga ctgctaccgc cacgctgcac 60
accaaccgcg gtgacatcaa ggtcgccctg ttcggaaacc acgcgcccaa gaccgtggcc 120
aacttcgtcg gcctggccca gggcaccaag gagtactcga cccagaacgc gtcgggcggc 180
tcctcgggcc cgttctacga cggcgcggtg ttccaccggg tgatccgggg cttcatgatc 240
cagggcggcg acccgaccgg caccggccgc ggcggtccgg ggtacaagtt cgccgacgag 300
ttccaccccg agctgcagtt cgaccggccg tacctgctgg cgatggccaa cgcggggccg 360
ggcaccaacg gctcgcagtt cctcatcacc gtggacaaga ccccgcacct gaaccggcgg 420
cacaccatct tcggcgaggt cgtcgacccg gagtcgcaga aggtcgtcga cgcgatctcg 480
acgaccagca ccgacggcaa cgaccgcccg tccgagccgg tggtgatcga gtcgatcacc 540
atctcgtag 549

<210> SEQ ID NO 32
<211> LENGTH: 426
<212> TYPE: DNA
<213> ORGANISM: Mycobacterium avium

<400> SEQUENCE: 32
tcagcgctgt cgcgggcccg cgtaaccggc ggcggtgagc gcgtcgagca cctggagcgg 60
gtccgccccg agatcccagc gggacagcac caccaggtct ccgtcggcgc tttccacctc 120
gagcaaccgc accttgcgcc cgtagcggcg gaactcgatg atccggatga tcttgatgtc 180
ggggcgttgt aatacctgcg tccgatacca gccgcggacg gccagcccgt cgggtgtgat 240
tgccagcttc gggcgcgcgc gccacgacat ccccgcaaac acgagcagac ccgccgcggc 300
aacgccagcc agaacacgcc ccggcgggtc tgtgaccacg gtcacagccg cgatagccat 360
cagaacgccc gcaactccac aaccagcgat tcccgccgga tgcggctccc accgtgtttg 420
ctgcat 426

<210> SEQ ID NO 33
<211> LENGTH: 282
<212> TYPE: DNA
<213> ORGANISM: Mycobacterium avium

<400> SEQUENCE: 33
tcagtgccag cgcatcgtga gcaacaaacc ggtgatcatg aaagcgaacg cgattgcgta 60
gttccacggc cccaattggg ccatccaatt gagggcggtc ggcgcctggc tgcccaccgc 120
ggccagttgg aagaccatca gccacaccaa tccgatcagc atcagcccga tgaacagcgc 180
gacgaaccac acgctggacg gtcccacctt gaccttcacc ggcgtgcggc tgaccgcgct 240
gacggtgaag tcgttctttt tgcggacctt ggacttgggc at 282

<210> SEQ ID NO 34
<211> LENGTH: 744
<212> TYPE: DNA
<213> ORGANISM: Mycobacterium avium

<400> SEQUENCE: 34
atggtccaga cgcgccagtc gccatggcgc ttcggcgtcc cgctggtctg cctgctggcc 60
ggattgctgc tcgccgccac gcacggcgtg tccggcggcg ccgagatacg ccgcagcgac 120
gcaccccggc tggtggacct ggtgcgcgag acgcaggcgt cggtgaaccg gctcagtgcc 180
cagcgcgaac agctcgccgc caagatcgac gccgcgcacg gccgctcgtc ggatgccgcg 240
ctggccgcga tgctgcgccg ctccgcgcag ctcgccggcg aggccgggat gagcccggtg 300
cacgggccgg gcctggtggt caccctgcag gatgcgcagc gcgacgccaa cggccgcttc 360
ccccgcgacg cgtcgcccga cgacctggtg gtgcaccagc aggacatcca ggccgtgctc 420
aacgcactgt ggagcgccgg cgccgaggcg atccagatgc aggaccagcg gatcatcgcc 480
acgtcggtgc cccgctgcgt cggcaacacg ctgctgctca acgggcgcac ctacagcccg 540
ccctacacga tcaccgcgat cggcaacgcc gccgccatgc aggccgccct ggccgcggct 600
cccctggtga cgctgtacaa gcagtacgcg gtccggttcg gcctgggcta tcaggaagag 660
gtccgctccg atgtgcaggt ggtcggccac ttcgagcccg accggctgca tttcgcccag 720
cccaacggcc cgatcggcta ctaa 744

<210> SEQ ID NO 35
<211> LENGTH: 687
<212> TYPE: DNA
<213> ORGANISM: Mycobacterium avium

<400> SEQUENCE: 35
atgcggatcc tggttgtcga caactacgac agcttcgtgt tcaacctggt gcagtacctc 60
gggcaactgg gtgtggacgc cgacgtctgg cgcaacgacg acagccggct cgccgaccac 120
aacgccgagg cccgccggtt cgacggggtg ctgctcagtc ccgggccggg cacccccgag 180
cgcgcgggcg cttccatcgc gatggtgcgc gcctgcgccg ccgagcacac cccgctgctg 240
ggggtctgcc tgggccacca ggccatcggc gtggcattcg gcgccaccgt ggaccgcgct 300
ccggaactgc tgcacggcaa gaccagcagc gtgcgccaca cgaatgccgg tgtgctgcaa 360
gggcttccgg accccttcac ggccacccgg taccactcgc tgaccatcct gcccgagtcg 420
ctgccgccgg tgctcgaggt caccgctcac accgacagcg gtgtgatcat gggcgtgcgc 480
cacacgcagt taccgatcca cggcgtccag ttccacccgg agtcgatcct gaccgagggt 540
ggtcatcgca tgctggcgaa ctggctcacc gaatgcggct gggtgcgcga cgacaccctg 600
gtgcgccggc tggaaaacga cgtccacgcc gcggtgcgac cgtatctccc ggccgatccg 660
gccgctactg accgaacttc agcgtga 687

<210> SEQ ID NO 36
<211> LENGTH: 1881
<212> TYPE: DNA
<213> ORGANISM: Mycobacterium avium

<400> SEQUENCE: 36
ctactgaccg aacttcagcg tgatgatccc gtcccggttg accccggccc cggccggcgg 60
gttctgatac accacccggt gggactgggc gccgccggcg tcgacgtcgg gacccttgtc 120
caggatcccc gtccagccca gcgcccgtag ccgcggttcg gcgtcggtcc aaaacatccc 180
ggacaggtcg ggcatgatga actgattgcc cttggacacc tgcagttcga tcaccgaatc 240
caccggaacc gtttgtccct tgggcggatt ggtgccgatc acctcgccgg ccgggcgggg 300
gctgtccacc tgcacctggg tgatcttggt gaagccgtag acggtcaggt tcttctgcgc 360
gatgtcgacg gtttgcccgg cgatgtcggg cacctgcttg gtctccggcc ccgagccgac 420
gatgagggtg atgacgttgg tgatcgccga cgtctggttg gccggcgggt tggtcccgat 480
caccttgccc aacaactcgg gtgtggacgg cgagttcgcc tgcttgaact tgctgaaccc 540
ggcggccttg agcttggtga ccgcgtcgga gtagctcagc gacgagacgt cgggcacctc 600
gcgctgctcc ggcccggtgg agacgttgat ggtgatctcg tcgcccgcgc tgaccgacgc 660
gttggcgccg gggtcggtgc cgatgacgtg gtcgggcggg atggccgagt ccggcttctg 720
cagggtgcgg gtcttgaagc cgcggttctg cagcgccgca atggcatcgg cggacacctg 780
cccgcgcacg tcgggcacct ggacgtcgcg ggcgccgccg ccgaaggtgt tgaacgcgat 840
gacgacgatg atggtcagga ccgccagcgc ggccaccgcc acgatccaac ggcccaccga 900
acccaccgtg cggtcctcgc cgctgtccgc gagcacctgg cgaggcagcg gatcggtgcg 960
tgacggaccc gcggccccgg caccggacga caacagcgag ctgcgctcgg cgtcggtgag 1020
aacctttggc gcttccggct tttcgccgtt gtgcacccgg accagatcgg cgcgcatttc 1080
gaccgcggtc tgatagcggt tgtccgggtt tttggccagc gccttgagca cgacggcgtc 1140
gaggtcggcg gagatgcctt cgtgccgctg cgacggcggc accgggtctt cgcggacatg 1200
ctggtaggcc accgccaccg gcgagtcgcc ggtgaaaggc ggctcgccag tgaggatttc 1260
gtacagcacg cagcccagcg agtagacgtc cgagcgcgcg tcgacggcgt cgccgcgggc 1320
ctgctcgggc gagaggtact gtgcggttcc gatcaccgcc gcggtctggg tgacgctgtt 1380
gccgctgtcg gcgattgcgc gggcgatgcc gaagtccatc accttgacgg cattggtggt 1440
gctgatcatg atgttcgccg gcttgacgtc gcggtggatg atgccgttct ggtggctgaa 1500
gttcagcgcc tggcaggcgt cggcgatgat ctcgatggcc cgccgcggcg gcagcggccc 1560
gtcggtgtgc acgatgtcgc gcagcgtcac gccgtcgacg tactccatga cgatgtaggg 1620
cagcggcccg gagggcgtct ccgcctcgcc ggtgtcgtag acggcgacga tggacgggtg 1680
gttgagcgcg gcggcgtttt gcgcctcgcg ccggaagcgc aggtagaaac tgggatcgcg 1740
ggccaggtcc gcgcgcagca ccttgaccgc gacgtcgcgg tgcagccgga cgtcacgggc 1800
caggtgaacc tcggacatgc cgccgaagcc gaggatctcg ccgagttcgt agcggtcgga 1860
caggtgttgc ggggtggtca t 1881

<210> SEQ ID NO 37

-continued

```
<211> LENGTH: 510
<212> TYPE: DNA
<213> ORGANISM: Mycobacterium avium

<400> SEQUENCE: 37

tcattgcgat gtccagtgtc gggcgggtcc gtcgcggaat ccagacgccc caattgtgcc      60

gtcatccggc cagtccagcc gcaggcccgg gtgggccccg gagccgctcg gcgtcttggt     120

cggcggcggc gccgaggcgg gcggggttcc ggtgtcggtg accgtcgggg gctgttgctg     180

ctggtccgcg cgggagttga tgacgatgag caccgcgatg atgatcgcca gcgcgcccag     240

caccccggcg gcccacagca gcgcccgctg gccggacgag aaggtgcgcc gggccggggg     300

cgggcggtgg ccgccggtgg ccggccgggt ccgccgcggc gcggcggtcc gcccggagga     360

cacggctgcc gcccgggtgg tggggctgga cggaatggcc gccggtgacg cccgcccggg     420

cggcggggac tggctcggcc gcggcggccg gcgaccggcg cgcaccgcgg cgacggcgtc     480

ggcgaacggc cccccgctgc ggtagcgcat                                      510


<210> SEQ ID NO 38
<211> LENGTH: 762
<212> TYPE: DNA
<213> ORGANISM: Mycobacterium avium

<400> SEQUENCE: 38

tcacagggtg atctcgatga gctcgcgcac gttgggtggc agctccgcgg gcagcggcgg      60

cggaggctcc ttgatgtgtt tcatcgccac cgtcagcgcc ccatccccgc tgaacggccg     120

cttgcccgaa accacctcgt agccaacaac tcccagcgag tacacgtcgc tggcgggggt     180

ggcgtcgtga cccagcgcct gctcgggcgc gatgtattgg gcggtgccca tcaccattcc     240

ggtctgggtc accggcgcgg cgtcgacggc cttggcgata ccgaagtcgg tgatcttcac     300

ctgccccgtc ggggtgatca ggatgttgcc cggtttgacg tcgcggtgca ccaggccggc     360

ggcgtgcgcg acctgcaggg cgcggccggt ctgctcgagc atgtccagcg cgtgccgcag     420

cgacagccgg ccggtccgct tgagcaccga gttcagcggc tcaccgttga ccagttccat     480

caccagatac gcggtgcggc cctcgccgtc cagctggctc tcgccgtagt cgtgcacagc     540

cgcgatgccc gggtggttga gcatcgccgt ggtgcgcgcc tcggcgcgga accgctcgat     600

gaactcgggg tcctgggaga actcctgttt gagcaccttg accgcgacgc gccggcccag     660

ccggttgtcg accgcctccc agacctgacc catgccgccg gtggcgatca ggcgctgcag     720

gcggtacctg ccagacagcg tcacaccaac tcgcgggctc at                        762
```

VACCINE CANDIDATES AGAINST JOHNE'S DISEASE

CROSS-REFERENCE TO RELATED APPLICATIONS

This application is a continuation of U.S. patent application Ser. No. 14/268,793, filed May 2, 2014, which is a continuation application of U.S. patent application Ser. No. 11/636,025, filed Dec. 8, 2006, and issued as U.S. Pat. No. 8,758,773 on Jun. 24, 2014 which claims priority to U.S. Provisional Patent Application Ser. No. 60/749,128, filed Dec. 9, 2005, each of which are incorporated herein in their entirety.

GOVERNMENT INTERESTS

This invention was made with government support under 04-CRHF-0-6055, 2004-35204-14209, and 2004-35605-14243 awarded by the USDA/NIFA. The government has certain rights in the invention.

FIELD OF THE INVENTION

This invention relates to nucleic acid sequences from *Mycobacterium avium* subspecies *paratuberculosis* (hereinafter referred to as *Mycobacterium paratuberculosis* or *M. paratuberculosis*), the products encoded by those sequences, compositions containing those sequences and products, and compositions and methods for prevention and treatment of *M. paratuberculosis* infection.

BACKGROUND OF THE INVENTION

*Mycobacterium paratuberculosis* causes Johne's disease (*paratuberculosis*) in dairy cattle. The disease is characterized by chronic diarrhea, weight loss, and malnutrition, resulting in estimated losses of $220 million per year in the USA alone. World-wide, the prevalence of the disease can range from as low as 3-4% of the examined herds in regions with low incidence (such as England), to high levels of 50% of the herds in some areas within the USA (Wisconsin and Alabama). Cows infected with Johne's disease are known to secrete *Mycobacterium paratuberculosis* in their milk. In humans, *M. paratuberculosis* bacilli have been found in tissues examined from Crohn's disease patients indicating possible zoonotic transmission from infected dairy products to humans.

Unfortunately, the virulence mechanisms controlling *M. paratuberculosis* persistence inside the host are poorly understood, and the key steps for establishing the presence of *paratuberculosis* are elusive. Mechanisms responsible for invasion and persistence of *M. paratuberculosis* inside the intestine remain undefined on a molecular level (Valentin-Weigand and Goethe, 1999, *Microbes & Infection* 1: 1121-1127). Both live and dead bacilli are observed in sub-epithelial macrophages after uptake. Once inside the macrophages, *M. paratuberculosis* survive and proliferate inside the phagosomes using unknown mechanisms.

*M. paratuberculosis* is closely related to *Mycobacterium avium* subspecies *avium* (hereinafter referred to as *Mycobacterium avium* or *M. avium*), which is a persistent health problem for immunocompromised humans, particularly HIV-positive individuals. Limited tools are available to researchers to definitively identify *M. paratuberculosis* and to distinguish it from *M. avium*. Existing methods are subject to high cross-reactivity, poor sensitivity, specificity, and predictive value. This dearth of knowledge translates into a lack of suitable vaccines for prevention and treatment of Johne's disease in animals, and of Crohn's disease in humans.

The current challenge in screening *M. paratuberculosis* is to identify those targets that are essential for survival of the bacilli during infection. Recently, random transposon mutagenesis-based protocols were employed for functional analysis of a large number of genes in *M. paratuberculosis* (Harris et al., 1999, *FEMS Microbiology Letters* 175: 21-26; Cavaignac et al., 2000, *Archives of Microbiology* 173: 229-231). When *M. paratuberculosis* was used as a target for mutagenesis, the libraries were screened to identify auxotrophs or genes responsible for survival under in vitro conditions. In these reports, six auxotrophs and two genes responsible for cell wall biosynthesis were identified (Harris et al., 1999; Cavaignac et al., 2000). So far, none of these libraries have been screened for virulence determinants.

Many clinical methods for detecting and identifying *Mycobacterium* species in samples require analysis of the bacterium's physical characteristics (e.g., acid-fast staining and microscopic detection of bacilli), physiological characteristics (e.g., growth on defined media) or biochemical characteristics (e.g., membrane lipid composition). These methods require relatively high concentrations of bacteria in the sample to be detected, may be subjective depending on the clinical technician's experience and expertise, and are time-consuming. Because *Mycobacterium* species are often difficult to grow in vitro and may take weeks to reach a useful density in culture, these methods can also result in delayed patient treatment and costs associated with isolating an infected individual until the diagnosis is completed.

More recently, assays that detect the presence of nucleic acid derived from bacteria in the sample have been preferred because of the sensitivity and relative speed of the assays. In particular, assays that use in vitro nucleic acid amplification of nucleic acids present in a clinical sample can provide increased sensitivity and specificity of detection. Such assays, however, can be limited to detecting one or a few *Mycobacterium* species depending on the sequences amplified and/or detected.

The genome sequences of both *M. avium* (Institute for Genomic Research) and of *M. paratuberculosis* (Li et al., 2005, *Proc. Natl. Acad. Sci. USA* 102: 12344-12349; GenBank accession No. AE016958) are currently available. It would be useful to analyze these genomes to provide a higher resolution analysis of *M. avium* subspecies genomes. A better understanding of the virulence mechanisms and pathogenesis of *M. paratuberculosis* is required to develop more effective vaccine and chemotherapies directed against *M. paratuberculosis.*

In view of the problems with bacterial specificity, the present inventors have focused their attention on identification of putative virulence factors that may contribute to the pathogenicity of *M. paratuberculosis*. This information could be used to design vaccines against pathogenic subspecies of *M. avium*. Such vaccines can be used for prevention and treatment of Johne's disease in animals or Crohn's disease in humans.

SUMMARY OF THE INVENTION

This invention relates to immunogenic compositions and methods for prevention and treatment of Johne's disease in animals or Crohn's disease in humans.

This invention provides a vaccine composition that includes an antigen selected from *Mycobacterium* strain-specific polynucleotide sequences and their products. In one embodiment, the antigen includes at least one of the gcpE (SEQ ID NO:7), pstA (SEQ ID NO:8), kdpC (SEQ ID NO:9), papA2(SEQ ID NO:10), impA(SEQ ID NO:11), umaA1(SEQ ID NO:12), fabG2_2(SEQ ID NO:13), aceAB (SEQ ID NO:14), mbtH2(SEQ ID NO:15), lpqP(SEQ ID NO:16), map0834c(SEQ ID NO:17), cspB(SEQ ID NO:18), lipN(SEQ ID NO:19), or map1634 (SEQ ID NO:20) genes of *M. paratuberculosis*, or homologs of these genes. In another aspect, the invention is directed to an antigen that includes at least one of the genomic islands MAP-1 (SEQ ID NO:21), MAP-2 (SEQ ID NO:22), MAP-3 (SEQ ID NO:23), MAP-4 (SEQ ID NO:24), MAP-5 (SEQ ID NO:25), MAP-6 (SEQ ID NO:26), MAP-7 (SEQ ID NO:27), MAP-8 (SEQ ID NO:28), MAP-9 (SEQ ID NO:29), MAP-10 (SEQ ID NO:30), MAP-11 (SEQ ID NO:31), MAP-12 (SEQ ID NO:32), MAP-13 (SEQ ID NO:33), MAP-14 (SEQ ID NO:34), MAP-15 (SEQ ID NO:35), MAP-16 (SEQ ID NO:36), MAP-17 (SEQ ID NO:37), or MAP-18 (SEQ ID NO:38) of *M. paratuberculosis*, or homologs of these genomic islands. In addition to the antigens, the vaccine composition includes a pharmaceutically acceptable carrier. The vaccine composition may optionally include an adjuvant.

This invention provides an immunological composition that includes a eukaryotic expression vector that encodes an antigen. In one aspect, the eukaryotic expression vector includes at least one of the gcpE, pstA, kdpC, papA2, impA, umaA1, fabG2_2, aceAB, mbtH2, lpqP, map0834c, cspB, lipN, or map1634 genes of *M. paratuberculosis* or their homologs. In another aspect, the invention is directed to a eukaryotic expression vector that includes at least one of the genomic islands MAP-1, MAP-2, MAP-3, MAP-4, MAP-5, MAP-6, MAP-7, MAP-8, MAP-9, MAP-10, MAP-11, MAP-12, MAP-13, MAP-14, MAP-15, MAP-16, MAP-17, or MAP-18 of *M. paratuberculosis*, or their homologs. In addition to the eukaryotic expression vector, the immunological composition includes a pharmaceutically acceptable carrier. The immunological composition may optionally include an adjuvant.

This invention provides a method of treating Johne's disease in mammals. The method includes administering to a mammal a vaccine composition against *M. paratuberculosis*. The vaccine composition includes an antigen selected from the group of gcpE, pstA, kdpC, papA2, impA, umaA1, fabG2_2, aceAB, mbtH2, lpqP, map0834c, cspB, lipN, or map1634 genes of *M. paratuberculosis*, or their homologs, or at least one of the genomic islands MAP-1, MAP-2, MAP-3, MAP-4, MAP-5, MAP-6, MAP-7, MAP-8, MAP-9, MAP-10, MAP-11, MAP-12, MAP-13, MAP-14, MAP-15, MAP-16, MAP-17, or MAP-18 of *M. paratuberculosis*, or their homologs. In addition to the antigen, the vaccine composition includes a pharmaceutically acceptable carrier. The vaccine composition may optionally include an adjuvant.

In another aspect, this invention provides a method of treating Johne's disease, which includes administering to a mammal an immunological composition comprising a vector expressing a nucleotide sequence that includes at least one of the gcpE, pstA, kdpC, papA2, impA, umaA1, fabG2_2, aceAB, mbtH2, lpqP, map0834c, cspB, lipN, or map 1634 genes of *M. paratuberculosis*, or their homologs, or at least one of the genomic islands MAP-1, MAP-2, MAP-3, MAP-4, MAP-5, MAP-6, MAP-7, MAP-8, MAP-9, MAP-10, MAP-11, MAP-12, MAP-13, MAP-14, MAP-15, MAP-16, MAP-17, or MAP-18 of *M. paratuberculosis*, or their homologs. In addition to the expression vector, the immunological composition includes a pharmaceutically acceptable carrier. The immunological composition may optionally include an adjuvant.

DETAILED DESCRIPTION OF THE INVENTION

Figure 1:
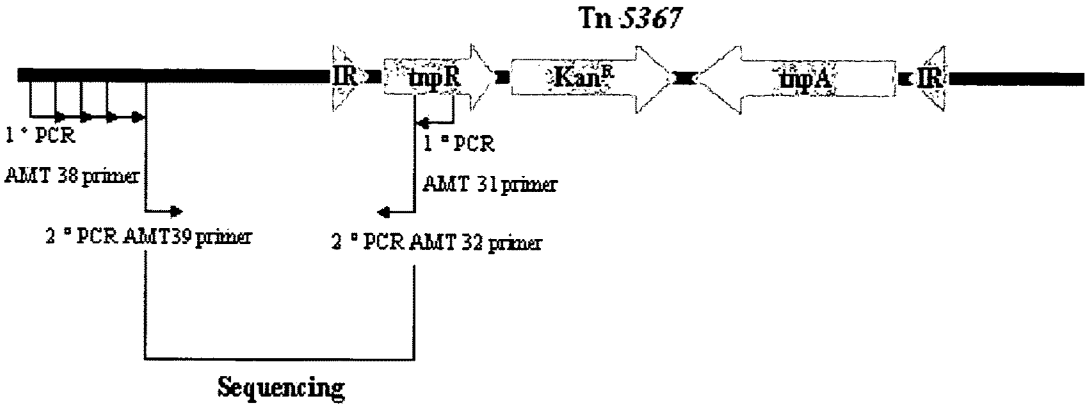
FIG. 1 is a schematic representation of the transposon Tn5367 from strain ATCC19698 used for insertion mutagenesis of *M. paratuberculosis.*

The present invention provides genomic identifiers for mycobacterial species. These genomic identifiers can be used as targets for developments of vaccines and drugs against Johne's disease.

1. General Overview

The practice of the present invention employs, unless otherwise indicated, conventional techniques of molecular biology (including recombinant techniques), microbiology, cell biology, biochemistry, immunology, protein kinetics, and mass spectroscopy, which are within the skill of art. Such techniques are explained fully in the literature, such as Sambrook et al., 2000, *Molecular Cloning: A Laboratory Manual*, third edition, Cold Spring Harbor Laboratory Press; *Current Protocols in Molecular Biology* Volumes 1-3, John Wiley & Sons, Inc.; Kriegler, 1990, *Gene Transfer and Expression: A Laboratory Manual*, Stockton Press, New York; Dieffenbach et al., 1995, *PCR Primer: A Laboratory Manual*, Cold Spring Harbor Laboratory Press, each of which is incorporated herein by reference in its entirety. Procedures employing commercially available assay kits and reagents typically are used according to manufacturer-defined protocols unless otherwise noted.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications.

2. Definitions

The phrase "nucleic acid" or "polynucleotide sequence" refers to a single or double-stranded polymer of deoxyribonucleotide or ribonucleotide bases read from the 5' to the 3' end. Nucleic acids may also include modified nucleotides that permit correct read-through by a polymerase and do not alter expression of a polypeptide encoded by that nucleic acid.

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

A "coding sequence" or "coding region" refers to a nucleic acid molecule having sequence information necessary to produce a gene product, when the sequence is expressed.

"Homology" refers to the resemblance or similarity between two nucleotide or amino acid sequences. As applied to a gene, "homolog" may refer to a gene similar in structure and/or evolutionary origin to a gene in another organism or another species. As applied to nucleic acid molecules, the term "homolog" means that two nucleic acid sequences, when optimally aligned (see below), share at least 80 percent sequence homology, preferably at least 90 percent sequence homology, more preferably at least 95, 96, 97, 98 or 99 percent sequence homology. "Percentage nucleotide (or nucleic acid) homology" or "percentage nucleotide (or nucleic acid) sequence homology" refers to a comparison of the nucleotides of two nucleic acid molecules which, when optimally aligned, have approximately the designated percentage of the same nucleotides or nucleotides that are not identical but differ by redundant nucleotide substitutions (the nucleotide substitution does not change the amino acid encoded by the particular codon). For example, "95% nucleotide homology" refers to a comparison of the nucleotides of two nucleic acid molecules which, when optimally aligned, have 95% nucleotide homology.

A "genomic sequence" or "genome" refers to the complete DNA sequence of an organism. The genomic sequences of both *M. avium* and of *M. paratuberculosis* are known and are currently available. The genomic sequence of *M. avium* can be obtained from the Institute for Genomic Research. The genomic sequence of *M. paratuberculosis* can be obtained from the GenBank, under accession number AE016958.

A "genomic island" (GI) refers to a nucleic acid region (and its homologs), that includes three or more consecutive open reading frames (ORFs), regardless of the size. A "MAP" genomic island means any genomic island (and its homologs) that is present in the *M. paratuberculosis* genome, but is not present in the *M. avium* genome. A "MAV" genomic island means any genomic island (and its homologs) that is present in the *M. avium*-genome, but is not present in the *M. paratuberculosis* genome.

A "junction" between two nucleic acid regions refers to a point that joins two nucleic acid regions. A "junction sequence" refers to a nucleic acid sequence that can be used for identification of the junction point. For example, a "junction sequence", or a "junction region" of an inverted region (INV) and a corresponding flanking sequence refers to a nucleic acid segment that crosses the point that joins the inverted region with the flanking sequence. Such a nucleic acid segment is specific to the corresponding junction region (junction sequence), and can be used as its identifier.

The term "nucleic acid construct" or "DNA construct" is sometimes used to refer to a coding sequence or sequences operably linked to appropriate regulatory sequences so as to enable expression of the coding sequence, and inserted into a expression cassette for transforming a cell. This term may be used interchangeably with the term "transforming DNA" or "transgene". Such a nucleic acid construct may contain a coding sequence for a gene product of interest, along with a selectable marker gene and/or a reporter gene.

A "label" is a composition detectable by spectroscopic, photochemical, biochemical, immunochemical, or chemical means. Useful labels include $^{32}P$, fluorescent dyes, electron-dense reagents, enzymes (e.g., as commonly used in an ELISA), biotin, digoxigenin, or proteins for which antisera or monoclonal antibodies are available. For example, labels are preferably covalently bound to a genomic island, directly or through the use of a linker.

A "nucleic acid probe sequence" or "probe" is defined as a nucleic acid capable of binding to a target nucleic acid of complementary sequence through one or more types of chemical bonds, usually through complementary base pairing, usually through hydrogen bond formation. A probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. Probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with reference, e.g., to a cell, or nucleic acid, protein, expression cassette, or vector, indicates that the cell, nucleic acid, protein, expression cassette, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, underexpressed, or not expressed at all.

"Antibodies" refers to polyclonal and monoclonal antibodies, chimeric, and single chain antibodies, as well as Fab fragments, including the products of a Fab or other immunoglobulin expression library. With respect to antibodies, the term, "immunologically specific" refers to antibodies that bind to one or more epitopes of a protein of interest, but which do not substantially recognize and bind other molecules in a sample containing a mixed population of antigenic biological molecules. The present invention provides antibodies immunologically specific for part or all of the polypeptides of the present invention, e.g., those polypeptides encoded by the genes gcpE, pstA, kdpC, papA2, impA, umaA1, fabG2_2, aceAB, mbtH2, lpqP, map0834c, cspB, lipN, and map1634 of *Mycobacterium paratuberculosis.*

An "expression cassette" refers to a nucleic acid construct, which when introduced into a host cell, results in transcription and/or translation of a RNA or polypeptide, respectively. Expression cassettes can be derived from a variety of sources depending on the host cell to be used for expression. An expression cassette can contain components derived from a viral, bacterial, insect, plant, or mammalian source. In the case of both expression of transgenes and inhibition of endogenous genes (e.g., by antisense, or sense suppression) the inserted polynucleotide sequence need not be identical and can be "substantially identical" to a sequence of the gene from which it was derived.

The term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include other forms of expression vectors, such as viral vectors (e.g., replication defective retroviruses, adenoviruses and adena-associated viruses), which serve equivalent functions.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated nucleic acid of the present invention is separated from open reading frames that flank the desired gene and encode proteins other than the desired protein. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

In the case where the inserted polynucleotide sequence is transcribed and translated to produce a functional polypeptide, because of codon degeneracy a number of polynucleotide sequences will encode the same polypeptide. These variants are specifically covered by the term "polynucleotide sequence from" a particular gene. In addition, the term specifically includes sequences (e.g., full length sequences) substantially identical (determined as described below) with a gene sequence encoding a protein of the present invention and that encode proteins or functional fragments that retain the function of a protein of the present invention, e.g., a disease causing agent of *M. paratuberculosis.*

The term "immunization" is the process by which an individual is exposed to a material that is designed to stimulate his or her immune system against that material. The material is known as an "immunizing agent" or "immunogen". When the immunizing agent is administered to a subject, the subject develops an immune response, which can be used for prevention and treatment against Johne's disease or Crohn's disease.

The term "vaccine" refers to an antigenic preparation used to produce immunity to a disease, in order to prevent or ameliorate the effects of infection. Vaccines are typically prepared using a combination of an immunologically effective amount of an immunogen together with an adjuvant effective for enhancing the immune response of the vaccinated subject against the immunogen. The process of distributing and administrating vaccines is referred to as "vaccination".

Vaccine formulations will contain a "therapeutically effective amount" of the active ingredient, that is, an amount capable of eliciting an immune response in a subject to which the composition is administered. In the treatment and prevention of Johne's disease, for example, a "therapeutically effective amount" would preferably be an amount that enhances resistance of the vaccinated subject to new infection and/or reduces the clinical severity of the disease. Such protection will be demonstrated by either a reduction or lack of symptoms normally displayed by a subject infected with Johne's disease, a quicker recovery time and/or a lowered count of *M. paratuberculosis* bacteria. Vaccines can be administered prior to infection, as a preventative measure against Johne's or Crohn's disease. Alternatively, vaccines can be administered after the subject already has contracted a disease. Vaccines given after exposure to mycobacteria may be able to attenuate the disease, triggering a superior immune response than the natural infection itself.

A "pharmaceutically acceptable carrier" means any conventional pharmaceutically acceptable carrier, vehicle, or excipient that is used in the art for production and administration of vaccines. Pharmaceutically acceptable carriers are typically non-toxic, inert, solid or liquid carriers.

The term "adjuvant" refers to a compound that enhances the effectiveness of the vaccine, and may be added to the formulation that includes the immunizing agent. Adjuvants provide enhanced immune response even after administration of only a single dose of the vaccine. Adjuvants may include, for example, muramyl dipeptides, avridine, aluminum hydroxide, dimethyldioctadecyl ammonium bromide (DDA), oils, oil-in-water emulsions, saponins, cytokines, and other substances known in the art. Examples of suitable adjuvants are described in U.S. Patent Application Publication No. US2004/0213817 A1.

In the case of polynucleotides used to immunize a subject, the introduced sequence need not be perfectly identical to a sequence of the target endogenous gene. The introduced polynucleotide sequence is typically at least substantially identical (as determined below) to the target endogenous sequence.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

The term "biologically active fragment" is intended to mean a part of the complete molecule which retains all or some of the catalytic or biological activity possessed by the complete molecule, especially activity that allows specific binding of the antibody to an antigenic determinant.

"Functional equivalents" of an antibody include any molecule capable of specifically binding to the same antigenic determinant as the antibody, thereby neutralizing the molecule, e.g., antibody-like molecules, such as single chain antigen binding molecules.

Optimal alignment of sequences for comparison may be conducted by methods commonly known in the art, e.g., the local homology algorithm (Smith and Waterman, 1981, *Adv. Appl. Math.* 2: 482-489), by the search for similarity method (Pearson and Lipman 1988, *Proc. Natl. Acad. Sci. USA* 85: 2444-2448), by computerized implementations of these algorithms (GAP, BESTFIT, BLAST, FASTA, and TFASTA in the Wisconsin Genetics Software Package, Genetics Computer Group (GCG), Madison, Wis.), or by inspection.

Protein and nucleic acid sequence identities are evaluated using the Basic Local Alignment Search Tool ("BLAST") which is well known in the art (Karlin and Altschul, 1990, *Proc. Natl. Acad. Sci. USA* 87: 2267-2268; Altschul et al., 1997, *Nucl. Acids Res.* 25: 3389-3402). The BLAST programs identify homologous sequences by identifying similar segments, which are referred to herein as "high-scoring segment pairs," between a query amino or nucleic acid sequence and a test sequence which is preferably obtained from a protein or nucleic acid sequence database. Preferably, the statistical significance of a high-scoring segment pair is evaluated using the statistical significance formula (Karlin and Altschul, 1990), the disclosure of which is incorporated by reference in its entirety. The BLAST programs can be used with the default parameters or with modified parameters provided by the user.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% compared to a reference sequence using the programs described herein; preferably BLAST using standard parameters, as described. These values can be appropriately adjusted to determine corresponding identity of proteins encoded by two nucleotide sequences by taking into account codon degeneracy, amino acid similarity, reading frame positioning and the like.

"Substantial identity" of amino acid sequences for purposes of this invention normally means polypeptide sequence identity of at least 40%. Preferred percent identity of polypeptides can be any integer from 40% to 100%. More preferred embodiments include at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 98.7%, or 99%.

Polypeptides that are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

3. Identification of Vaccine Targets of the Present Invention

The invention described here utilizes large-scale identification of disrupted genes and the use of bioinformatics to select mutants that could be characterized in animals. Employing such an approach, novel virulence determinants were identified, based on mutants that were investigated in mice. These virulence determinants can be used for designing vaccines. Compared to similar protocols established for identifying virulence genes such as signature-tagged mutagenesis (Ghadiali et al., 2003, *Nucleic Acids Res.* 31: 147-151), the approach employed here is simpler and uses a smaller number of animals.

The present invention also provides immunogenic preparations and vaccines containing at least one plasmid encoding and expressing at least one immunogen against *M. paratuberculosis* compositions formulated with an adjuvant.

The target nucleic acid sequences of the present invention include the gcpE, pstA, kdpC, papA2, impA, umaA1, fabG2_2, aceAB, mbtH2, lpqP, map0834c, cspB, lipN, and map1634 genes of *M. paratuberculosis*, their homologs, and the corresponding gene products. Presence of these genes, their homologs, and/or their products in a sample is indicative of a *M. paratuberculosis* infection.

The start and end coordinates of the *M. paratuberculosis* polynucleotides of this invention (e.g., genes, genomic islands, inverted regions, junction sequences) are based on the genomic sequence of *M. paratuberculosis* strain K10 (Li et al., 2005, *Proc. Natl. Acad. Sci. USA* 102: 12344-12349; GenBank No. AE016958). The start and end coordinates of the *M. avium* polynucleotides of this invention (e.g., genes, genomic islands, inverted regions, junction sequences) are based on the genomic sequence of *M. avium* strain 104, as obtained from The Institute for Genomic Research.

The size of gcpE is 1167 base pairs (bp), and it is located at positions 3272755 through 3273921 of the *M. paratuberculosis* genomic sequence.

The size of pstA is 12084 base pairs (bp), and it is located at positions 1309241 through 1321324 of the *M. paratuberculosis* genomic sequence.

The size of kdpC is 876 base pairs (bp), and it is located at positions 1038471 through 1039346 of the *M. paratuberculosis* genomic sequence.

The size of papA2 is 1518 base pairs (bp), and it is located at positions 1854059 through 1855576 of the *M. paratuberculosis* genomic sequence.

The size of impA is 801 base pairs (bp), and it is located at positions 1386766 through 1387566 of the *M. paratuberculosis* genomic sequence.

The size of umaA1 is 861 base pairs (bp), and it is located at positions 4423752 through 4424612 of the *M. paratuberculosis* genomic sequence.

The size of fabG2_2 is 750 base pairs (bp), and it is located at positions 2704522 through 2705271 of the *M. paratuberculosis* genomic sequence.

The size of aceAB is 2288 base pairs (bp), and it is located at positions 1795784 through 1798072 of the *M. paratuberculosis* genomic sequence.

The size of mbtH2 is 233 base pairs (bp), and it is located at positions 2063983 through 2064216 of the *M. paratuberculosis* genomic sequence.

The size of lpqP is 971 base pairs (bp), and it is located at positions 4755529 through 4756500 of the *M. paratuberculosis* genomic sequence.

The size of map0834c is 701 base pairs (bp), and it is located at positions 851908 through 852609 of the *M. paratuberculosis* genomic sequence.

The size of map1634 is 917 base pairs (bp), and it is located at positions 1789023 through 1789940 of the *M. paratuberculosis* genomic sequence.

In another aspect, the virulence determinants of the present invention include genomic islands (GIs). These GIs are strain-specific. The inventors have identified 18 *M. paratuberculosis*-specific genomic islands (MAPs), that are absent from the *M. avium* genome (Table 8).

The size of MAP-1 is 19,343 base pairs (bp). MAP-1 includes 17 ORFs. MAP-1 is located at positions 99,947 through 119,289 of the *M. paratuberculosis* genomic sequence.

The size of MAP-2 is 3,858 base pairs (bp). MAP-2 includes 3 ORFs. MAP-2 is located at positions 299,412 through 303,269 of the *M. paratuberculosis* genomic sequence.

The size of MAP-3 is 2,915 base pairs (bp). MAP-3 includes 3 ORFs. MAP-3 is located at positions 410,091 through 413,005 of the *M. paratuberculosis* genomic sequence.

The size of MAP-4 is 16,681 base pairs (bp). MAP-4 includes 17 ORFs. MAP-4 is located at positions 872,772 through 889,452 of the *M. paratuberculosis* genomic sequence.

The size of MAP-5 is 14,191 base pairs (bp). MAP-5 includes 17 ORFs. MAP-5 is located at positions 989,744 through 1,003,934 of the *M. paratuberculosis* genomic sequence.

The size of MAP-6 is 8,971 base pairs (bp). MAP-6 includes 6 ORFs. MAP-6 is located at positions 1,291,689 through 1,300,659 of the *M. paratuberculosis* genomic sequence.

The size of MAP-7 is 6,914 base pairs (bp). MAP-7 includes 6 ORFs. MAP-7 is located at positions 1,441,777 through 1,448,690 of the *M. paratuberculosis* genomic sequence.

The size of MAP-8 is 7,915 base pairs (bp). MAP-8 includes 8 ORFs. MAP-8 is located at positions 1,785,511 through 1,793,425 of the *M. paratuberculosis* genomic sequence.

The size of MAP-9 is 11,202 base pairs (bp). MAP-9 includes 10 ORFs. MAP-9 is located at positions 1,877,255 through 1,888,456 of the *M. paratuberculosis* genomic sequence.

The size of MAP-10 is 2,993 base pairs (bp). MAP-10 includes 3 ORFs. MAP-10 is located at positions 1,891,000 through 1,893,992 of the *M. paratuberculosis* genomic sequence.

The size of MAP-11 is 2,989 base pairs (bp). MAP-11 includes 4 ORFs. MAP-11 is located at positions 2,233,123 through 2,236,111 of the *M. paratuberculosis* genomic sequence.

The size of MAP-12 is 11,977 base pairs (bp). MAP-12 includes 11 ORFs. MAP-12 is located at positions 2,378,957 through 2,390,933 of the *M. paratuberculosis* genomic sequence.

The size of MAP-13 is 19,977 base pairs (bp). MAP-13 includes 19 ORFs. MAP-13 is located at positions 2,421,552 through 2,441,528 of the *M. paratuberculosis* genomic sequence.

The size of MAP-14 is 19,315 base pairs (bp). MAP-14 includes 19 ORFs. MAP-14 is located at positions 3,081,906 through 3,101,220 of the *M. paratuberculosis* genomic sequence.

The size of MAP-15 is 4,143 base pairs (bp). MAP-15 includes 3 ORFs. MAP-15 is located at positions 3,297,661 through 3,301,803 of the *M. paratuberculosis* genomic sequence.

The size of MAP-16 is 79,790 base pairs (bp). MAP-16 includes 56 ORFs. MAP-16 is located at positions 4,140,311 through 4,220,100 of the *M. paratuberculosis* genomic sequence.

The size of MAP-17 is 3,655 base pairs (bp). MAP-17 includes 5 ORFs. MAP-17 is located at positions 4,735,049 through 4,738,703 of the *M. paratuberculosis* genomic sequence.

The size of MAP-18 is 3,512 base pairs (bp). MAP-18 includes 3 ORFs. MAP-18 is located at positions 4,800,932 through 4,804,443 of the *M. paratuberculosis* genomic sequence.

The inventors have also identified 24 *M. avium*-specific genomic islands (MAVs), that are absent from the *M. paratuberculosis* genome (Table 9).

The GIs of the present invention (both MAPs and MAVs) can be used as target nucleic acid sequences for design of vaccines and drugs that are strain-specific. Thus, the targets enable one skilled in the art to distinguish between the presence of *M. paratuberculosis* or *M. avium* in a sample. Should both *Mycobacterium* strains be present in a sample, one should be able to identify the presence of both classes of target polynucleotides in the sample.

Figure 7:
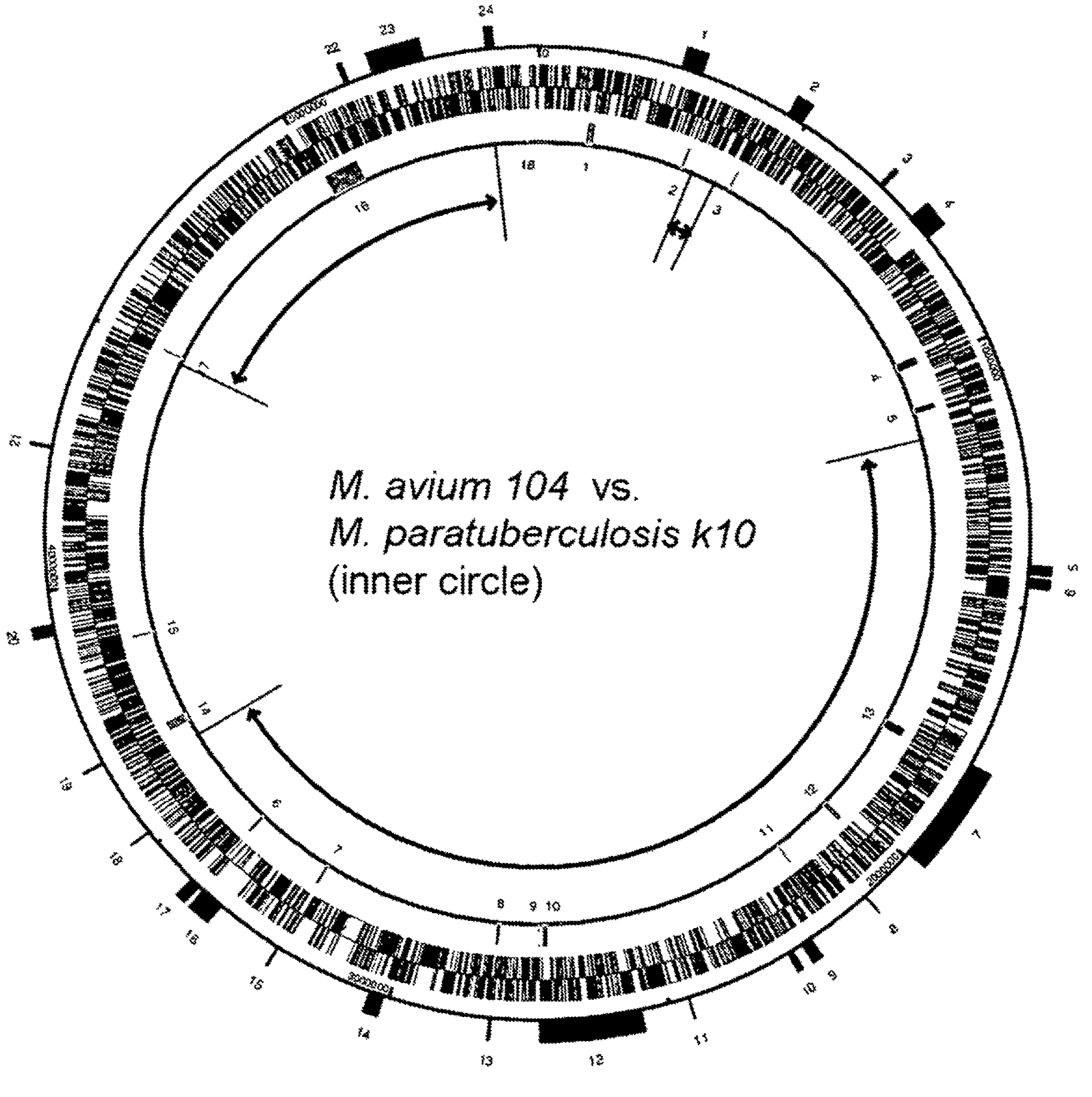
FIG. 7 is a genomic map showing the synteny of *M. avium* and *M. paratuberculosis* genomes.

It is possible to diagnose the presence of *M. paratuberculosis* or *M. avium* in a sample due to the inversion of three large genomic fragments in *M. paratuberculosis* in comparison to *M. avium*. It was unexpectedly discovered that, when the GIs associated with both genomes were aligned, three large genomic fragments in *M. paratuberculosis* were identified as inverted relative to the corresponding genomic fragments in *M. avium*. These inverted nucleic acid regions (INV) had the sizes of approximately 54.9 Kb, 863.8 Kb and 1,969.4 Kb (FIG. 7).

The target polynucleotide may be DNA. In some variations, the target polynucleotide may be obtained from total cellular DNA, or in vitro amplified DNA.

The specificity of single stranded DNA to hybridize complementary fragments is determined by the "stringency" of the reaction conditions. Hybridization stringency increases as the propensity to form DNA duplexes decreases. In nucleic acid hybridization reactions, the stringency can be chosen to either favor specific hybridizations (high stringency), which can be used to identify, for example, full-length clones from a library. Less-specific hybridizations (low stringency) can be used to identify related, but not exact, DNA molecules (homologous, but not identical) or segments.

Identification of target sequences of the present invention may be accomplished by a number of techniques. For instance, oligonucleotide probes based on the sequences disclosed here can be used to identify the desired gene in a cDNA or genomic DNA library from a desired bacterial strain. To construct genomic libraries, large segments of genomic DNA are generated by random fragmentation, e.g. using restriction endonucleases, and are ligated with vector DNA to form concatemers that can be packaged into the appropriate vector. The cDNA or genomic library can then be screened using a probe based upon the sequence of a cloned gene such as the polynucleotides disclosed here. Probes may be used to hybridize with genomic DNA or cDNA sequences to identify homologous genes in the same or different bacterial strains.

Alternatively, the nucleic acids of interest can be amplified from nucleic acid samples using amplification techniques. For instance, polymerase chain reaction (PCR) technology can be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying the target sequences of the present invention from a sample are generated from comparisons of the sequences provided herein, according to standard PCR guides. For examples of primers used see the Examples section below.

Polynucleotides may also be synthesized by well-known techniques described in the technical literature. Double-stranded DNA fragments may then be obtained either by synthesizing the complementary strand and annealing the strands together under appropriate conditions, or by adding the complementary strand using DNA polymerase with an appropriate primer sequence.

Once a nucleic acid is isolated using the method described above, standard methods can be used to determine if the nucleic acid is a preferred nucleic acid of the present invention, e.g., by using structural and functional assays known in the art. For example, using standard methods, the skilled practitioner can compare the sequence of a putative nucleic acid sequence thought to encode a preferred protein of the present invention to a nucleic acid sequence encoding a preferred protein of the present invention to determine if the putative nucleic acid is a preferred polynucleotide of the present invention.

Gene amplification and/or expression can be measured in a sample directly, for example, by conventional Southern blotting, Northern blotting to quantitate the transcription of mRNA, dot blotting (DNA analysis), DNA microarrays, or in situ hybridization, using an appropriately labeled probe, based on the sequences provided herein. Various labels can be employed, most commonly fluorochromes and radioisotopes, particularly $^{32}P$. However, other techniques can also be employed, such as using biotin-modified nucleotides for introduction into a polynucleotide. The biotin then serves as the site for binding to avidin or antibodies, which can be labeled with a variety of labels, such as radionuclides, fluorescers, enzymes, or the like. Alternatively, antibodies can be employed that can recognize specific duplexes, including DNA duplexes, RNA duplexes, DNA-RNA hybrid duplexes or DNA-protein duplexes. The antibodies in turn can be labeled and the assay can be carried out where the duplex is bound to a surface, so that upon the formation of duplex on the surface, the presence of antibody bound to the duplex can be detected.

Gene expression can also be measured by immunological methods, such as immunohistochemical staining. With immunohistochemical staining techniques, a sample is prepared, typically by dehydration and fixation, followed by reaction with labeled antibodies specific for the gene product coupled, where the labels are usually visually detectable, such as enzymatic labels, fluorescent labels, luminescent labels, and the like. Gene expression can also be measured using PCR techniques, or using DNA microarrays, commonly known as gene chips.

4. DNA Vaccines

The use of deoxyribonucleic acid (DNA) molecules for vaccination is also known (Wolf et al., 1990*, Science* 247: 1465-1468). This vaccination technique induces cellular and humoral immunity (stimulation of the production of antibodies specifically directed against the immunogen) after in vivo transfection of cells of the subject to be vaccinated with nucleic acids encoding immunologically active proteins.

A "DNA vaccine" or "immunogenic" or "immunological composition" is composed of at least one vector (e.g., plasmid) which may be expressed by the cellular machinery of the subject to be vaccinated or inoculated and of a pharmaceutically acceptable carrier, vehicle, or excipient. The nucleotide sequence of this vector encodes one or more immunogens, such as proteins or glycoproteins capable of inducing, in the subject to be vaccinated or inoculated, a cellular immune response (mobilization of the T lymphocytes) and a humoral immune response (Davis, 1997*, Current Opinion Biotech.* 8: 635-640).

The present invention provides DNA vaccines or immunogenic or immunological compositions for mammals. These DNA vaccines can be generated using the information on target polynucleotides that constitute virulence determinants of Johne's disease or Crohn's disease. In one aspect, the immunized mammals develop an immune response, which can be used for prevention and treatment against Johne's disease or Crohn's disease.

Various routes of administration of the DNA vaccine have been proposed (intraperitoneal, intravenous, intramuscular, subcutaneous, intradermal, mucosal, and the like), and they are useful for the practice of this invention. Various means of administration have also been proposed. Some means include the use of gold particles coated with DNA and projected so as to penetrate into the cells of the skin of the subject to be vaccinated (Tang et al., 1992*, Nature* 356: 152-154). Other means include the use of liquid jet injectors which make it possible to transfect both skin cells and cells of the underlying tissues (Furth et al., 1992*, Analytical Bloch.* 205: 365-368).

The invention also relates to small nucleic acids that selectively hybridize to the exemplified target polynucleotide sequences, including hybridizing to the exact complements of these sequences. Such small nucleic acids include oligonucleotides or small interfering ribonucleic acid (siRNA) molecules.

The invention further provides small interfering ribonucleic acid (siRNA) molecules for prevention and treatment of Johne's or Crohn's diseases. RNA interference (RNAi) using siRNA has been shown to be an effective means of silencing gene expression in cells. For example, retroviral vectors that express small RNAs as hairpin loops can be used for therapeutic purposes.

The oligonucleotide or siRNA may be partially complementary to the target nucleic acid sequence. Alternatively, the oligonucleotide may be exactly complementary to the target nucleic acid sequence. The oligonucleotide or siRNA molecule may be greater than about 4 nucleic acid bases in length and/or less than about 48 nucleic acid bases in length. In a further variation, the oligonucleotide or the siRNA molecule may be about 20 nucleic acid bases in length.

This invention provides a method for delivering an isolated polynucleotide to the interior of a cell in a mammal, comprising the interstitial introduction of an isolated polynucleotide into a tissue of the mammal where the polynucleotide is taken up by the cells of the tissue and exerts a therapeutic effect on the mammal. The method can be used to deliver a therapeutic polypeptide to the cells of the mammal, to provide an immune response upon in vivo transcription and/or translation of the polynucleotide, or to deliver antisense polynucleotides.

It is possible to coadminister DNA vaccines encoding antigen with siRNA targeting the target nucleic acid sequences of this invention, to enhance the antigen-specific cell responses, and elicit potent antibacterial effects in vaccinated subjects. Similarly, a skilled artisan should know to use combined/composite vaccines (see e.g., Talaat et al., 2002*, Vaccine* 20: 538-544, incorporated herein in entirety by reference), to increase the efficacy while reducing the number of vaccinations. For example, two or more antigens of this invention may be combined in a composite vaccine directed against Johne's disease or Crohn's disease.

The vaccines may include other components to serve certain functions, for example, directing the nucleic acid to a certain location in the cell or directing transcription of the antigen. Compositions for transport to the nucleus may be included, particularly members of the high mobility group (HMG), more particularly HMG-1, which is a non-histone DNA-binding protein. In combination with antisense molecules, RNAses such as RNAseH, may be used. Other proteins that will aid or enhance the function of the antigen may be included, such as peptide sequences that direct antigen processing, particularly HLA. presentation, or movement in the cytoplasm.

In one embodiment, the immunized mammals are farm animals, in particular cattle. The immunized cattle develop an immune response, which can be used for prevention and treatment against Johne's disease.

5. Antibodies

The present invention further provides for antibodies immunologically specific for all or part, e.g., an amino-terminal portion, of a polypeptide at least 70% identical to a mycobacterial sequence that is a virulence determinant. Exemplary anti-Johne's and anti-Crohn's antibodies include polyclonal, monoclonal, humanized, bispecific, and heteroconjugate antibodies. The invention also provides functional equivalents of anti-Johne's and anti-Crohn's antibodies, e.g., antibody-like molecules, such as single chain antigen binding molecules.

The antibodies of this invention may be polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include any of the antigens of this invention, its homolog, or a fusion protein thereof. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies of this invention may alternatively be monoclonal antibodies. Monoclonal antibodies may be prepared using hybridoma methods. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies of the invention may further comprise humanized antibodies or human antibodies. Humanized antibodies might be preferably used for prevention and treatment of Crohn's disease. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the methods described in Riechmann et al., 1988, *Nature,* 332: 323-327; and in Verhoeyen et al., 1988, *Science* 239: 1534-1536, by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Administration of Vaccines

In one aspect, a method of treating Johne's disease or Crohn's disease is disclosed. In one embodiment, the method includes production of antibodies directed to *M. paratuberculosis* virulence proteins. This invention discloses a variety of proteins that are virulence determinants, and are thus indicative of *M. paratuberculosis* infection. Methods known in the art can be used to immunize subjects (animals and humans) for purposes of prevention and treatment against Johne's disease or Crohn's disease. Pharmaceutically acceptable carriers are typically used for administration of vaccine compositions. For example, the use of solvents, dispersion media, coatings, antibacterial and antifungal agents, isotonic and absorption delaying agents, and the like media and agents for pharmaceutical active carriers is well known in the art.

In one embodiment, administration of an immunizing agent includes administering in vivo into a tissue of a mammal a construct comprising a nucleotide sequence encoding an antigen, in an amount sufficient that uptake of the construct into cells of the mammal occurs, and sufficient expression results, to generate a detectable antibody response. In a preferred embodiment, the nucleotide sequence encodes an antigen that includes at least one of gcpE, pstA, kdpC, papA2, impA, umaA1, fabG2_2, aceAB, mbtH2, lpqP, map0834c, cspB, lipN, or map1634 genes of *M. paratuberculosis.* In another preferred embodiment, the nucleotide sequence encodes an antigen that includes at least one of the MAP-1, MAP-2, MAP-3, MAP-4, MAP-5, MAP-6, MAP-7, MAP-8, MAP-9, MAP-10, MAP-11, MAP-12, MAP-13, MAP-14, MAP-15, MAP-16, MAP-17, or MAP-18 genomic islands of *M. paratuberculosis.*

The vaccine provided by this invention may be administered subcutaneously, intramuscularly, intradermally, or into an organ. Intramuscular injection has been shown in the past to be an important delivery route for induction of immunity. Skeletal muscle has properties such as high vascularization and multi-nucleation. In addition, it is nonreplicating and capable of expressing recombinant proteins. These properties are advantageous for gene therapy using DNA vaccines. One theory of the mechanism of how muscle presents the protein and induces immune response is that recombinant protein is produced and released into the vascular network of the muscle and eventually presented by professional antigen-presenting cells such as dendritic cells, myoblasts, or macrophages infiltrating the muscle. Another suggestion is that at the injection site muscle injury induces myoblast proliferation and activation of infiltrating macrophages or dendritic-like cells, and they then present antigens through MHC class II antigen. Thus, other tissues which have similar qualities also would be good delivery sites for the vaccine.

The chosen route of administration will depend on the vaccine composition and the disease status of subjects. Relevant considerations include the types of immune cells to be activated, the time which the antigen is exposed to the immune system and the immunization schedule. Although many vaccines are administered consecutively within a short period, spreading the immunizations over a longer time may maintain effective clinical and immunological responses.

To immunize a subject, the vaccine is preferably administered parenterally, usually by intramuscular injection. Other modes of administration, however, such as subcutaneous, intraperitoneal and intravenous injection, are also acceptable. The quantity to be administered depends on the subject to be treated, the capacity of the subject's immune system to synthesize antibodies, and the degree of protection desired. Effective dosages can be readily established by one of ordinary skill in the art through routine trials establishing dose response curves. The subject is immunized by administration of the vaccine in at least one dose, and preferably two to four doses. Moreover, the subject may be administered as many doses as is required to maintain a state of immunity to infection.

Additional vaccine formulations that are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Oral vehicles include such normally employed excipients as, for example, pharmaceutical grades of mannitol, lactose, starch, magnesium, stearate, sodium saccharin cellulose, magnesium carbonate, and the like. The oral vaccine compositions may be taken in the form of solutions, suspensions, tablets, pills, capsules, sustained release formulations, or powders.

Another aspect of the invention provides a pharmaceutical product for use in immunizing a mammal, comprising a pharmaceutically effective amount of a polynucleotide encoding an immunogenic polypeptide, a sealed container enclosing the polynucleotide in a sterile fashion, and means associated with the container for permitting transfer of the polynucleotide from the container to the interstitial space of a tissue, whereby cells of the tissue can take up and express the polynucleotide.

One skilled in the art will know that it is possible to enhance the immune response of an animal to a target immunogen by using a variety of adjuvants. Suitable adjuvants are, for example, described in U.S. Patent Application Pub. No. US 2004/0213817 A1, incorporated herein in entirety by reference.

The invention is also directed to a kit for vaccination against Johne's or Crohn's disease. The kit may include one or more of a sample that includes a target polynucleotide, and one or more nucleic acid probe sequences at least partially complementary to a target nucleic acid sequence. The kit may include instructions for using the kit.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

It is to be understood that this invention is not limited to the particular methodology, protocols, patients, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention.

Example 1

Animals

Groups of BALB/c mice (N=10-20) at 3 to 4 weeks of age were infected with *M. paratuberculosis* strains using intraperitoneal (IP) injection. Infected mice were sacrificed at 3, 6 and 12 weeks post-infection and their livers, spleens and intestines collected for both histological and bacteriological examinations. Tissue sections collected for histopathology were preserved in 10% neutralized buffer formalin (NBF) before embedding in paraffin, cut into 4-5 μm sections, stained with hematoxylin and eosin (HE) or acid fast staining (AFS). Tissue sections from infected animals were examined by two independent pathologists at 3, 6 and 12 weeks post infection. The severity of inflammatory responses was ranked using a score of 0 to 5 based on lesion size and number per field. Tissues with more than 3 fields containing multiple, large-sized lesions were given a score of 5 using the developed scale.

Bacterial Strains, Cultures and Vectors

*Mycobacterium avium* subsp. *paratuberculosis* strain ATCC 19698 (*M. paratuberculosis*) was used for constructing the mutant library. This strain was grown at 37° C. in Middlebrook 7H9 broth enriched with 10% albumin dextrose complex (ADC), 0.5% glycerol, 0.05% Tween 80 and 2 mg/ml of mycobactin J (Allied Monitor, IN).

The temperature-sensitive, conditionally replicating phasmid (phAE94) used to deliver the transposon Tn5367 was obtained from Bill Jacobs laboratory (Albert Einstein College of Medicine) and propagated in *Mycobacterium smegmatis* $mc^2$ 155 at 30° C. as described previously (Bardarov et al., 1997, *Proc. Nat/. Acad. Sci. USA* 94: 10961-10966). The Tn5367 is an IS1096-derived insertion element containing a kanamycin resistance gene as a selectable marker.

After phage transduction, mutants were selected on Middlebrook 7H10 medium plates supplemented with 30 μg/ml of kanamycin. *Escherichia coli* DH5α cells used for cloning purposes were grown on Luria-Bertani (LB) agar or broth supplemented with 100 μg/ml ampicillin. The plasmid vector pGEM T-easy (Promega, Madison, Wis.) was used for TA cloning the PCR products before sequencing.

Construction of a Transposon Mutants Library

The phasmid phAE94 was used to deliver the Tn5367 to mycobacterial cells using a protocol established earlier for *M. tuberculosis*. For each transduction, 10 ml of *M. paratuberculosis* culture was grown to $2\times10^8$ CFU/ml (OD600 0.6-0.8), centrifuged and resuspended in 2.5 ml of MP buffer (50 mM Tris-HCI [pH 7.6], 150 mM NaCl, 2 mM $CaCI_2$) and incubated with $10^{10}$ PFU of phAE94 at the non-permissive temperature (37° C.) for 2 h in a shaking incubator to inhibit a possible lytic or lysogenic cycle of the phage.

Adsorption stop buffer (20 mM sodium citrate and 0.2% Tween 80) was added to prevent further phage infections and this mixture was plated immediately on 7H10 agar supplemented with 30 μg/ml of kanamycin and incubated at 37° C. for 6 weeks. Kanamycin-resistant colonies (5,060) were inoculated into 2 ml of 7H9 broth supplemented with kanamycin in 96-well microtitre plates for additional analysis.

Construction of lipN mutant. The lipN gene was deleted from *M. paratuberculosis* K10 strain using a homologous recombination protocol based on phage transduction. The whole gene was deleted from *M. paratuberculosis* K10 and was tested in mice. This gene was selected for deletion because of its up-regulation when DNA microarrays were used to analyze in vivo (fecal samples) collected from infected cows with high levels of mycobacterial shedding.

Southern Blot Analysis

To examine the randomness of Tn5367 insertions in the *M. paratuberculosis* genome, 10 randomly selected mutants were analyzed by Southern blot using a standard protocol. Kanamycin-resistant *M. paratuberculosis* single colonies were grown separately in 10 ml of 7H9 broth for 10 days at 37° C. before genomic DNA extraction and digestion (2-3 μg) with BamH1 restriction enzyme. Digested DNA fragments from both mutant and wild-type strains were electrophoresed on a 1% agarose gel and transferred to a nylon membrane (Perkin Elmer, Calif.), using an alkaline transfer protocol as recommended by the manufacturer.

A 1.3-kb DNA fragment from the kanamycin resistance gene was radiolabeled with [α-$^{32}$P]-dCTP using a Random Prime Labeling Kit (Promega) in accordance with the manufacture's direction. The radio-labeled probe was hybridized to the nylon membrane at 65° C. overnight in a shaking water bath before washing, exposure to X-ray film, and development to visualize hybridization signals.

Sequencing of the Transposon Insertion Site

FIG. 1 shows a schematic representation of the transposon Tn5367 from strain ATCC19698 used for insertion mutagenesis of *M. paratuberculosis*. To determine the exact transposon insertion site within the *M. paratuberculosis* genome, a protocol for sequencing randomly primed PCR products was adopted from previous work on *M. tuberculosis* with slight modifications. For PCR amplification, the genomic DNA of each mutant was extracted from individual cultures by boiling for 10 min, centrifuged at 10,000×g for 1 min, and 10 μl of the supernatants were used in a standard PCR reaction. For the first round of PCR, a transposon-specific primer (AMT31: 5'TGCAGCAACGCCAGGTCCACACT-3') (SEQ ID NO:1) and the degenerate primer (AMT38: 5'-GTAATACGACTCACTATAGGGCNNNNCATG-3') (SEQ ID NO:2) were used to amplify the chromosomal sequence flanking the transposon insertion site.

PCR was carried out in a total volume of 25 μl in 10 mM Tris/HCI (pH 8.3), 50 mM KCl, 2.0 mM $MgCI_2$, 0.01% (w/v) BSA, 0.2 mM dNTPs, 0.1 μM of primer AMT31, 1.0 μM of primer AMT38 and 0.75 U Taq polymerase (Promega). First-round amplification was performed with an initial denaturing step at 94° C. for 5 min, followed by 40 cycles of denaturing at 94° C. for 1 min, annealing at 50° C. for 30 s and extension at 72° C. for 90 s, with a final extension step at 72° C. for 7 min. Only 1 μl of the first round amplification was then used as a template for the second round PCR (nested PCR) using a nested primer (AMT32: 5'-CTCTTGCTCTTCCGCTTCTTCTCC-3') (SEQ ID NO:3) derived from the Tn5367 and T7 primer (AMT 39: 5'-TAATACGACTCACTATAGGG-3') (SEQ ID NO:4) present within the degenerative primer sequence. Reactions were carried out in a total volume of 50 μl in 10 mM Tris/HCI (pH 8.3), 50 mM KCl, 1.5 mM $MgCl_2$, 0.2 mM dNTPs, 0.5 μM primers, 5% (v/v) DMSO and 0.75 U Taq polymerase.

A final round of amplification was performed with a denaturing step at 95° C. for 5 min followed by 35 thermocycles (94° C. for 30 s, 57° C. for 30 s and 72° C. for 1 min) with a final extension step at 72° C. for 10 min. For almost ⅔ of the sequenced mutants, no cloning was attempted and AMT152 primer (5'-TTGCTCTTCCGCTTCTTCT-3') (SEQ ID NO:5) present in Tn5367 was used to directly sequence gel-purified amplicons. The product of the second amplification was gel-purified (Wizard Gel-extraction kit, Promega, Madison, Wis.) and cloned into pGEM T-easy vector for plasmid mini-preparation followed by automatic sequencing. Inserts in pGEM T-easy vector was confirmed by EcoRI restriction digestion and the sequencing was carried out using SP-6 primer (5'-TATTTAGGTGACACTATAG-3') (SEQ ID NO:6).

To identify the precise transposon-insertion site in the *M. paratuberculosis* genome, the transposon sequence was trimmed from the cloning vector sequences and a BLASTN search was used against the *M. paratuberculosis* K-10 complete genome sequence (GenBank accession no. AE016958). Sequences with at least 100 bp of alignment matching to the *M. paratuberculosis* genome were further analyzed while others without any transposon sequence were not analyzed to avoid using amplicons generated by non-specific primer binding and amplification.

Statistical Analysis

All bacterial counts from mouse organs were statistically analyzed using the Excel program (Microsoft, Seattle, Wash.). All counts are expressed as the mean±standard deviation (S.D.). Differences in counts between groups were analyzed with a Student's t-test for paired samples. Differences were considered to be significant if a probability value of $p<0.05$ was obtained when the CFU count of mutant strains were compared to that of the wild-type strain.

Generation of *M. paratuberculosis* Mutant Library

A genome-wide random-insertion mutant library was generated for the *M. paratuberculosis* ATCC 19698 using the temperature-sensitive mycobacteriophage phAE94 developed earlier for *M. tuberculosis*. A library consisting of 5,060 kanamycin-resistance colonies was obtained by the insertion of transposon Tn5367 in the bacterial genome (FIG. 1). One transduction reaction of $10^9$ mycobacterial cells with phAE94 yielded all of the kanamycin resistant colonies used throughout this study. None of the retrieved colonies displayed a variant colony morphology from that usually observed in members of the *M. avium* complex. A large-scale sequencing strategy was employed to identify disrupted genes.

Identification of the Transposition Sites in *M. paratuberculosis* Mutants

Among the library of 5,060 mutants, 1,150 were analyzed using a high-throughput sequencing analysis employing a randomly primed PCR protocol that was successful in characterizing an *M. tuberculosis*-transposon library. These sequences were used to search *M. paratuberculosis* K-1 0 complete genome using BLASTN algorithm to identify the insertion site in 20% of the library. Generally, unique insertion sites (N=970) were identified, and almost ⅔ of the insertions occurring in predicted open reading frames (ORFs) while the rest of the insertions occurred in the intergenic regions (N=330) (Table 1).

TABLE 1

Percentage and number of unique insertions in a library of 5,060 mutants Analyzed

| Insertion Sites | Number | No. of unique Insertions | % Unique |
|---|---|---|---|
| ORF | 714 | 640 | 89.6 |
| Intergenic region | 436 | 330 | 75.7 |
| Total | 1150 | 970 | 84.3 |

*indicates the percentage of insertions in unique sites within ORF or intergenic regions.

Among the 970 unique insertions within ORFs, only 288 of the predicted mycobacterial ORFs were disrupted at least once by the transposition of Tn5367 indicating that more than an insertion occurred multiple times in some genes. In fact, only 10.4% of disrupted ORFs showed more than one insertion per ORF indicating the presence of "hot spots" for transposition with Tn5367. Compared to insertions in ORFs, a higher rate by at least two times was observed when intergenic regions (24.3%) were examined (Table 2). Overall, the structure of the *M. paratuberculosis* mutant library was similar to that constructed in *M. tuberculosis.*

More scrutiny of the DNA sequences in both coding and intergenic regions revealed that regions most susceptible to transposon insertions are those with G+C content ranging from 50.5% to 60.5%, which is considerably lower than the average G+C content of the whole *M. paratuberculosis* (69.2%) (Table 2). Analysis of the flanking regions of Tn5367 site of insertion in genes with high frequency of transposition (N≥4) identified areas of AT or TA repeats (e.g. TTT(T/A), AA(A/T) or TAA) as the most predominant sequences.

To illustrate the randomness of the Tn5367 transposition in *M. paratuberculosis* genome, the gene positions of all sequenced mutants were mapped to the genome sequence of *M. paratuberculosis* K10 (GenBank No. AE016958). Additionally, several mutants showed insertion into ORFs that have multiple copies in the genome (e.g. gene families or paralogous genes). These were excluded from further analysis.

Figure 2:
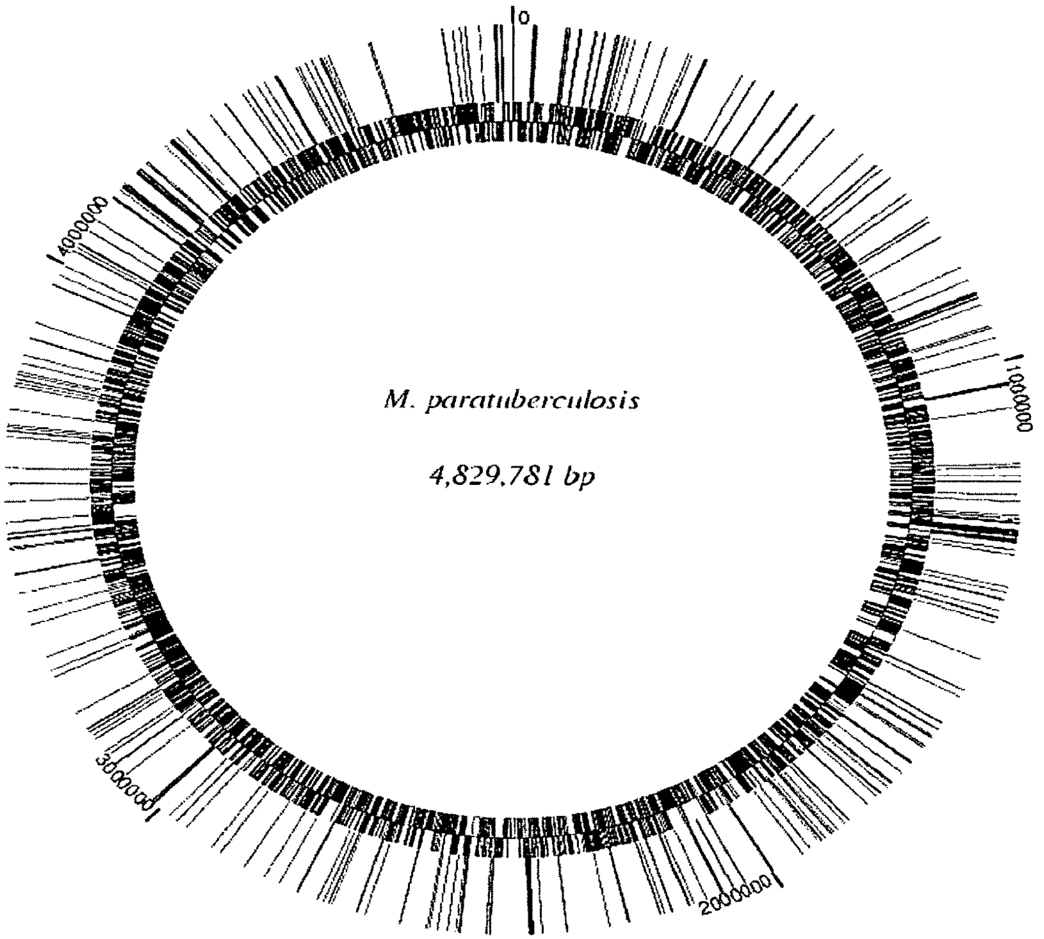
FIG. 2 depicts a genomic map showing the distribution of 1,128 transposon-insertion sites on the chromosome of *M. paratuberculosis.*

As shown in FIG. 2, the transposition insertions were distributed in all parts of the genome without any apparent bias to a particular area. Overall, 1,128 mutants underwent the second level of bioinformatic analysis. FIG. 2 shows the distribution of 1,128 transposon-insertion sites on the chromosome of *M. paratuberculosis* K-10 indicated by long bars on the outer-most circle. The inner two circles of short bars show predicted genes transcribed in sense or antisense directions.

TABLE 2

Characterization of *M. paratuberculosis* mutants with high insertion frequency (>10 insertions)

| | Genome Coordinates | Gene ID | No. of insertions | G + C % | Gene products* |
|---|---|---|---|---|---|
| Coding regions | 1297579-1298913 | MAP1235 | 43 | 55.88 | Hypothetical protein |
| | 1719957-1721030 | MAP 1566 | 42 | 58.19 | Hypothetical protein |
| | 878808-880535 | MAP 0856C | 25 | 57.98 | Hypothetical protein |
| | 877826-878770 | MAP 0855 | 25 | 59.57 | Hypothetical protein |

TABLE 2-continued

Characterization of *M. paratuberculosis* mutants with high insertion frequency (>10 insertions)

| | Genome Coordinates | Gene ID | No. of insertions | G + C % | Gene products* |
|---|---|---|---|---|---|
| | 4266449-4267747 | MAP 3818 | 15 | 59.66 | Hypothetical protein |
| | 1295719-1296441 | MAP 1233 | 13 | 50.48 | Hypothetical protein |
| | 1296587-1297387 | MAP 1234 | 13 | 57.42 | Hypothetical protein |
| | 4803081-4803626 | MAP 4327C | 12 | 60.25 | Hypothetical protein |
| | 299412-300203 | MAP 0282C | 11 | 60.47 | Hypothetical protein |
| Intergenic regions | 2380554-2381286 | MAP2149c-MAP2150 | 97 | 54.3 | Hypothetical proteins |
| | 1276333-1276722 | MAP1216c-MAP1217c | 44 | 52.9 | LpqQ & hypothetical protein |
| | 1997030-1997898 | MAP1820-MAP1821c | 26 | 54.01 | Hypothetical proteins |
| | 4455022-4458337 | MAP3997c-MAP3998c | 21 | 53.9 | SerB and hypothetical protein |
| | 1409338-1410190 | MAP1318c-MAP1319 | 20 | 57.4 | Adenylate cyclase |
| | 2383052-2384295 | MAP2151-MAP2152c | 20 | 54.1 | Hypothetical proteins |
| | 300204-301106 | MAP0282c-MAP0283c | 17 | 58.2 | Hypothetical proteins |
| | 31518-32640 | MAP0027-MAP0028c | 13 | 57.8 | Hypothetical proteins |
| | 4263656-4264948 | MAP3815-MAP3816 | 13 | 60.4 | Hypothetical proteins |
| | 4810959-4811624 | MAP4333-MAP4334 | 11 | 56.7 | Hypothetical proteins |

*Gene products were described based on cluster of proteins analysis with at least 50% identity to other mycobacterial spp. For intergenic regions, the products of both flanking genes were listed.

To further analyze the expected phenotypes of the disrupted genes, the flanking sequences of each disrupted gene were examined, to determine their participation in transcriptional units such as operons. This analysis could reveal potential polar effect that could be observed in some mutants. Using the operon prediction algorithm (OPERON), approximately 124 (43.0%) of disrupted ORFs were identified as members of 113 putative operons (Table 3), indicating possible phenotypes related to disruption of function encoded by the whole operon and not just the disrupted gene. A total of 52 of the disrupted genes were within the last gene of an operon and were unlikely to affect the expression of other genes.

A total of 23 of the Tn5367 insertions were counted in several genes of the same 12 operons suggesting preference of transpositions throughout these sequences. For example, in the kdp operon (encoding putative potassium translocating proteins), 4 genes were disrupted among the 5 genes constituting this operon. Overall, sequence analysis of transposon junction sites identified disruption of a unique set of genes scattered all over the genome.

TABLE 3

Operon analysis of 288 ORFs disrupted by transposons in this study

| | Operon (%) | Not in operon (%) |
|---|---|---|
| Number | 124 (43.0) | 164 (56.9) |
| First gene | 40 (32.3) | N/A |

TABLE 3-continued

Operon analysis of 288 ORFs disrupted by transposons in this study

| | Operon (%) | Not in operon (%) |
|---|---|---|
| Middle gene | 32 (35.8) | N/A |
| Last gene | 52 (41.9) | |

*N/A: Not applicable

Sequence Analysis of Disrupted Genes

A total of 288 genes represented by 970 mutants were identified as disrupted from the initial screening of the transposon mutant library constructed in *M. paratuberculosis*. Examining the potential functional contribution of each disrupted gene among different functional classes encoded in the completely sequenced genome of *M. paratuberculosis* K10 strain will better characterize their roles in infection. With the help of the Cluster of Orthologous Group website, disrupted genes were sorted into functional categories (Table 4). Six genes did not have a match in the COG functional category of *M. paratuberculosis* and consequently were analyzed using *M. tuberculosis* functional category. These genes are involved in different cellular processes such as lipid metabolism (desA1), cell wall biosynthesis (mmpS4) and several possible lipoproteins (lppP, lpqJ, lpqN) including a member of the PE family (PE6).

TABLE 4

List of functional categories of 288 disrupted genes that were identified

| | Coding Sequences | | Mutants Number | |
|---|---|---|---|---|
| Functional Category | Number in genome | % in genome | Number mutant | % in genome |
| Translation | 154 | 3.5 | 6 | 3.9 |
| RNA processing and modification | 1 | 0.02 | 0 | 0.0 |
| Transcription | 262 | 6.0 | 8 | 3.1 |
| Replication, recombination and repair | 179 | 4.1 | 13 | 7.3 |
| Chromatin structure and dynamics | 1 | 0.02 | 0 | 0.0 |
| Cell cycle control, mitosis and meiosis | 34 | 0.8 | 3 | 8.8 |
| Defense mechanisms | 46 | 1.1 | 5 | 10.9 |
| Signal transduction mechanisms | 112 | 2.6 | 6 | 5.4 |
| Cell wall/membrane biogenesis | 132 | 3.0 | 12 | 9.1 |
| Cell motility | 10 | 0.2 | 0 | 0.0 |
| Intracellular trafficking and secretion | 20 | 0.5 | 0 | 0.0 |
| Posttranslational modification, protein turnover, chaperones | 102 | 2.3 | 5 | 4.9 |
| Energy production and conversion | 277 | 6.4 | 10 | 3.6 |
| Carbohydrate transport and metabolism | 187 | 4.3 | 18 | 9.6 |
| Amino acid transport and metabolism | 246 | 5.7 | 16 | 6.5 |
| Nucleotide transport and metabolism | 67 | 1.5 | 2 | 3.0 |
| Coenzyme transport and metabolism | 126 | 2.9 | 3 | 2.4 |
| Lipid transport and metabolism | 326 | 7.5 | 20 | 6.1 |

TABLE 4-continued

List of functional categories of 288 disrupted genes that were identified

| Functional Category | Coding Sequences: Number in genome | Coding Sequences: % in genome | Mutants Number: Number mutant | Mutants Number: % in genome |
|---|---|---|---|---|
| Inorganic ion transport and metabolism | 174 | 4.0 | 9 | 5.2 |
| Secondary metabolites biosynthesis, transport and catabolism | 357 | 8.2 | 26 | 7.3 |
| General function prediction only | 375 | 8.6 | 30 | 8.0 |
| Unknown function | 248 | 5.7 | 16 | 6.5 |
| Unknown | 914 | 21.0 | 80 | 8.8 |

Interestingly, genes involved in cell motility, intracellular trafficking and secretions were not represented in the mutants that were analyzed so far despite their comprising a substantial number of genes (N=30) (Table 4). However, for most functional groups, the percentage of disrupted genes ranged between 3-11% of the genes encoded within the *M. paratuberculosis* genome.

In most of the functional classes, the percentage of disrupted genes among mutants agreed with the percentage of particular functional class to the rest of the genome. Only 2 gene groups (bacterial defense mechanisms and cell cycling) were over-represented in the mutant library indicating potential sequence divergence from the high G+C content of the rest of the genome, which favorably agreed with the Tn5367 insertional bias discussed before.

Colonization of Transposon Mutants to Mice Organs

To identify novel virulence determinants in *M. paratuberculosis*, the mouse model of *paratuberculosis* was employed to characterize selected transposon mutants generated in this study. Bioinformatic analysis was used to identify genes with potential contribution to virulence. Genes were selected if information on their functional role was available, especially genes involved in cellular process believed to be necessary for survival inside the host or genes similar to known virulence factors in other bacteria (Table 5).

The screen for virulence determinants was designed to encompass mutations in a broad range of metabolic pathways to determine whether any could play an essential role for *M. paratuberculosis* persistence during the infection. Genes involved in carbohydrate metabolism (e.g. gcpE, impA), ion transport and metabolism (e.g. kdpC, trpE2) and cell wall biogenesis (e.g. mmpL 10, umaA1) were chosen for further investigating in the mouse model of *paratuberculosis*, and respective mutants were tested in vivo. Also chosen were: a probable isocitrate lyase (aceAB), a gene involved in mycobactin/exocholin synthesis (mbtH2), a possible conserved lipoprotein (lpqP), as well as putative transcriptional regulators (map0834c and map1634).

TABLE 5

Characterization of transposon mutants tested in the mouse model of paratuberculosis

| Gene | Insertion %* | Known molecular function |
|---|---|---|
| mmpL10 | 18.6 | Conserved transmembrane transport protein |
| fprA | 56.5 | Adrenodoxin-oxidoreductase |
| papA2 | 12.1 | Conserved polyketide synthase associated protein |
| gcpE | 56.8 | Isoprenoid biosynthesis, 4-hydroxy-3-methylbut-2-en-1-yl diphosphate synthase |
| papA3_1 | 65.2 | Probable conserved polyketide synthase associated protein |
| kdpC | 45.1 | Probable Potassium-transporting ATPase C chain |
| umaA1 | 63.5 | Possible mycolic acid synthase |
| pstA | 3.8 | Non-ribosomal binding peptide synthetase |
| fabG2_2 | 70.1 | Putative oxidoreductase activity |
| trpE2 | 81.2 | Probable anthranilate synthase component I |
| impA | 52.0 | Probable inositol-monophosphatase |
| cspB | 63.8 | Small cold shock protein |
| aceAB | 95.5 | Probable isocitrate lyase |
| mbtH2 | 64.6 | mbtH_2 protein family, mycobactin/exocholin synthesis |
| lpqP | 1.6 | Possible conserved lipoprotein |
| prrA | 83.6 | Transcriptional regulatory, putative two-component system regulator |
| map1634 | 88.8 | Transcription factor activity |
| lipN** | deletion | Lipase, esterase protein |

*Insertion % indicates the percentage from start codon of gene.
**lipN mutant was generated by homologous recombination.

Before animal infection, the growth curve of all mutants in Middlebrook 7H9 broth supplemented with kanamycin was shown to be similar to that of the parent strain. However, most mutants reached an $OD_{600}$=1.0 at 35 days compared to 25 days for the ATCC19698, parent strain, which could be attributed to the presence of kanamycin in the growth media. Once mycobacterial strains reached $OD_{600}$=1.0, they were appropriately diluted and prepared for intraperitoneal (IP) inoculation of $10^7$-$10^8$ CFU/mouse. In each case, the bacterial colonization and the nature of histopathology induced post-challenge were compared to the parent strain of *M. paratuberculosis* inoculated at similar infectious dose.

FIG. 3 shows colonization levels of variable *M. paratuberculosis* strains to mice organs. Groups of mice were infected via intraperitoneal injection ($10^7$-$10^8$ CFU/mouse) with the wild-type strain (ATCC19698) or one of 11 mutants. Colonization by only 8 mutants is shown in liver (A), spleen (B) and intestine (C) after 3, 6 and 12 weeks post infection. Bars represent the standard errors calculated from the mean of colony counts estimated from organs at different times post infection.

Figures 3A, 3B, 3C:
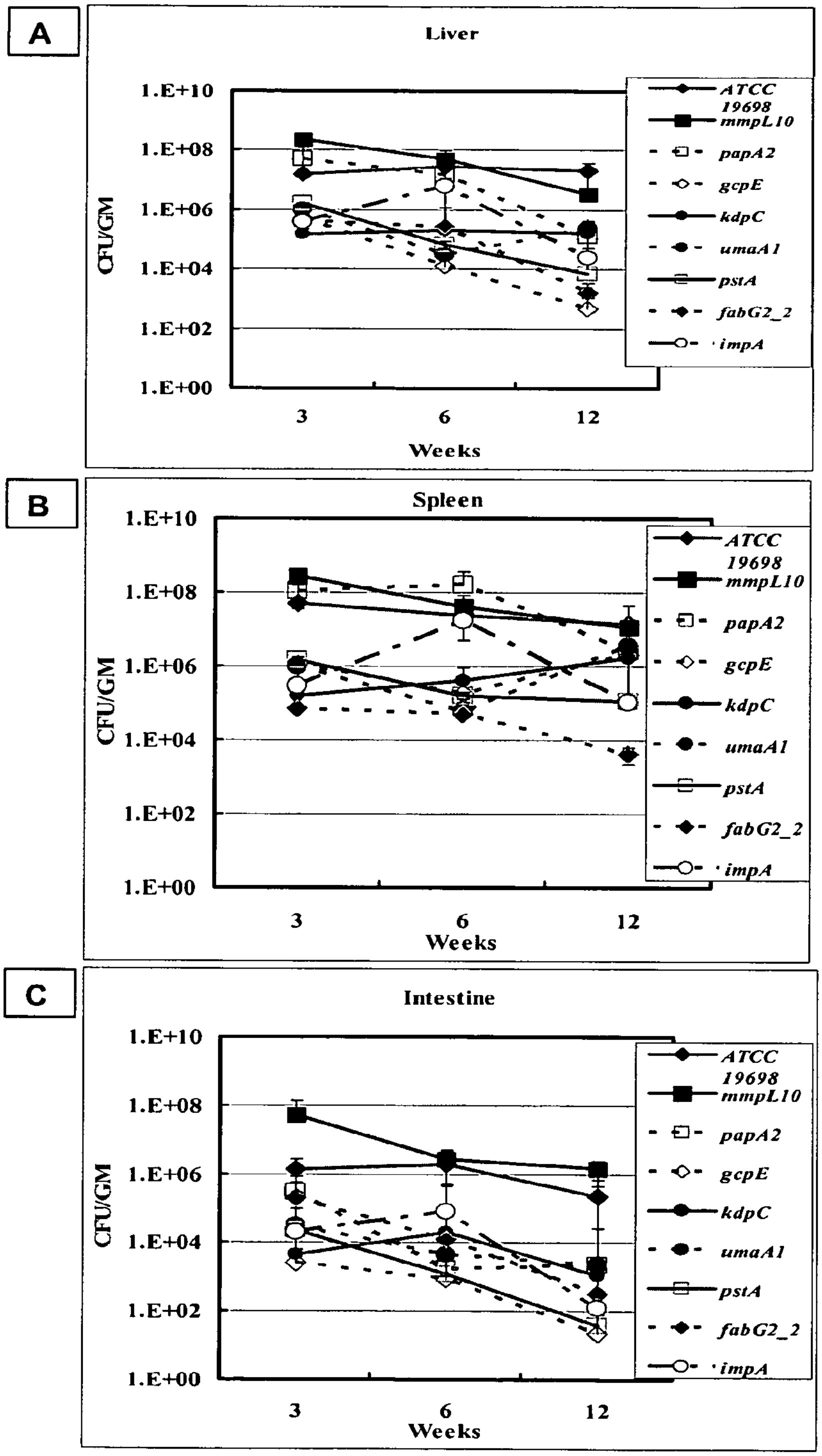
FIGS. 3A-3C depict charts showing intestinal colonization levels of variable *M. paratuberculosis* strains to different mice organs.

All challenged mice were monitored for 12 weeks post infection with tissue sampling at 3, 6 and 12 weeks post infection. For samples collected at 3 weeks post-infection, only the strains with a disruption in gcpE or kdpC genes displayed significantly ($p<0.05$) lower colonization levels compared to the parent strain (FIG. 3), especially in the primary target of *M. paratuberculosis*, the intestine. Some of the mutants (gcpE and kdpc) displayed a significant reduction in the intestinal colony counts starting from 3 weeks post infection and throughout the experiment. At 6 weeks post infection, both papA2 and pstA mutants showed significant colony reduction in the intestine that was maintained in the later time point. At 12 weeks post infection, umaA1, fabG2_2, and impA genes displayed significantly decreased colonization in the intestine ($p<0.05$) with a reduction of at least 2 logs (FIG. 3C). Colonization levels of the spleen did not show a significant change while levels in the liver and intestine were variable between mutants and wild-type and therefore, they were the most informative organs (FIG. 3).

The four mutants mmpL 10, fprA, papA3_1, and trpE2 showed a 10-fold reduction in mycobacterial levels at least in one examined organ by 12 weeks post infection although, this reduction was not statistically significant ($p>0.05$).

Figures 4A, 4B:
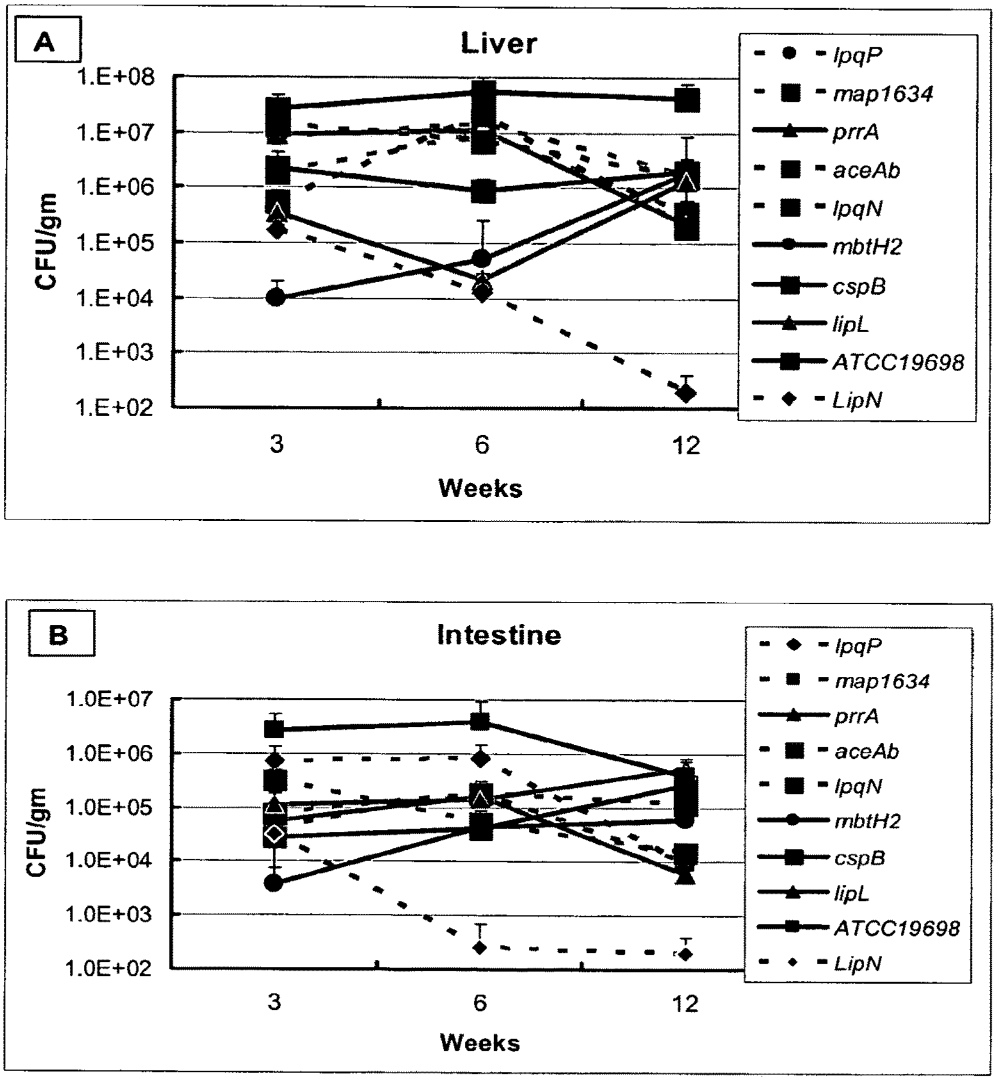
FIGS. 4A-4B depict charts showing liver and intestinal colonization levels of variable *M. paratuberculosis* strains to different mice organs.

Additional mutants with colonization levels significantly lower in both intestine and liver were identified. Shown in FIG. 4 are data obtained using attenuated mutants with disruption in one of aceAB, mbtH2, lpqP, map0834c, cspB, lipN, or map1634 genes. The graph in FIG. 4A depicts liver colonization of BALB/c mice following infection with $10^8$ CFU/animal of *M. paratuberculosis* mutants compared to the wild type strain ATCC19698. IP injection was used as a method for infection. Colonization levels in the liver over 3, 6, and 12 weeks post infection were monitored and are shown in FIG. 4A. The graph in FIG. 4B depicts intestinal colonization of BALB/c mice following infection with $10^8$ CFU/animal of *M. paratuberculosis* mutants compared to the wild type strain ATCC19698. IP injection was used as a method for infection. Colonization levels in the intestine over 3, 6, and 12 weeks post infection were monitored and are shown in FIG. 4B.

Histopathology of Mice Infected with Transposon Mutants

All animal groups infected with mutants or the parent strain displayed a granulomatous inflammatory reaction consistent with infection with *M. paratuberculosis* using the mouse model of *paratuberculosis*. Liver sections were the most reflective organ for *paratuberculosis* where a typical granulomatous response was found. It was exhibited as aggregation of lymphocytes surrounded with a thin layer of fibrous connective tissues.

Figure 5:
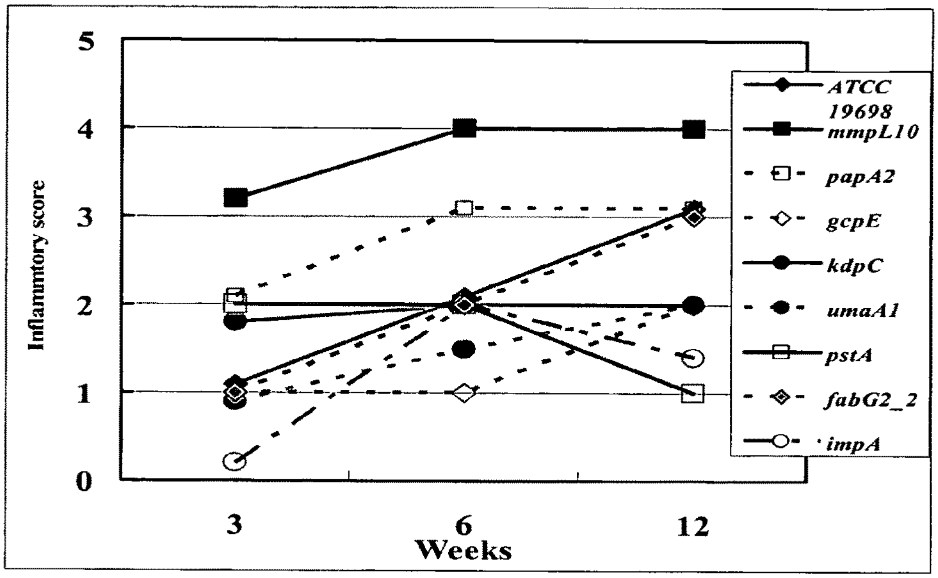
FIG. 5 depicts a chart showing the histopathology of mice infected with *M. paratuberculosis* strains.

FIG. 5 shows histopathological data from liver of mice infected with *M. paratuberculosis* strains as outlined in FIG. 3. At 3, 6 and 12 weeks post infection, mice were sacrificed and liver, spleen, and intestine were processed for histopathological examination. Liver sections stained with H&E with arrows indicating granulomatous inflammatory responses were shown in FIG. 4 of U.S. Provisional Patent Application Ser. No. 60/749,128, incorporated herein by reference. FIG. 5 is a chart showing the inflammatory scores of all mice groups.

Granuloma formation was apparent in animals infected with ATCC19698 strain and some mutants such as ΔmmpL10. Both the size and number of granulomas were increased over time indicating the progression of the disease. During early times of infection (3 and 6 weeks sampling), most mutants displayed only lymphocytic inflammatory responses while the formation of granulomas was observed only at the late time (12 weeks samples). Additionally, the severity of inflammation reached level 3 (out of 5) at 12 weeks post-infection for mice infected with ATCC19869 while in the group infected with mutants such as ΔgcpE and ΔkdpC, the granulomatous response was lower (ranged between levels 1 and 2).

When mice infected with ΔmmpL10 were examined, the lymphocyte aggregates were larger in size and were well-separated by fibrous tissues compared to the granuloma formed in mice infected with the ATCC19698. On the other hand, some mutants (e.g. ΔgcpE, ΔimpA) began with relatively minor lesions and remained at this level as time progressed while others (Δpap3_1, fabG2_2) started with mild lesions and progressively increased in severity over time.

A third group of mutants (ΔfprA, ΔkdpC) began with a similar level of response to that of the parent strain and continue to be severely affected until the end of the sampling time.

Generally, by combining the histopathology and colonization data it was possible to assess the overall virulence of the examined mutants and classify disrupted genes into 3 classes. In Class I (early growth mutants), the disruption of genes (e.g. gcpE, KdpC) generated mutants that are not able to multiply efficiently in mice tissues and therefore, a modest level of lesions was generated and their colonization levels were significantly lower than that of wild type. In Class II (tissue specific mutants), levels of bacterial colonization were significantly reduced in only specific tissues such as umaA1 for liver and papA2 in the intestine at 6 weeks samples. No characteristic pathology of this group could be delineated since only liver sections were reflective of the *paratuberculosis* using the mouse model employed in this study. In Class III (persistence mutants), levels of colonization were maintained unchanged in the first 6 weeks and then reduced significantly at later times (e.g. fabG2_2 and impA). The lesions formed in animals infected with Class III mutants showed a similar pattern of lesion progression to those of animals infected with the parent strain.

Generally, there was an inverse relationship between granuloma formation scores and mycobacterial colonization levels of mutants for samples collected at 12 weeks post infection. The decline of *M. paratuberculosis* levels could be attributed to the initiation of a strong immune response represented by an increase of granuloma formation. However, in the case of animals infected with ΔpstA and ΔimpA, the decline of colonization level was consistent with the reduction in granuloma scores.

Overall, large scale characterization of mutant libraries for virulence determinants is shown to be possible, especially when the genome sequence of a given genome is known. The employed approach can be applied in other bacterial systems where there is little information available on pathogen virulence determinants.

Histopathological analyses of mice infected with the attenuated *M. paratuberculosis* mutants aceAB, mbtH2, lpqP, map0834c, cspB, lipN, or map1634 showed a decrease in granuloma formation in the liver, compared to the mice infected with the wild type *M. paratuberculosis* strain ATCC19698.

Characterization of Transposon Mutants

The list of diagnostic targets, i.e., potential virulence determinants disclosed here includes the gcpE gene encoding a product that controls a terminal step of isoprenoid biosynthesis via the mevalonate independent 2-Cmethyl-D-erythritol-4-phosphate (MEP) pathway. Because of its conserved nature and divergence from mammalian counterpart, gcpE and its products are considered a suitable target for drug development.

Another diagnostic target, i.e., potential virulence gene, is pstA, which encodes non-ribosomal peptide synthetase in *M. tuberculosis* with a role in glycopeptidolipids (GPLs) synthesis. The GPLs is a class of species-specific mycobacterial lipids and major constituents of the cell envelopes of many non-tuberculous mycobacteria as well, such as *M. smegmatis.*

Disruption of umaA1 also resulted in lower colonization levels in all organs examined at 6 weeks post infection and forward.

Additional potential virulence determinants include papA3_1 and papA2, genes that are members of the polyketide synthase associated proteins family of highly conserved genes. Members of the pap family encode virulence-enhancing lipids. Nonetheless, these two mutants displayed different attenuation phenotypes. The papA2 mutant showed significantly lower CFU than the papA3_1 mutant.

The kdpC gene encodes an inducible high affinity potassium uptake system. The kdpC mutant was significantly reduced mostly in the intestinal tissue at early and late stages of infection.

The impA mutant showed significantly reduced levels at late times of infection indicating that impA may possibly play a role in *M. paratuberculosis* entry into the persistence stage of the infection.

The aceAB mutant showed significantly reduced levels at late times of infection indicating that aceAB may possibly play a role in *M. paratuberculosis* entry into the persistence stage of the infection. Deletion of a homologue of this gene in *M. tuberculosis* rendered this mutant attenuated.

The mbtH2 mutant showed significantly reduced levels at early times of infection indicating that mbtH2 may possibly play a role in *M. paratuberculosis* entry into the intestinal cells or survival in macrophage during early infection. This gene was induced during animal infection using DNA microarrays conducted in the inventor's laboratory.

The lpqP mutant showed significantly reduced levels at late times of infection indicating that lpqP may possibly play a role in *M. paratuberculosis* entry into the persistence stage of the infection.

The prrA mutant showed significantly reduced levels at late times of infection indicating that prrA may possibly play a role in *M. paratuberculosis* entry into the persistence stage of the infection. The prrA homologue in *M. tuberculosis* is two-component transcriptional regulator. This gene was induced at low pH using DNA microarrays conducted in the inventor's laboratory.

The map1634 mutant showed significantly reduced levels at late times of infection indicating that map1634 may possibly play a role in *M. paratuberculosis* entry into the persistence stage of the infection.

The lipN mutant showed significantly reduced levels at mid and late times of infection indicating that lipN may play an important role in *M. paratuberculosis* during early and persistent stages of the infection. LipN encodes a lipase which could be important degrading fatty acids. This gene was induced in cow samples using DNA microarrays conducted in the inventor's laboratory.

Example 2

Bacterial Strains

Mycobacterial isolates (N=34) were collected from different human and domesticated or wildlife animal specimens representing different geographical regions within the USA (Table 6). *Mycobacterium avium* subsp. *paratuberculosis* K10 strain, *M. avium* subsp. *avium* strain 104 (*M. avium* 104) and *M. intracellulare* were obtained from Raul Barletta (University of Nebraska). *M. paratuberculosis* ATCC19698 and other animal isolates were obtained from the Johne's Testing Center, University of Wisconsin-Madison, while the *M. paratuberculosis* human isolates were obtained from Saleh Naser (University of Central Florida). All strains were grown in Middlebrook 7H9 broth supplemented with 0.5% glycerol, 0.05% Tween 80 and 10% ADC (2% glucose, 5% BSA fraction V, and 0.85% NaCl) at 37° C. For *M. paratuberculosis* strains, 2 μg/ml of mycobactin-J (Allied Monitor, Fayette, Mo.) also was added for optimal growth.

TABLE 6

*Mycobacterium* strains tested in Example 2 of the present invention

| Species | Strain | Host | Sample origin | Location |
|---|---|---|---|---|
| *M. avium* subsp. *paratuberculosis* | K10 | Cow | Feces | Wisconsin |
| | ATCC19698 | Cow | Feces | Unknown |
| | JTC33666 | Turkomen markhor (Goat) | Feces | California |
| | JTC33770 | Cow | Feces | Wisconsin |
| | CW303 | Cow | Feces | Wisconsin |
| | 1B | Human | Ileum | Florida |
| | 3B | Human | Ileum | Florida |
| | 4B | Human | Ileum | Florida |
| | 5B | Human | Ileum | Florida |
| | DT3 | British red deer | Feces | Unknown |
| | DT9 | African Eland | Feces | Unknown |
| | DT12 | Chinese Reeve's muntjac (Deer) | Ileum | Unknown |
| | DT19 | White rhino | Feces | Unknown |
| | JTC1281 | Oryx | Lymph Node | Florida |
| | JTC1282 | Cow | Lymph Node | Wisconsin |
| | JTC1283 | Cow | Feces | Georgia |
| | JTC1285 | Goat | Feces | Virginia |
| | JTC1286 | Cow | Ileum | Wisconsin |
| *M. avium* subsp. *avium* | 104 | Human | Blood | Unknown |
| | T93 | Cow | Feces | Texas |
| | T99 | Cow | Feces | Texas |
| | T100 | Cow | Feces | Texas |
| | DT30 | Angolan springbok | Feces | Unknown |
| | DT44 | Formosan Reeve's muntjac (Deer) | Lymph Node | Unknown |

TABLE 6-continued

| *Mycobacterium* strains tested in Example 2 of the present invention | | | | |
|---|---|---|---|---|
| Species | Strain | Host | Sample origin | Location |
| | DT78 | Water buffalo | Ileum | Unknown |
| | DT84 | Lowland wisent | Lymph Node | Unknown |
| | DT247 | Cuvier's gazelle | Lymph Node | Unknown |
| | JTC956 | Ankoli | Feces | Florida |
| | JTC981 | Bongo | Feces | Florida |
| | JTC982 | Nyala | Feces | Florida |
| | JTC1161 | Cow | Feces | Florida |
| | JTC1262 | Bison | Lymph Node | Montana |
| | JTC33793 | Dama gazelle | Feces | Indiana |
| *M. intracellulare* | $mc^2$76 | Human | Sputum | Unknown |

Microarray Design

Oligonucleotide microarrays were synthesized in situ on glass slides using a maskless array synthesizer. Probe sequences were chosen from the complete genome sequence of *M. avium* 104. Sequence data of *M. avium* 104 strain was obtained from The Institute for Genomic Research. Open reading frames (ORFs) were predicted using GeneMark software. For every ORF, 18 pairs of 24-mer sequences were selected as probes. Each pair of probes consists of a perfect match (PM) probe, along with a mismatch (MM) probe with mutations at the 6th and 12th positions of the corresponding PM probes. A total of ~185,000 unique probe sequences were synthesized on derivatized glass slides by NimbleGen Systems (Madison, Wis.).

Genomic DNA Extraction and Labeling

Genomic DNA was extracted using a modified CTAB-based protocol followed by two rounds of ethanol precipitation. For each hybridization, 10 μg of genomic DNA was digested with 0.5 U of RQ1 DNase (Promega, Madison, Wis.) until the fragmented DNA was in the range of 50-200 bp (examined on a 2% agarose gel). The reaction was stopped by adding 5 μl of DNase stop solution and incubating at 90° C. for 5 minutes. Digested DNA was purified using YM-10 microfilters (Millipore, Billerica, Mass.).

Genomic DNA hybridizations were prepared by an end-labeling reaction. Biotin was added to purified mycobacterial DNA fragments (10 μg) using terminal deoxynucleotide transferase in the presence of 1 μM of biotin-N6-ddATP at 37° C. for 1 hr. Before hybridization, biotin-labeled gDNA was heated to 95° C. for 5 minutes, followed by 45° C. for 5 minutes, and centrifuged at 14,000 rpm for 10 minutes before adding to the microarray slide.

After microarray hybridization for 12-16 hrs, slides were washed in non-stringent (6×SSPE and 0.01% Tween-20) and stringent (100 mM MES, 0.1 M NaCl, and 0.01% Tween 20) buffers for 5 min each, followed by fluorescent detection by adding Cy3 streptavidin (Amersham Biosciences Corp., Piscataway, N.J.). Washed microarray slides were dried by argon gas and scanned with an Axon GenPix 4000B (Axon Instrument, Union City, Calif.) laser scanner at 5 μm resolution. Replicate microarrays were hybridized for every genome tested. Two hybridizations of the same genomic DNA with high reproducibility (correlation coefficient >0.9) were allowed for downstream analysis.

Data Analysis and Prediction of Genomic Deletions

The images of scanned microarray slides were analyzed using specialized software (NimbleScan) developed by NimbleGen Systems. The average signal intensity of a MM probe was subtracted from that of the corresponding PM probe. The median value of all PM-MM intensities for an ORF was used to represent the signal intensity for the ORF. The median intensities value for each slide was normalized by multiplying each signal by a scaling factor that was 1000 divided by the average of all median intensities for that array.

To compare hybridization signals generated from each of the genomes to that of *M. avium* 104, the normalized data from replicate hybridizations were exported to R language program with the EBarrays package version 1.1, which employs a Bayesian statistical model for pair-wise genomic comparisons using a log-normal-normal model. Genes with the probability of differential expression larger than 0.5 were considered significantly different between the genomes of *M. avium* and *M. paratuberculosis.*

The hybridization signals corresponding to each gene of all investigated genomes were plotted according to genomic location of *M. avium* 104 strain using the GenVision software (DNAStar Inc., Madison, Wis.). The same data set was also analyzed by MultiExperiment Viewer 3.0 to identify common cluster patterns among mycobacterial isolates.

Microarray Analysis of *M. avium* and *M. paratuberculosis* Genomes

Genomic rearrangements among *M. avium* and *M. paratuberculosis* isolated from variable hosts were investigated, to identify diagnostic targets for microbial infection. The analysis began using 5 mycobacterial isolates employing DNA microarrays and was expanded to include an additional 29 isolates employing a more affordable technology of PCR followed by direct sequencing. All of the isolates were collected from human and domesticated or wildlife animal sources and had been previously identified at the time of isolation using standard culturing techniques for *M. avium* and *M. paratuberculosis*. The identity of each isolate was confirmed further by acid-fast staining and positive PCR amplification of IS900 sequences from all *M. paratuberculosis*. Additionally, the growth of all *M. paratuberculosis* isolates were mycobactin-J dependent while all *M. avium* isolates were not.

Before starting the microarray analysis, an hsp65 PCR typing protocol was performed to ensure the identity of each isolate. The PCR typing protocol agreed with earlier characterization of all mycobacterial isolates used throughout this study. FIG. 5A of U.S. Provisional Patent Application Ser. No. 60/749,128, incorporated by reference, depicts the PCR confirmation of the identity of the examined genomes.

To investigate the extent of variation among *M. avium* and *M. paratuberculosis* on a genome-wide scale, oligonucleotide microarrays were designed from the *M. avium* 104 strain genome sequence. The GeneMark algorithm was used to predict potential ORFs in the raw sequence of *M. avium* genome obtained from TIGR. A total of 4987 ORFs were predicted for *M. avium* compared to 4350 ORFs predicted in

*M. paratuberculosis*. Relaxed criteria for assigning ORFs were chosen (at least 100 bp in length with a maximal permitted overlap of 30 bases between ORFs) to use a comprehensive representation of the genome to construct DNA microarrays.

Similar to other bacterial genomes, the average ORF length was ~1 Kb. Using the ASAP comparative genomic software suite, the ORFs shared by *M. paratuberculosis* and *M. avium* had an average percent identity of 98%, a result corroborated by others. BLAST analysis of the ORFs from both genomes show that about 65% (N=2557) of the genes have a significant match (E<10-10) in the other genome.

To test the reliability of genomic DNA extraction protocols and microarray hybridizations, the signal intensities of replicate hybridizations of the same mycobacterial genomic DNA were compared using scatter plots. ORFs with positive hybridization signals in at least 10 probe pairs were normalized and used for downstream analysis to ensure the inclusion of only ORFs with reliable signals. In all replicates, independently isolated hybridized samples of gDNA had high correlation coefficients (r>0.9).

To investigate the genomic relatedness among isolates compared to the *M. avium* 104 strain, a hierarchical cluster analysis was used to assess the similarity of the hybridization signals among isolates on a genome-wide level. FIG. 5C of U.S. Provisional Patent Application Ser. No. 60/749,128, incorporated by reference, shows a dendogram displaying the overall genomic hybridization signals generated from biological replicates of different mycobacterial isolates from animal or human (HU) sources.

Within the *M. paratuberculosis* cluster, the human and the clinical animal isolates were highly similar to each other than to the ATCC19698 reference strain, implying a closer relatedness between human and clinical isolate of *M. paratuberculosis*. Interestingly, despite the high degree of similarity between genes shared among isolates, hundreds of genes appeared to be missing from different genomes relative to *M. avium* genome. Most of the genes were found in clusters in the *M. avium* 104 genome, the reference strain used for designing the microarray chip. Consequently, regions absent in *M. avium* 104 but present in other genomes could not be identified in this analysis.

PCR Verification and Sequence Analysis

To confirm the results predicted by microarray hybridizations, a 3-primer PCR protocol was used to amplify the regions flanking predicted genomic islands. For every island, one pair of primers (F—forward and R1—reverse 1) was designed upstream of the target region and a third primer (R2—reverse 2) was designed downstream of the same region. The primers were designed so that expected lengths of the products were less than 1.5 Kb between F and R1 and less than 3 Kb between F and R2 when amplified from the genomes with the deleted island. Each PCR contained 1 M betaine, 50 mM potassium glutamate, 10 mM Tris-HCl pH 8.8, 0.1% of Triton X-100, 2 mM of magnesium chloride, 0.2 mM dNTPs, 0.5 μM of each primer, 1 U Taq DNA polymerase and 15 ng genomic DNA. The PCR cycling condition was 94° C. for 5 minutes, followed by 30 cycles of 94° C. for 1 minute, 59° C. for 1 minute and 72° C. for 3 minutes.

All PCR products were examined using 1.5% agarose gels and stained with ethidium bromide. To further confirm sequence deletions, amplicons flanking deleted regions were sequenced using standard Big Dye® Terminator v3.1 (Applied Biosystems, Foster City, Calif.) and compared to the genome sequence of *M. paratuberculosis* or *M. avium* using BLAST alignments.

Large Genomic Deletions Among *M. avium* and *M. paratuberculosis* Isolates

To better analyze the hybridization signals generated from examined genomes, a Bayesian statistical principle (EBarrays package) was used to compare the hybridization signals generated from different isolates relative to the signals generated from *M. avium* 104 genome. The Bayesian analysis estimates the likelihood of observed differences in ORF signals for each gene between each isolate and the *M. avium* 104 reference strain.

Figures 6A, 6B:
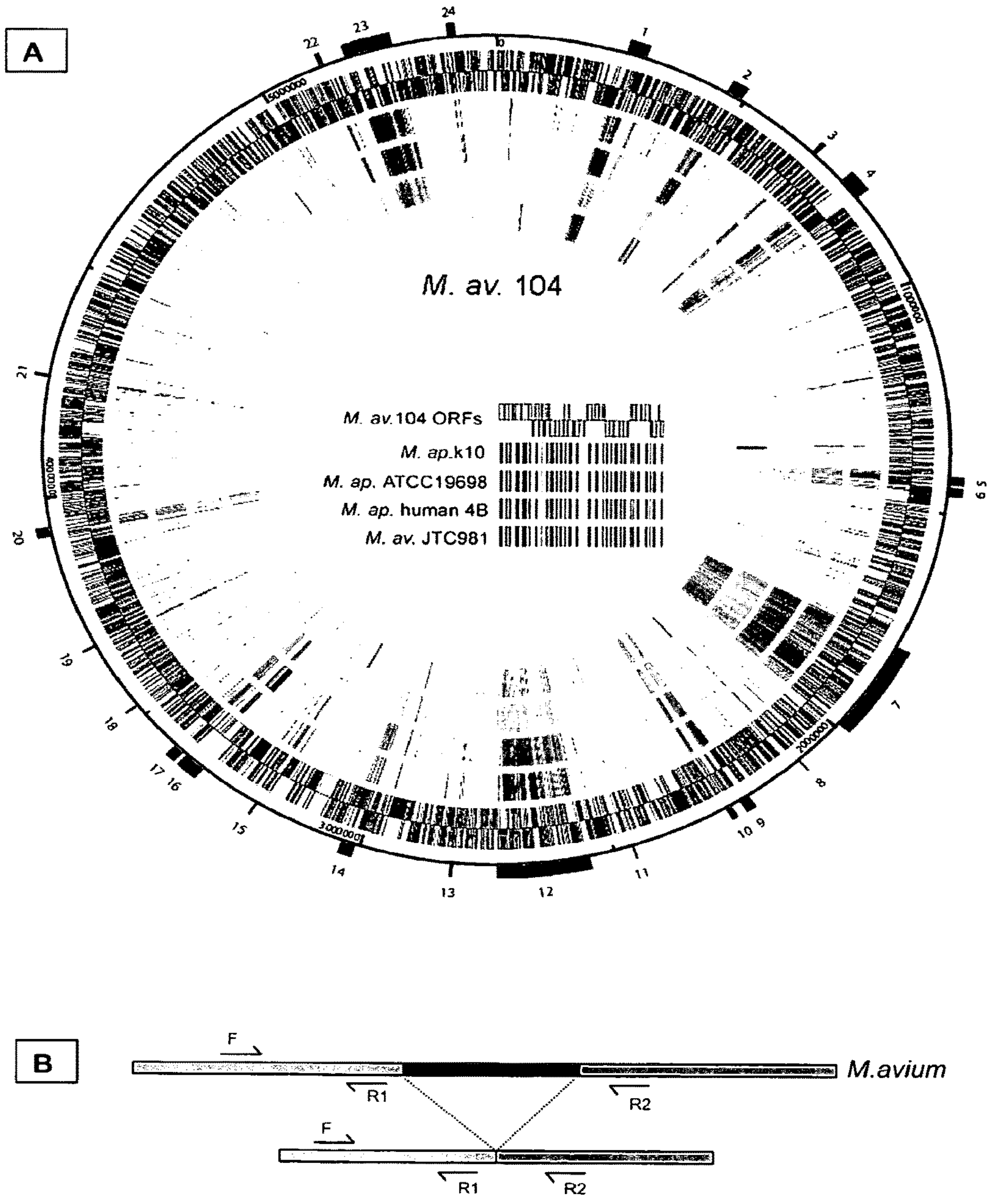
FIGS. 6A-6B is a genomic map showing the identification of genomic islands in the *M. avium* genome (A), and a map showing the strategy used for design of PCR primers to confirm the genomic island deletions (B).

FIG. 6A depicts a genome map based on *M. avium* sequence displaying GIs deleted in the examined strains as predicted by DNA microarrays. Inner circles denote the microarray hybridization signals for each examined genome (see legend in center). The outermost dark boxes denote the location of all GIs associated with *M. avium*. A large number of differences were seen among isolates, including many ORFs scattered throughout the genome.

PCR and sequencing were used to confirm deletions identified by microarrays. FIG. 6B depicts a diagram illustrating the PCR and sequence-based strategy implemented to verify the genomic deletions. Three primers for each island were designed including a forward (F) and 2 reverse primers. When regions included 3 or more consecutive ORFs, they were defined as a genomic island (GI) regardless of the size. Applying such criterion for genomic islands (GIs), 24 islands were present in *M. avium* 104 but absent from all *M. paratuberculosis* isolates, regardless of the source of the *M. paratuberculosis* isolates (animal or human). The GIs ranged in size from 3 to 196 Kb (Table 7) with a total of 846 Kb encoding 759 ORFs. Interestingly, a clinical strain of *M. avium* (JTC981) was also missing 7 GIs (nearly 518 Kb) in common with all *M. paratuberculosis* isolates, in addition to the partial absence of 5 other GIs. This variability indicated a wide-spectrum of genomic diversity among *M. avium* strains that was not evident among *M. paratuberculosis* isolates.

To confirm the absence of GI regions from isolates, a strategy based on PCR amplification of the flanking regions of each GI was used, followed by sequence analysis to confirm the missing elements. Because the size of most of the genomic island regions exceeds the length of the amplification capability of a typical PCR reaction, 3 primers for each island were designed, including one forward and 2 reverse primers (FIG. 6B). This strategy was successfully applied on 21 genomic islands, while amplification from the rest of the islands (N=3) was not possible due to extensive genomic rearrangements.

FIG. 7 depicts the synteny of *M. avium* and *M. paratuberculosis* genomes.

PCR confirmation of genomic deletions was performed. For example, amplicons from *M. avium*-specific islands #5, 8, 11, 18 and 20 were obtained using DNA templates from 5 different isolates of *M. avium*. Additionally, PCR analysis of the distribution of *M. paratuberculosis*-specific island #1 was performed within 21 clinical isolates of *M. avium* and *M. paratuberculosis*. Electrophoresed DNA samples showed PCR confirmations of the genomic deletions.

Overall, the PCR and sequencing verified the GI content as predicted by comparative genomic hybridizations (Table 7). The success of this strategy in identifying island deletions provided a protocol to examine several clinical isolates that could not be otherwise analyzed by costly DNA microarrays.

TABLE 7

List of genomic regions that displayed different hybridization signals using DNA microarrays designed from the genome of *M. avium* 104 strain

| Island Number | Start (bp)[a] | End (bp)[a] | *M. parat.* K10[b] | *M. parat.* 19698 | *M. parat.* human | *M. avium* JTC981 | PCR and sequence confirmation[c] |
|---|---|---|---|---|---|---|---|
| 1 | 254,394 | 294,226 | – | – | – | – | Yes |
| 2 | 461,414 | 492,800 | – | – | – | – | Yes |
| 3 | 666,033 | 675,725 | – | – | – | – | Yes |
| 4 | 747,095 | 794,450 | – | – | – | – | Yes |
| 5 | 1,421,722 | 1,439,626 | – | – | – | + | Yes |
| 6 | 1,444,205 | 1,463,365 | – | – | – | + | Yes |
| 7 | 1,795,281 | 1,991,691 | – | – | – | +/– | Yes |
| 8 | 2,097,907 | 2,100,883 | – | – | – | – | Yes |
| 9 | 2,220,320 | 2,241,163 | – | – | – | +/– | Yes |
| 10 | 2,259,120 | 2,271,610 | – | – | – | – | Yes |
| 11 | 2,462,693 | 2,466,285 | – | – | – | + | Yes |
| 12 | 2,549,555 | 2,730,999 | – | – | – | – | ND |
| 13 | 2,815,625 | 2,821,149 | – | – | – | + | Yes |
| 14 | 3,008,716 | 3,036,980 | – | – | – | + | Yes |
| 15 | 3,214,820 | 3,219,550 | – | – | – | + | ND |
| 16 | 3,340,393 | 3,384,549 | – | – | – | + | Yes |
| 17 | 3,392,586 | 3,413,804 | – | – | – | + | ND |
| 18 | 3,523,417 | 3,527,334 | – | – | – | +/– | Yes |
| 19 | 3,670,518 | 3,675,686 | – | – | – | + | Yes |
| 20 | 3,917,752 | 3,939,034 | – | – | – | +/– | Yes |
| 21 | 4,254,594 | 4,261,488 | – | – | – | +/– | Yes |
| 22 | 5,122,371 | 5,132,301 | – | – | – | + | Yes |
| 23 | 5,174,641 | 5,270,187 | – | – | – | + | Yes |
| 24 | 5,378,903 | 5,395,102 | – | – | – | + | Yes |

[a]Coordinates of start and end of island based on the genome sequence of *M. avium* strain 104.
[b]+ or – denotes presence or absence of genomic regions in examined genomes while +/– denotes incomplete deletion.
[c]NO—not done.

Bioinformatic Analysis of Genomic Islands

Pair-wise BLAST analysis of the genome sequences of *M. avium* 104 and *M. paratuberculosis* K10 was used to further refine the ability to detect genomic rearrangements, especially for regions present in *M. paratuberculosis* K10 genome but deleted from *M. avium* 104 genome. The pair-wise comparison allowed to better analyze the flanking sequences for each GI and to characterize the mechanism of genomic rearrangements among examined strains.

BLAST analysis (E scores >0.001 and <25% sequence alignment between ORFs) correctly identified the deleted GIs where ORFs of *M. avium* were missing in *M. paratuberculosis* detected by using the comparative genomic hybridization protocol. A large proportion of ORFs in each genome (>75%) are likely orthologous (>25% sequence alignment of the ORF length and >90% sequence identity at nucleotide level). This high degree of similarity between orthologues indicates a fairly recent ancestor. Looking for consecutive ORFs from *M. paratuberculosis* that do not have a BLAST match in *M. avium* identified sets of ORFs representing 18 GIs comprising 240 Kb that are present only in *M. paratuberculosis* genome (Table 8).

Genes encoded within *M. avium* and *M. paratuberculosis* specific islands were analyzed by BLASTP algorithm against the GenPept database (Oct. 19, 2004 release) to identify their potential functions. The BLAST results allowed the assignment of signature features to each island. As detailed in Tables 8 and 9, with the presence of a large number of ORFs encoding mobile genetic elements (e.g. insertion sequences and prophages), several ORFs encode transcriptional regulatory elements, especially from TetR-family of regulators. The polymorphism in TetR regulators could be attributed to their sequences allowing them to be amenable for rearrangements. Alternatively, it is possible that the bacteria are able to differentially acquire specific groups of genes suitable for a particular microenvironment.

Further analysis of the GIs identified islands in both *M. avium* and *M. paratuberculosis* (such as MAV-7, MAV-12 and MAP-13) encoding different operons of the mce (mammalian cell entry) sequences that were shown to participate in the pathogenesis of *M. tuberculosis*. Another island (MAV-17) encodes the drrAB operon for antibiotic resistance, which is a well-documented problem for treating *M. avium* infection in HIV patients. The GC % of the majority of *M. paratuberculosis* specific islands (11/18) was at least 5% less than the average GC % of the *M. paratuberculosis* genome (69%) compared to only 3 GIs (out of 24) specific for *M. avium* genome (Table 9) with lower than average GC %.

TABLE 8

*M. paratuberculosis*-specific (MAP) genomic islands deleted in *M. avium* genome

| Island Number | No. of ORFs | GC % | Island Type | Size (bp) | Signature Features |
|---|---|---|---|---|---|
| MAP-1 | 17 | 63.90 | I | 19,343 | Transposition and TetR-family transcriptional regulator genes |
| MAP-2 | 3 | 60.43 | I | 3,858 | Conserved hypothetical proteins |

TABLE 8-continued

| *M. paratuberculosis*-specific (MAP) genomic islands deleted in *M. avium* genome | | | | | |
|---|---|---|---|---|---|
| Island Number | No. of ORFs | GC % | Island Type | Size (bp) | Signature Features |
| MAP-3 | 3 | 66.16 | I | 2,915 | Formate dehydrogenase alpha subunit |
| MAP-4 | 17 | 60.66 | I | 16,681 | Transposition, unknown genes and a possible prophage |
| MAP-5 | 12 | 69.56 | I | 14,191 | Transposition and oxidoreductase genes, PPE family domain protein |
| MAP-6 | 6 | 57.73 | II | 8,971 | Variable genes such as drrC |
| MAP-7 | 6 | 67.26 | II | 6,914 | Transcriptional regulator psrA and biosynthesis genes |
| MAP-8 | 8 | 61.59 | II | 7,915 | TetR-family transcriptional regulator and unknown genes |
| MAP-9 | 10 | 65.49 | II | 11,202 | Transposition, metabolic and TetR-family transcriptional regulator genes |
| MAP-10 | 3 | 66.68 | II | 2993 | Biosynthesis of cofactors, prosthetic groups, and carriers transcriptional regulator, TetR family domain protein |
| MAP-11 | 4 | 62.89 | I | 2,989 | Serine/threonine protein kinase and glyoxalase genes |
| MAP-12 | 11 | 61.08 | I | 11,977 | Transposition, iron metabolism genes and a prophage |
| MAP-13 | 19 | 66.01 | II | 19,977 | TetR-family transcript. regulator and mce family proteins |
| MAP-14 | 19 | 65.76 | II | 19,315 | Possible prophage and unknown proteins |
| MAP-15 | 3 | 62.93 | I | 4,143 | Unknown proteins and a prophage function genes |
| MAP-16 | 56 | 64.32 | I | 79,790 | Transposition and iron regulatory genes |
| MAP-17 | 5 | 61.60 | I | 3,655 | Unknown proteins and a multi-copy phage resistance gene |
| MAP-18 | 3 | 60.36 | I | 3,512 | Hypothetical proteins |
| Total | 204 | | | 239,969 | |

TABLE 9

| Characteristics of *M. avium*-specific (MAV) genomic islands | | | | | |
|---|---|---|---|---|---|
| Island Number | No. of ORFs | GC % | Island Type | Size (bp) | Signature Features |
| MAV-1 | 38 | 68.93 | I | 39,833 | Eukaryotic genes with an integrase gene |
| MAV-2 | 32 | 65.87 | I | 31,387 | Transposition and *M. tuberculosis* genes |
| MAV-3 | 10 | 63.34 | I | 9,693 | Insertion sequence and *M. tuberculosis* or *M. avium* genes |
| MAV-4 | 53 | 66.83 | I | 47,356 | PPE family and eukaryotic genes |
| MAV-5 | 16 | 64.10 | I | 17,905 | Transposition and insertion sequences genes |
| MAV-6 | 23 | 68.80 | I | 19,161 | Transposition, transcript. regulator and heavy metal resistance genes |
| MAV-7 | 187 | 65.50 | II | 196,411 | Transposition, transcript. regulators, cell entry, iron regulation genes |
| MAV-8 | 3 | 65.18 | I | 2,977 | Transposition and transcriptional regulator genes |
| MAV-9 | 15 | 62.43 | I | 20,844 | Transposition and type III restriction system endonuclease genes |
| MAV-10 | 12 | 63.87 | I | 12,491 | Transposition genes |
| MAV-11 | 5 | 65.45 | I | 3,593 | Reductases and hypothetical proteins |
| MAV-12 | 168 | 65.05 | II | 181,445 | Transposition, transcriptional regulators and cell entry genes |
| MAV-13 | 7 | 67.78 | II | 5,525 | Transcriptional regulator |
| MAV-14 | 26 | 67.32 | I | 28,265 | Transposition and *M. tuberculosis* genes |

TABLE 9-continued

| Characteristics of *M. avium*-specific (MAV) genomic islands | | | | | |
|---|---|---|---|---|---|
| Island Number | No. of ORFs | GC % | Island Type | Size (bp) | Signature Features |
| MAV-15 | 3 | 64.12 | II | 4,731 | *Streptomyces* and *M. leprae* genes |
| MAV-16 | 6 | 69.64 | I | 44,157 | Transposition and Pst genes |
| MAV-17 | 20 | 65.23 | II | 21,219 | Transposition and drrAB genes (antibiotic resistance) |
| MAV-18 | 4 | 68.13 | I | 3,918 | Transcriptional regulator and *Streptomyces* genes |
| MAV-19 | 4 | 65.30 | I | 5,169 | Transposition genes |
| MAV-20 | 15 | 63.93 | I | 21,283 | Transposition, transcriptional regulator and membrane-protein genes of *M. tuberculosis* |
| MAV-21 | 8 | 65.93 | I | 6,895 | Transposition and antigen genes |
| MAV-22 | 9 | 67.71 | I | 9,931 | Transcriptional regulator and metalloprotease genes |
| MAV-23 | 77 | 64.08 | I | 95,547 | Transposition, transcript, regulators, secreted proteins, cell entry genes |
| MAV-24 | 18 | 70.25 | I | 16,200 | Hypothetical and unknown proteins from *M. tuberculosis* and *Streptomyces* |
| Total | 759 | | | 845,936 | |

Genomic Deletions Among Field Isolates of *M. avium*

Microarrays and PCR analysis of 5 mycobacterial isolates identified the presence of variable GIs between *M. avium* and *M. paratuberculosis* genomes. To analyze the extent of such variations among clinical isolates circulating in both human and animal populations, PCR and a sequencing-based strategy were used to examine 28 additional *M. avium* and *M. paratuberculosis* isolates collected from different geographical locations within the USA (Table 6). An additional isolate of *M. intracellulare* was included as a representative strain that belongs to the MAC group but not a subspecies of *M. avium.*

For PCR amplification, GIs spatially scattered throughout the *M. avium* and *M. paratuberculosis* genomes were examined (Tables 10, 11) to identify any potential rearrangements in all quarters of the genome. Because of the wide-spectrum diversity observed among *M. avium* genomes, 4 GIs (MAV-3, 11, 21 and 23) were chosen to assess genomic rearrangements in clinical isolates. Because of the limited diversity observed among *M. paratuberculosis* genomes, a total of 6 *M. paratuberculosis*-specific GIs (MAP-1, 3, 5, 12, 16 and 17) were chosen for testing genomic rearrangements. As suggested from the initial comparative genomic hybridizations, clinical isolates of *M. paratuberculosis* showed a limited diversity in the existence of *M. avium*-specific islands (DT9 clinical isolate from a red deer) indicating the clonal nature of this organism (Table 10).

To the contrary, *M. avium* isolates showed a different profile from both *M. avium* 104 and *M. avium* JTC981 indicating extensive variability within *M. avium* isolates. A similar pattern of genomic rearrangements was observed when *M. paratuberculosis*-specific GIs were analyzed using *M. avium* and *M. paratuberculosis* isolates (Table 11). Most of the *M. paratuberculosis* clinical isolates with deleted GIs were from wildlife animals suggesting that strains circulating in wildlife animals could provide a potential source for genomic rearrangements in *M. paratuberculosis.*

TABLE 10

PCR identification of selected MAV-island regions from 29 clinical isolates of *M. paratuberculosis* and *M. avium* collected from different states

| | | Genomic island | | | |
|---|---|---|---|---|---|
| Clinical Isolate | Subspecies | MAV-3 | MAV-11 | MAV-21 | MAV-23 |
| JTC33666 | *M. paratuberculosis* | − | − | − | − |
| JTC33770 | *M. paratuberculosis* | − | − | − | − |
| CW303 | *M. paratuberculosis* | − | − | − | − |
| 1B | *M. paratuberculosis* | − | − | − | − |
| 3B | *M. paratuberculosis* | − | − | − | − |
| 4B | *M. paratuberculosis* | − | − | − | − |
| 5B | *M. paratuberculosis* | − | − | − | − |
| DT3 | *M. paratuberculosis* | − | − | − | − |
| DT9 | *M. paratuberculosis* | + | N/A | − | − |
| DT12 | *M. paratuberculosis* | − | − | − | − |
| DT19 | *M. paratuberculosis* | − | − | − | − |
| JTC1281 | *M. paratuberculosis* | − | − | − | − |
| JTC1282 | *M. paratuberculosis* | − | − | − | − |
| JTC1283 | *M. paratuberculosis* | − | − | − | − |
| JTC1285 | *M. paratuberculosis* | − | − | − | − |
| JTC1286 | *M. paratuberculosis* | − | − | − | − |
| T93 | *M. avium* | + | − | − | − |
| T99 | *M. avium* | + | − | − | − |
| T100 | *M. avium* | + | + | − | − |
| DT30 | *M. avium* | − | + | + | + |
| DT44 | *M. avium* | − | + | + | + |
| DT78 | *M. avium* | − | + | + | + |
| DT84 | *M. avium* | − | + | − | + |
| DT247 | *M. avium* | − | + | + | + |
| JTC956 | *M. avium* | N/A | N/A | N/A | − |
| JTC982 | *M. avium* | N/A | + | N/A | + |
| JTC1161 | *M. avium* | + | + | − | − |
| JTC1262 | *M. avium* | + | − | − | − |
| JTC33793 | *M. avium* | + | + | + | + |

Symbols(+ or −) denote presence or absence of genomic regions; N/A denotes no amplification of DNA fragments.

Combined with the hierarchical cluster analysis employed on the whole genome hybridizations, PCR and sequence analyses provided more evidence that genomic diversity is quite extensive among *M. avium* strains but much less limited in *M. paratuberculosis.*

Large DNA Fragment Inversions within the Genomes of *M. avium* Subspecies.

Because of the high similarity among the genomes of *M. paratuberculosis* and *M. avium* reported earlier, considerable conservation in the synteny between genomes (gene order) within *M. avium* strains was expected. The order of GIs was used as markers for testing the conserved gene order and the overall genome structure between *M. paratuberculosis* and *M. avium* genomes.

It was unexpectedly discovered that, when the GIs associated with both genomes were aligned, three large genomic fragments in *M. paratuberculosis* were identified as inverted relative to the corresponding genomic fragments in *M. avium*. These fragments had the sizes of approximately 1969.4 Kb, 863.8 Kb, and 54.9 Kb (FIG. 7). The largest inverted region (INV-1) of approximately 1969.4 Kb is flanked by MAV-4 and MAV-19. INV-1 encompasses bases 1075033 through 3044433 of the *M. paratuberculosis* genomic sequence. The second inverted region (INV-2) of approximately 863.8 Kb is flanked by MAV-21 and MAV-24. Located near the origin of replication, INV-2 encompasses bases 3885218 through 4748979 of the *M. paratuberculosis* genomic sequence. The smallest inverted region (INV-3) of approximately 54.9 Kb is flanked by MAV-1 and MAV-2. INV-3 encompasses bases 320484 through 377132 of the *M. paratuberculosis* genomic sequence.

Referring to FIG. 7, the location of genomic islands present in *M. avium* (dark grey boxes numbered 1-24. outer circle) or in *M. paratuberculosis* (light grey boxes numbered 1-18. inner circle) genomes are drawn to scale on the circular map of *M. avium* (outer circle) as well as the map of *M. paratuberculosis* (inner circle). The sequences of *M. paratuberculosis* K10 (query sequence) compared with the whole genome sequence *M. avium* 104 ORFs (target sequence) using BLAST algorithm with cut off values of E>0.001 and alignment percentage <25% of the whole gene were accepted as indications for gene deletion. The numerous short bars represent predicted ORFs in forward (outermost) or reverse (innermost) orientations. Large arrows indicate sites of genomic inversions.

Because the bioinformatics analysis used raw genome sequences, PCR and sequencing approach were used to substantiate the genomic inversions in 7 mycobacterial isolates (3 isolates of *M. avium* and 4 isolates of *M. paratuberculosis*). As predicted from the initial sequence analysis, primers flanking the junction sites of the inverted regions gave the correct DNA fragment sizes and orientations consistent with the sequence of *M. avium* and *M. paratuberculosis* genomes.

TABLE 11

PCR identification of selected MAP-island regions from 29 clinical isolates of *M. paratuberculosis* and *M. avium* collected from different states

| Clinical | | Genomic island | | | | | |
|---|---|---|---|---|---|---|---|
| Isolate | Subspecies | MAP-1 | MAP-3 | MAP-5 | MAP-12 | MAP-16 | MAP-17 |
| JTC33666 | *M. paratub.* | + | + | + | + | + | + |
| JTC33770 | *M. paratub.* | + | + | + | + | + | + |
| CW303 | *M. paratub.* | + | + | + | + | + | + |
| 1B | *M. paratub.* | + | + | + | + | + | + |
| 3B | *M. paratub.* | + | + | + | + | + | + |
| 4B | *M. paratub.* | + | + | + | + | + | + |
| 5B | *M. paratub.* | + | + | + | + | + | + |
| DT3 | *M. paratub.* | − | + | + | + | + | + |
| DT9 | *M. paratub.* | − | + | + | + | + | + |
| DT12 | *M. paratub.* | + | + | + | + | + | + |
| DT19 | *M. paratub.* | + | + | + | + | + | + |
| JTC1281 | *M. paratub.* | − | + | + | + | + | + |
| JTC1282 | *M. paratub.* | − | + | + | + | + | + |
| JTC1283 | *M. paratub.* | − | + | + | + | + | + |
| JTC1285 | *M. paratub.* | − | − | + | + | + | − |
| JTC1286 | *M. paratub.* | + | + | + | + | + | + |
| T93 | *M. avium* | − | − | − | − | − | − |
| T99 | *M. avium* | − | N/A | + | − | + | + |
| T100 | *M. avium* | + | N/A | + | + | − | + |
| DT30 | *M. avium* | − | − | − | − | − | − |
| DT44 | *M. avium* | − | − | − | − | − | − |
| DT78 | *M. avium* | − | − | + | − | − | − |
| DT84 | *M. avium* | − | − | − | − | − | − |
| DT247 | *M. avium* | − | − | + | − | − | − |
| JTC956 | *M. avium* | N/A | − | N/A | − | + | + |
| JTC982 | *M. avium* | − | − | + | − | − | − |
| JTC1161 | *M. avium* | − | − | + | N/A | + | + |
| JTC1262 | *M. avium* | − | − | − | − | − | − |
| JTC33793 | *M. avium* | − | − | − | − | − | − |

Symbols (+ or −) denote presence or absence of genomic regions;
N/A denotes no amplification of DNA fragments.

Because the sequences of the inverted regions and of the flanking MAVs are known, it is possible to use the junction regions (sequences) to identify the presence of either *M. paratuberculosis* or *M. avium* in a sample. For example, using the right sets of primers, one skilled in the art would know to detect sequences that are specific to the junction regions that are characteristic for either *M. avium* or *M. paratuberculosis*.

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters normally encountered in clinical prevention and therapy, obvious to those skilled in the art, are within the scope of this invention. All publications, patents, and patent applications cited herein are incorporated by reference in their entirety for all purposes.

What is claimed is:

1. A composition comprising:

a) an isolated antigen selected from the group consisting of gcpE (SEQ ID NO:7), pstA (SEQ ID NO:8), kdpC (SEQ ID NO:9), papA2 (SEQ ID NO:10), impA (SEQ ID NO:11), umaA1 (SEQ ID NO:12), fabG2_2 (SEQ ID NO:13), aceAB (SEQ ID NO:14), mbtH2 (SEQ ID NO:15), IpqP (SEQ ID NO:16), map0834c (SEQ ID NO:17), cspB (SEQ ID NO:18), lipN (SEQ ID NO:19), or map1634 (SEQ ID NO:20) genes of *M. paratuberculosis* or their homologs, wherein the homolog has 90% sequence identity to the selected gene; and b) a pharmaceutically acceptable carrier.

2. The composition of claim 1 further comprising an adjuvant.

3. A composition comprising:

a) an isolated antigen selected from the group consisting of MAP-1 (SEQ ID NO:21), MAP-2 (SEQ ID NO:22), MAP-3 (SEQ ID NO:23), MAP-4 (SEQ ID NO:24), MAP-5 (SEQ ID NO:25), MAP-6 (SEQ ID NO:26), MAP-7 (SEQ ID NO:27), MAP-8 (SEQ ID NO:28), MAP-9 (SEQ ID NO:29), MAP-10 (SEQ ID NO:30), MAP-11 (SEQ ID NO:31), MAP-12 (SEQ ID NO:32), MAP-13 (SEQ ID NO:33), MAP-14 (SEQ ID NO:34), MAP-15 (SEQ ID NO:35), MAP-16 (SEQ ID NO:36), MAP-17 (SEQ ID NO:37), or MAP-18 (SEQ ID NO:38) genomic islands of *M. paratuberculosis* or their homologs, wherein the homolog has 90% sequence identity to the selected gene; and b) a pharmaceutically acceptable carrier.

4. A composition comprising an isolated mutant *M. paratuberculosis* or *M. avium* bacterium, wherein the mutant bacterium comprises a disruption of function of a gene selected from the group consisting of gcpE (SEQ ID NO:7), pstA (SEQ ID NO:8), kdpC (SEQ ID NO:9), papA2 (SEQ ID NO:10), impA (SEQ ID NO:11), umaA1 (SEQ ID NO:12), fabG2_2 (SEQ ID NO:13), aceAB (SEQ ID NO:14), mbtH2 (SEQ ID NO:15), IpqP (SEQ ID NO:16), map0834c (SEQ ID NO:17), cspB (SEQ ID NO:18), lipN (SEQ ID NO:19), and map1634 (SEQ ID NO:20) genes of *M. paratuberculosis* or their homologs, wherein the homolog has 90% sequence identity to the selected gene.

5. The composition of claim 4 further comprising an adjuvant.

6. A composition comprising an isolated mutant *M. paratuberculosis* or *M. avium* bacterium, wherein the mutant bacterium comprises a disruption of function of at least one gene from a genomic island selected from the group consisting of MAP-1 (SEQ ID NO:21), MAP-2 (SEQ ID NO:22), MAP-3 (SEQ ID NO:23), MAP-4 (SEQ ID NO:24), MAP-5 (SEQ ID NO:25), MAP-6 (SEQ ID NO:26), MAP-7 (SEQ ID NO:27), MAP-8 (SEQ ID NO:28), MAP-9 (SEQ ID NO:29), MAP-10 (SEQ ID NO:30), MAP-11 (SEQ ID NO:31), MAP-12 (SEQ ID NO:32), MAP-13 (SEQ ID NO:33), MAP-14 (SEQ ID NO:34), MAP-15 (SEQ ID NO:35), MAP-16 (SEQ ID NO:36), MAP-17 (SEQ ID NO:37), and MAP-18 (SEQ ID NO:38) genomic islands of *M. paratuberculosis* or their homologs, wherein the homolog has 90% sequence identity to the selected gene.

7. The composition of claim 6 further comprising an adjuvant.

8. The composition of claim 6 wherein the mutant *M. paratuberculosis* or *M. avium* bacterium comprises a disruption of function of a gene selected from the group consisting of pstA (SEQ ID NO: 8), papA2 (SEQ ID NO:10), umaA1 (SEQ ID NO:12), and fabG2_2 (SEQ ID NO:13).

9. A composition comprising:

a) a eukaryotic expression vector comprising a nucleotide sequence encoding an antigen selected from the group comprising gcpE (SEQ ID NO:7), pstA (SEQ ID NO:8), kdpC (SEQ ID NO:9), papA2 (SEQ ID NO:10), impA (SEQ ID NO:11), umaA1 (SEQ ID NO:12), fabG2_2 (SEQ ID NO:13), aceAB (SEQ ID NO:14), mbtH2 (SEQ ID NO:15), IpqP (SEQ ID NO:16), map0834c (SEQ ID NO:17), cspB (SEQ ID NO:18), lipN (SEQ ID NO:19), and map1634 (SEQ ID NO:20) genes of *M. paratuberculosis* or their homologs, wherein the homolog has 90% sequence identity to the selected gene; and b) a pharmaceutically acceptable carrier.

10. The composition of claim 9 further comprising an adjuvant.

11. A composition comprising:

a) a eukaryotic expression vector comprising a nucleotide sequence encoding an antigen selected from the group comprising MAP-1 (SEQ ID NO:21), MAP-2 (SEQ ID NO:22), MAP-3 (SEQ ID NO:23), MAP-4 (SEQ ID NO:24), MAP-5 (SEQ ID NO:25), MAP-6 (SEQ ID NO:26), MAP-7 (SEQ ID NO:27), MAP-8 (SEQ ID NO:28), MAP-9 (SEQ ID NO:29), MAP-10 (SEQ ID NO:30), MAP-11 (SEQ ID NO:31), MAP-12 (SEQ ID NO:32), MAP-13 (SEQ ID NO:33), MAP-14 (SEQ ID NO:34), MAP-15 (SEQ ID NO:35), MAP-16 (SEQ ID NO:36), MAP-17 (SEQ ID NO:37), and MAP-18 (SEQ ID NO:38) genomic islands of *M. paratuberculosis* or their homologs, wherein the homolog has 90% sequence identity to the selected gene; and b) a pharmaceutically acceptable carrier.

12. The composition of claim 11 further comprising an adjuvant.

* * * * *